United States Patent
Richardson et al.

(10) Patent No.: US 10,675,341 B2
(45) Date of Patent: *Jun. 9, 2020

(54) PARENTERAL NOROVIRUS VACCINE FORMULATIONS

(71) Applicant: Takeda Vaccines, Inc., Cambridge, MA (US)

(72) Inventors: Charles Richardson, Bozeman, MT (US); Thomas R. Foubert, Bozeman, MT (US)

(73) Assignee: Takeda Vaccines, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/836,030

(22) Filed: Dec. 8, 2017

(65) Prior Publication Data

US 2018/0185468 A1   Jul. 5, 2018

Related U.S. Application Data

(60) Division of application No. 14/796,614, filed on Jul. 10, 2015, now Pat. No. 9,867,876, which is a continuation of application No. 13/840,403, filed on Mar. 15, 2013, now Pat. No. 9,801,934, which is a continuation of application No. PCT/US2012/046222, filed on Jul. 11, 2012.

(60) Provisional application No. 61/506,447, filed on Jul. 11, 2011.

(51) Int. Cl.
   *A61K 39/12*     (2006.01)
   *A61K 39/125*    (2006.01)
   *A61K 39/39*     (2006.01)
   *A61K 39/00*     (2006.01)

(52) U.S. Cl.
   CPC .......... *A61K 39/12* (2013.01); *A61K 39/125* (2013.01); *A61K 39/39* (2013.01); *A61K 2039/5258* (2013.01); *A61K 2039/545* (2013.01); *A61K 2039/55505* (2013.01); *A61K 2039/55572* (2013.01); *A61K 2039/70* (2013.01); *C12N 2770/16034* (2013.01)

(58) Field of Classification Search
   None
   See application file for complete search history.

(56) References Cited

U.S. PATENT DOCUMENTS

| | | |
|---|---|---|
| 5,645,051 A | 7/1997 | Schultz et al. |
| 5,861,241 A | 1/1999 | Herrmann et al. |
| 5,953,727 A | 9/1999 | Maslyn et al. |
| 6,165,502 A | 12/2000 | Oleske et al. |
| 6,251,678 B1 | 6/2001 | Volkin et al. |
| 6,391,318 B1 | 5/2002 | Illum et al. |
| 6,491,919 B2 | 12/2002 | Crane |
| 6,572,862 B1 | 6/2003 | Estes et al. |
| 6,602,697 B1 | 8/2003 | Cook, III |
| 6,942,865 B2 | 9/2005 | Estes et al. |
| 7,067,638 B1 | 6/2006 | Takeda et al. |
| 7,481,997 B1 | 1/2009 | Hardy |
| 7,527,801 B2 | 5/2009 | Coit et al. |
| 7,955,603 B2 | 6/2011 | Richardson et al. |
| 8,119,145 B2 | 2/2012 | Coit et al. |
| 8,124,104 B2 | 2/2012 | Coit et al. |
| 8,142,793 B2 | 3/2012 | Coit et al. |
| 8,431,116 B2 | 4/2013 | Richardson et al. |
| 8,841,120 B2 | 9/2014 | Richardson et al. |
| 8,980,275 B2 | 3/2015 | Steadman et al. |
| 9,272,028 B2 | 3/2016 | Richardson et al. |
| 9,308,249 B2 | 4/2016 | Richardson et al. |
| 9,518,096 B2 | 12/2016 | Richardson et al. |
| 9,801,934 B2 | 10/2017 | Richardson et al. |
| 9,821,049 B2 | 11/2017 | Richardson et al. |
| 9,861,691 B2 | 1/2018 | Richardson et al. |
| 9,867,876 B2 | 1/2018 | Richardson et al. |
| 10,010,599 B2 | 7/2018 | Richardson et al. |
| 10,130,696 B2 | 11/2018 | Richardson et al. |
| 10,167,320 B2 | 1/2019 | Taylor |
| 10,512,682 B2 | 12/2019 | Richardson et al. |
| 2004/0063188 A1 | 4/2004 | Robinson et al. |
| 2004/0265377 A1 | 12/2004 | Seager |
| 2005/0152911 A1 | 7/2005 | Hardy |
| 2005/0154053 A1 | 7/2005 | Rhijn et al. |
| 2005/0155113 A1 | 7/2005 | Hamilton et al. |
| 2005/0215501 A1 | 9/2005 | Lipford et al. |
| 2005/0260225 A1 | 11/2005 | Goldberg et al. |
| 2007/0207526 A1 | 9/2007 | Coit et al. |
| 2008/0299152 A1 | 12/2008 | Richardson et al. |
| 2010/0150961 A1 | 6/2010 | Vedvick et al. |

(Continued)

FOREIGN PATENT DOCUMENTS

| | | |
|---|---|---|
| EP | 1186890 A1 | 3/2002 |
| EP | 2360175 A2 | 8/2011 |

(Continued)

OTHER PUBLICATIONS

Extended European Search Report for European Patent Application No. 18158843.5, dated Jun. 15, 2018, 10 pages.

(Continued)

*Primary Examiner* — Benjamin P Blumel
(74) *Attorney, Agent, or Firm* — Cooley LLP

(57) ABSTRACT

The present invention relates to single dose parental vaccine compositions comprising mixtures of monovalent Norovirus virus-like particles. Methods of conferring protective immunity against Norovirus infections in a human subject by administering such compositions are also disclosed.

18 Claims, 12 Drawing Sheets
Specification includes a Sequence Listing.

(56) References Cited

U.S. PATENT DOCUMENTS

| | | |
|---|---|---|
| 2010/0266636 A1 | 10/2010 | Richardson et al. |
| 2011/0070260 A1 | 3/2011 | Baric et al. |
| 2011/0182975 A1 | 7/2011 | Richardson et al. |
| 2011/0195113 A1 | 8/2011 | Richardson et al. |
| 2012/0093861 A1 | 4/2012 | Richardson et al. |
| 2012/0156243 A1 | 6/2012 | Richardson et al. |
| 2013/0273102 A1 | 10/2013 | Richardson et al. |
| 2013/0273105 A1 | 10/2013 | Richardson et al. |
| 2013/0273147 A1 | 10/2013 | Richardson et al. |
| 2013/0273148 A1 | 10/2013 | Richardson et al. |
| 2014/0286994 A1 | 9/2014 | Richardson et al. |
| 2015/0023995 A1 | 1/2015 | Richardson et al. |
| 2016/0000899 A1 | 1/2016 | Richardson et al. |
| 2016/0008455 A1 | 1/2016 | Richardson et al. |
| 2019/0125853 A1 | 5/2019 | Richardson et al. |
| 2019/0381164 A1 | 12/2019 | Richardson et al. |

FOREIGN PATENT DOCUMENTS

| | | |
|---|---|---|
| JP | 10-500847 | 1/1998 |
| JP | 2002-508748 A | 3/2002 |
| JP | 2002-536340 A | 10/2002 |
| JP | 2005-200420 A | 7/2005 |
| JP | 2005-524674 A | 8/2005 |
| JP | 2005-525415 A | 8/2005 |
| JP | 2005-538939 A | 12/2005 |
| JP | 2006-502979 A | 1/2006 |
| JP | 2006-507800 A | 3/2006 |
| JP | 2006-516638 A | 7/2006 |
| JP | 2006-518748 A | 8/2006 |
| JP | 2007-145775 A | 6/2007 |
| JP | 2007-537137 A | 12/2007 |
| JP | 2008-511556 A | 4/2008 |
| JP | 2008-526870 A | 7/2008 |
| JP | 2009-516529 A | 4/2009 |
| JP | 2010-505766 A | 2/2010 |
| JP | 2011-506264 A | 3/2011 |
| JP | 5476544 B | 4/2014 |
| WO | WO 1992/016543 A1 | 10/1992 |
| WO | WO 1993/021325 A1 | 10/1993 |
| WO | WO 1998/050071 A1 | 11/1998 |
| WO | WO 2000/035479 A1 | 6/2000 |
| WO | WO 2000/079280 A1 | 12/2000 |
| WO | WO 2003/077942 A2 | 9/2003 |
| WO | WO 2003/078455 A2 | 9/2003 |
| WO | WO 2005/020889 A2 | 3/2005 |
| WO | WO 2005/030806 A2 | 4/2005 |
| WO | WO 2005/032457 A2 | 4/2005 |
| WO | WO 2005/060966 A1 | 7/2005 |
| WO | WO 2006/044857 A2 | 4/2006 |
| WO | WO 2006/067632 A2 | 6/2006 |
| WO | WO 2006/074303 A2 | 7/2006 |
| WO | WO 2006/086188 A2 | 8/2006 |
| WO | WO 2006/091517 A2 | 8/2006 |
| WO | WO 2006/097530 A2 | 9/2006 |
| WO | WO 2006/136566 A1 | 12/2006 |
| WO | WO 2007/053188 A2 | 5/2007 |
| WO | WO 2007/081447 A2 | 7/2007 |
| WO | WO 2008/042789 A1 | 4/2008 |
| WO | 2009033229 A1 † | 3/2009 |
| WO | WO 2009/039229 A2 | 3/2009 |
| WO | 2010017542 A1 † | 2/2010 |
| WO | WO 2010/017542 A1 | 2/2010 |
| WO | WO 2010/084298 A1 | 7/2010 |
| WO | WO 2010/092476 A1 | 8/2010 |
| WO | WO 2011/150249 A1 | 12/2011 |
| WO | WO 2013/009849 A1 | 1/2013 |

OTHER PUBLICATIONS

Parra, et al., "Immunogenicity and specificity of norovirus Consensus GII.4 virus-like particles in monovalent and bivalent vaccine formulations." Vaccine (2012); 30 (24): 3580-3586.

Allen et al., "Analysis of Amino Acid Variation in the P2 Domain of the GII-4 Norovirus VP1 Protein Reveals Putative Variant-Specific Epitopes," PLOS One, vol. 3: e1485, 2008.

Ando et al., "Genetic Classification of 'Norwalk-like Viruses,'" The Journal of Infectious Diseases, vol. 181(Suppl 2): S336-S348, 2000.

Ausar et al., "Conformational stability and disassembly of norwalk virus like particles: effect of pH and temperature,"J. Biol. Chem., vol. 281: 19478-19488, 2006.

Baldrick et al., Safety evaluation of monophosphoryl lipid A (MPL): an immunostimulatory adjuvant. Regulatory Toxicology and Pharmacology 2002; vol. 35:398-413.

Baldridge et al., Monophosphoryl lipid A enhances mucosal and systemic immunity to vaccine antigens following intranasal administration. Vaccine 2000; vol. 18:2416-2425.

Baldridge et al., "Taking a Toll on human disease: Toll-like receptor 4 agonists as vaccine adjuvants and monotherapeutic agents," Exp. Opin. Biol. Ther. 4(7):1129-1138 (2004).

Ball et al., Oral Immunization with Recombinant Norwalk Virus-Like Particles Induces a Systemic and Mucosal Immune Response in Mice. Journal of Virology 1998; vol. 72(2): 1345-1353.

Ball et al., Recombinant Norwalk virus-like particles given orally to volunteers: phase I study. Gastroenterology 1999; vol. 117:40-48.

Ball et al., "Recombinant Norwalk virus-like particles as an oral vaccine." Archives of Virology (1996); 12: 243-249.

Baric et al., "Expression and Self-Assembly of Norwalk Virus Capsid Protein from Venezuelan Equine Encephalitis Virus Replicons," J. Virol. 76(6):3023-3030 (2002).

Bertolotti-Ciarlet et al., "Structural Requirements for the Assembly of Norwalk Virus-Like Particles," J. Virol. 76(8):4044-4055 (2002).

Bok et al., "Chimpanzees as an animal model for human norovirus infection and vaccine development," Proc. Natl. Acad. Sci. USA 108(1):325-330 (2011).

Broadbent and Subbarao, "Influenza virus vaccines: lessons from the 2009 H1N1 pandemic," Curr. Opin. Virol. 1:254-262 (2011).

Bull et al., "Emergence of a New Norovirus Genotype II.4 Variant Associated with Global Outbreaks of Gastroenteritis," Journal of Clinical Microbiology, vol. 44: 327-333, 2006.

Cachia et al., "The use of synthetic peptides in the design of a consensus sequence vaccine for Pseudomonas aeruginosa," J. Pept. Res. 52(4):289-299 (1998).

Cao et al., "Structural Basis for the Recognition of Blood Group Trisaccharides by Norovirus," J. Virol. 81(11):5949-5957 (2007).

Carpenter et al., Rational design of stable lyophilized protein formulations: some practical advice, Pharmaceutical Research, vol. 14: 969-975, 1997.

Chachu, Karen A., et al. "Immune mechanisms responsible for vaccination against and clearance of mucosal and lymphatic norovirus infection." PLoS Pathog (2008); 4.12: e1000236, 13 pages.

Cheetham et al., "Binding patterns of human norovirus-like particles to buccal and intestinal tissues of gnotobiotic pigs in relation to A/H histo-blood group antigen expression," Journal of Virology, vol. 81: 3535-3544, 2007.

Chen et al., "X-ray structure of a native calicivirus: Structural insights into antigenic diversity and host specificity," Proc. Natl Acad. Sci. USA 103(21):8048-8053 (2006).

Childers et al., "Adjuvant activity of monophosphoryl lipid A for nasal and oral immunization with soluble or liposome-associated antigen," Infection and Immunity, vol. 68: 5509-5516, 2000.

Clark and Offit, "Vaccines for rotavirus gastroenteritis universally needed for infants." Pediatric Annals (2004); 33(8): 537-543.

Cuellar et al., "Size and mechanical stability of norovirus capsids depend on pH: a nanoindentation study," J. Gen. Virol. 91:2449-2456 (2010).

Da Silva et al., "Adsorption and Aggregation Properties of Norovirus GI and GII Virus-like Particles Demonstrate Differing Responses to Solution Chemistry," Environ. Sci. Technol. 45(2):520-526 (2011).

Dagan et al., "Reduced Response to Multiple Vaccines Sharing Common Protein Epitopes That Are Administered Simultaneously to Infants," Infect. Immun. 66(5):2093-2098 (1998).

Davis and Illum, Absorption enhancers for nasal drug delivery. Clinical Pharmacokinetics 2003; vol. 42:1107-1128.

Estes et al., Norwalk Virus Vaccines: Challenges and Progress. The Journal of Infectious Disease 2000; vol. 181(Suppl 2): S367-373.

(56) References Cited

OTHER PUBLICATIONS

Extended European Search Report, EP appl. No. 13157572.2, 9 pages (dated Jul. 23, 2013).
Extended European Search Report, EP appl. No. 13157573.0, 6 pages (dated Apr. 5, 2013).
Extended European Search Report, EP appl. No. 13173005.3, 5 pages (dated Jul. 16, 2013).
Extended European Search Report, EP appln. No. 07853688.5, 9 pages (dated Sep. 22, 2010).
Fankhauser et al., "Molecular Epidemiology of "Norwalk-like viruses" in Outbreaks of Gastroenteritis in the United States," J. Infect. Dis. 178(6):1571-1578 (1998).
Foubert et al., "Preclinical Development of a Broad Spectrum Norovirus Vaccine," AAPS National Biotechnology Conference, http://abstracts.aapspharmaceutica.com/ExpoNBC09/CC/forms/attendee/index.aspx?content=sessionInfo&sessionId=150 (2009).
Frey et al., "Interference of Antibody Production to Hepatitis B Surface Antigen in a Combination Hepatitis A/Hepatitis B Vaccine," J. Infect. Dis. 180:2018-2022 (1999).
Giannini et al., "Enhanced humoral and memory B cellular immunity using HPV16/18 L1 VLP vaccine formulated with the MPL/aluminium salt combination (AS04) compared to aluminium salt only," Vaccine 24:5937-5949 (2006).
Glass, R.I., et al. "Norovirus gastroenteritis." New England Journal of Medicine (2009); 361.18: 1776-1785.
Gray et al., Detection of immunoglobulin M (IgM), IgA, and IgG Norwalk virus-specific antibodies by indirect enzyme-linked immunosorbent assay with baculovirus-expressed Norwalk virus capsid antigen in adult volunteers challenged with Norwalk virus. Journal of Clinical Microbiology 1994; vol. 32:3059-3063.
Guerrero et al., Recombinant Norwalk Virus-Like Particles Administered Intranasally to Mice Induce Systemic and Mucosal (Fecal and Vaginal) Immune Responses. Journal of Virology 2001; vol. 75:9713-9722.
Guy et al., "Evaluation of Interferences between Dengue Vaccine Serotypes in a Monkey Model,"Am. J. Trop. Med. Hyg. 80(2):302-311 (2009).
Han et al., Immune responses to bovine norovirus-like particles with various adjuvants and analysis of protection in gnotobiotic calves. Vaccine 2006; vol. 24:317-326.
Han et al., "Thermosensitive and mucoadhesive delivery systems of mucosal vaccines," Methods, vol. 38:106-111, 2006.
Hansman et al., Genetic and antigenic diversity among Noroviruses. Journal of General Virology 2006; vol. 87: 909-919.
Hardy, Michele E., "Norovirus protein structure and function", FEMS Microbiology (2005); 253: 1-8.
Harrington et al., "Systemic, Mucosal, and Heterotypic Immune Induction in Mice Inoculated with Venezuelan Equine Encephalitis Replicons Expressing Norwalk Virus-Like Particles," J. Virol. 76(2):730-742 (2002).
Herbst-Kralovetz et al., "Norwalk virus-like particles as vaccines," Exp. Rev. Vaccines 9(3):299-307 (2010).
Huang et al., "Noroviruses Bind to Human ABO, Lewis, and Secretor Histo-Blood Group Antigens: Identification of 4 Distinct Strain-Specific Patterns," J. Infect. Dis. 188(1):19-31 (2003).
Hutson et al., Norovirus disease: changing epidemiology and host susceptibility factors. Trends in Microbiology 2004; vol. 12(6):279-287.
Hutson et al., "Norwalk Virus-Like Particle Hemagglutination by Binding to H Histo-Blood Group Antigens," J. Virol. 77(1):405-415 (2003).
Illum et al., Chitosan as a novel nasal delivery system for peptide drugs. Pharmaceutical Research 1994; vol. 11:1186-1189.
Illum et al., Chitosan as a novel nasal delivery system for vaccines. Advanced Drug Delivery Reviews 2001; vol. 51:81-96.
Illum et al., Nasal drug delivery—possibilities, problems and solutions. Journal of Controlled Release 2003; vol. 87:187-198.
International Search Report, 2 pages, PCT appl. No. PCT/US2007/079929 (dated Mar. 11, 2008).
International Preliminary Report on Patentability, PCT appl. No. PCT/US2007/079929 dated Mar. 31, 2009.
International Search Report, 3 pages, PCT appl. No. PCT/US2008/076763 (dated Jul. 15, 2009).
International Preliminary Report on Patentability, 6 pages, PCT appl. No. PCT/US2008/076763 dated Mar. 24, 2010.
International Search Report, 3 pages, PCT appl. No. PCT/US2009/053249 (dated Dec. 14, 2009).
International Preliminary Report on Patentability, 8 pages, PCT appl. No. PCT/US2009/053249 dated Feb. 8, 2011.
International Search Report, 3 pages, PCT appl. No. PCT/US2012/046222 (dated Oct. 2, 2012).
International Preliminary Report on Patentability, 7 pages, PCT appl. No. PCT/US2012/046222, dated Jan. 14, 2014.
Jaimes et al., "Maturation and Trafficking Markers on Rotavirus-Specific B Cells during Acute Infection and Convalescence in Children," J. Virol 78:10967-10976 (2004).
Jiang et al., "Expression, Self-Assembly, and Antigenicity of the Norwalk Virus Capsid Protein," J. Virol. 66(11):6527-6532 (1992).
Jiang et al., "Norwalk virus genome cloning and characterization," Science 250:1580-1583 (1990).
Johnson et al., Multiple Challenge Study of Host Susceptibility to Norwalk Gastroenteritis in U.S. Adults. The Journal of Infectious Disease 1990; vol. 161: 18-21.
Kamata et al., "Increased Frequency of Surface IgA-Positive Plasma Cells in the Intestinal Lamina Propia and Decreased IgA Excretion in Hyper IgA (HIGA) Mice, a Murine Model of IgA Nephropathy with Hyperserum IgA," J. Immunol. 165:1387-1394 (2000).
Kawana et al., "A surface immunodeterminant of human papillomavirus type 16 minor capsid protein L2." Virology (1998); 245.2: 353-359.
Kitamoto et al., "Cross-Reactivity among Several Recombinant Calicivirus Virus-Like Particles (VLPs) with Monoclonal Antibodies Obtained from Mice Immunized Orally with One Type of VLP." J. Clin. Microbiol. (2002); 40(7): 2459-2465.
Larke et al., "Combined single-clade candidate HIV-1 vaccines induce T cell responses limited multiple forms of in vivo immune interference," Eur. J. Immunol. 37:566-577 (2007).
Lew et al., "Molecular Characterization and Expression of the Capsid Protein of a Norwalk-like Virus Recovered from a Desert Shield Troop with Gastroenteritis," Virol. 319-325 (1994).
Ligocyte Pharmaceuticals, "Ligocyte Pharmaceuticals initiates U.S. clinical trial of norovirus vaccine," http://www.ligocyte.com/news/documents/LIGOCYTE-PHARMACEUTICALS-4-3-2007.pdf, Apr. 3, 2007, 2 pages.
Lin, S.W., et al., "Intramuscular rather than oral administration of replication-defective adenoviral vaccine vector induces specific CD8+ T-cell responses in the gut." Vaccine (2007); 25(12): 2187-2193.
Lindell et al., "Molecular Epidemiology of Norovirus Infections in Stockholm, Sweden, during the Years 2000 to 2003: Association of the GGIIb Genetic Cluster with Infection in Children," Journal of Clinical Microbiology, vol. 43: 1086-1092, 2005.
Lindesmith et al., Cellular and humoral immunity following Snow Mountain virus challenge. Journal of Virology 2005; vol. 79(5): 2900-2909.
Lindesmith et al., Human susceptibility and resistance to Norwalk infection. Nature Medicine 2003; vol. 9(5): 548-553.
Lindesmith et al., "Mechanisms of GII.4 Norovirus Persistence in Human Populations," PLOS One, vol. 5: e31, 2008.
Li U, Guangliang, et al. "Primary high-dose murine norovirus 1 infection fails to protect from secondary challenge with homologous virus." Journal of Virology (2009); 83.13: 6963-6968.
Lobue et al., "Alphavirus adjuvanted norovirus-like particle vaccines: heterologous, humoral, and mucosal immune responses protect against murine norovirus challenge," J. Virol., vol. 83(7): 3212-3227, 2009.
Lobue et al., Multivalent Norovirus vaccines induce strong mucosal and systemic blocking antibodies against multiple strains. Vaccine 2006; vol. 24(24): 5220-5234.
Malcolmson and Embleton, "Dry powder formulations for pulmonary delivery," Pharmaceutical Science and Technology Today, vol. 1:394-398, 1998.

(56) References Cited

OTHER PUBLICATIONS

Martin et al., "Role of Innate Immune Factors in the Adjuvant Activity of Monophosphoryl Lipid A," Infect. Immun. 71(5):2498-2507 (2003).
Mason et al., "Expression of Norwalk virus capsid protein in transgenic tobacco and potato and its oral immunogenicity in mice," Proc. Natl Acad. Sci. USA 93(11):5335-5340 (1996).
Matsui et al., Immunity to Calicivirus infection. The Journal of Infectious Diseases 2000; vol. 181(S2): S331-335.
McBurney et al., "Developing Broadly Reactive HIV-1/AIDS Vaccines: A Review of Polyvalent and Centralized HIV-1 Vaccines," Curr. Pharm. Design 13(19):1957-1964 (2007).
Mead et al., Food Related Illness and Death in the U.S., Emerging Infectious Diseases 1999; vol. 5(5): 607-635.
Midthun and Kapikian. "Rotavirus vaccines: an overview." Clinical Microbiology Reviews (1996); 9(3): 423-434.
MMWR, 2011, Updated Norovirus Outbreak Management and Disease Prevention Guidelines, 20 pages. [https://www.cdc.gov./mmwr/preview/mmwrhtml/rr6003a1.htm] downloaded May 1, 2017.
Muthumani et al., "Immunogenicity of novel consensus-based DNA vaccines against Chikungunya virus," Vaccine 26(40):5128-5134 (2008).
Nakata, S., "Vaccine development for Norwalk Virus." Nippon Rinsho (2002); 60(6): 1222-1227 (with English Abstract and English translation), 12 pages.
Nicollier-Jamot et al., Recombinant Virus-like Particles of a Norovirus (Genogroup II Strain) Administered Intranasally and Orally with Mucosal Adjuvants LT and LT(R192G) in BALB/c Mice Induce Specific Humoral and Cellular Th1/Th2-like Immune Responses. Vaccine 2004; vol. 22:1079-1086.
Noel et al., Correlation of patient immune responses with genetically characterized small round-structured viruses involved in outbreaks of nonbacterial acute gastroenteritis in the United States, 1990 to 1995. Journal of Medical Virology 1997; vol. 53:372-383.
Notice of Opposition in European Patent No. EP 2601970 (Application No. EP 13157573.0), filed Jul. 21, 2017, 40 pages.
O'Hagan et al., "Recent developments in adjuvants for vaccines against infectious diseases," Biomol. Eng. 18(3):69-85 (2001).
Oliver, S. L., et al. "Genotype 1 and genotype 2 bovine noroviruses are antigenically distinct but share a cross-reactive epitope with human noroviruses." Journal of Clinical Microbiology (2006); 44.3: 992-998.
Parra and Green, "Sequential Gastroenteritis Episodes Caused by 2 Norovirus Genotypes," Emerg. Infect. Dis. 20(6):1016-1018 (2014).
Parrino et al., Clinical immunity in acute gastroenteritis caused by Norwalk agent. New England Journal of Medicine 1977; vol. 297:86-89.
Partial European Search Report, 7 pages, EP appl. No. 13157572.2 (dated Apr. 5, 2013).
Pastrana et al., "Cross-neutralization of cutaneous and mucosal Papillomavirus types with anti-sera to the amino terminus of L2." Virology (2005); 337.2: 365-372.
Pelosi et al., "The Seroepidemiology of Genogroup 1 and Genogroup 2 Norwalk-Like Viruses in Italy," J. Med. Virol. 58:93-99 (1999).
Periwal et al., A Modified Cholera Holotoxin CT-E29H Enhances Systemic and Mucosal Immune Responses to Recombinant Norwalk Virus-like Particle Vaccine. Vaccine 2003; vol. 21:376-385.
Prasad et al., "Structural studies of recombinant norwalk capsids," J. Infect. Dis., vol. 181(s2), S317-S321, 2000.
Rasmussen et al., "In Multiple Myeloma Clonotypic CD38-/CD19+/CD27+ Memory B Cells Recirculate Through Bone Marrow, Peripheral Blood and Lymph Nodes," Leuk. Lymph. 45(7):1413-1417 (2004).
Reagan-Shaw et al., "Dose translation from animal to human studies revisited," FASEB J. 22:659-661 (2007).
Richardson et al., "Norovirus Vaccine Formulations," U.S. Appl. No. 12/816,495, filed Jun. 16, 2010.
Richardson et al., "Norovirus virus-like particle vaccines for the prevention of acute gastroenteritis," Expert Rev. Vaccines 12(2):155-167 (2013).

Sha et al., "Activation of Airway Epithelial Cells by Toll-Like Receptor Agonists," Am. J. Respir. Cell Mol. Biol. 31(3):358-364 (2004).
Siebenga et al., "Epochal Evolution of GGII.4 Norovirus Capsid Proteins from 1995 to 2006," Journal of Virology, vol. 81: 9932-9941, 2007.
Singh et al., "A preliminary evaluation of alternative adjuvants to alum using a range of established and new generation vaccine antigens," Vaccine 24(10):1680-1686 (2006).
Song, Wei, et al., "Research Progress on Molecular Biology Feature of Noroviruses and its Subunit Vaccine." Journal of Agricultural Science and Technology (2010); 12(6): 43-48 (with English Abstract).
Souza et al., "A human norovirus-like particle adjuvanted with Iscom or mLT induces cytokine and antibody responses and protection to the homologous GII.4 human norovirus in a gnotobiotic pig disease model," Vaccine, vol. 25: 8448-8459, 2007.
Supplementary European Search Report, 13 pages, EP appl. No. 08832560.0 (dated Apr. 5, 2012).
Supplementary European Search Report, 8 pages, EP appl. No. 09805653.4 (dated Dec. 2, 2011).
Supplementary European Search Report, EP appl. No. 12811916.1, 8 pages (dated Feb. 20, 2015).
Tacket et al., Humoral, mucosal, and cellular immune response to oral Norwalk virus-like particles in volunteers. Clinical Immunology 2003; vol. 108: 241-247.
Tacket et al., "Human immune responses to a novel norwalk virus vaccine delivered in transgenic potatoes.," J. Infect. Dis., vol. 182(1): 302-305, 2000.
Ugwoke et al., "Nasal mucoadhesive drug delivery: Background, applications, trends and future perspectives," Advanced Drug Delivery Reviews, vol. 57: 1640-1665, 2005.
Wang et al., "Effective synthetic peptide vaccine for foot-and-mouth disease in swine," Vaccine 20(19-20):2603-2610 (2002).
Written Opinion of the International Searching Authority, 4 pages, PCT appl. No. PCT/US2007/079929 (dated Mar. 11, 2008).
Written Opinion of the International Searching Authority, 5 pages, PCT appl. No. PCT/US2008/076763 (dated Jul. 15, 2009).
Written Opinion of the International Searching Authority, 7 pages, PCT appl. No. PCT/US2009/053249 (dated Dec. 14, 2009).
Written Opinion of the International Searching Authority, 6 pages, PCT appl. No. PCT/US2012/046222 (dated Oct. 2, 2012).
Wyatt et al., Comparison of three agents of acute infectious nonbacterial gastroenteritis by cross-challenge in volunteers. Journal of Infectious. Diseases 1974.; vol. 129:709-714.
Xia et al., "Norovirus Capsid Protein Expressed in Yeast Forms Virus-like Particles and Stimulates Systemic and Mucosal Immunity in Mice Following an Oral Administration of Raw Yeast Extracts," J. Med Virol. 79:74-83 (2007).
Zhang et al., "Trivalent Human Papillomavirus (HPV) VLP vaccine covering HPV type 58 can elicit high level of humoral immunity but also induce immune interference among component types," Vaccine 28:3479-3487 (2010).
Zheng et al., "Norovirus classification and proposed strain nomenclature," Virology 346:312-323 (2006).
Extended European Search Report, EP Appln. No. 17199372.8, dated Jan. 23, 2018, 10 pages.
Nakagomi, Osamu, [Commonly-discussed Infectious Diseases], Norovirus infection: some new developments in its research. Modern Media (2004); vol. 50, No. 6, pp. 133-142 (with partial English translation), 11 pages.
Singh, et al., "A novel bioadhesive intranasal delivery system for inactivated influenza vaccines." Journal of Controlled Release (2001); 70: 267-276.
Van Der Lubben, et al., "Chitosan and its derivatives in mucosal drug and vaccine delivery." European Journal of Pharmaceutical Sciences (2001); 14: 201-207.
Kumru, et al., "Vaccine instability in the cold chain: Mechanisms, analysis and formulation strategies." Biologicals (2014); 42 (5): 237-259.
U.S. Appl. No. 12/765,641 (abandoned).
U.S. Appl. No. 13/330,854 (abandoned).
U.S. Appl. No. 12/678,813 (pending).
U.S. Appl. No. 13/836,446 (pending).

(56) References Cited

OTHER PUBLICATIONS

Communication from the European Patent Office dated Sep. 4, 2018 in Opposition Proceedings against European Patent No. EP 2601970 (Application No. EP 13157573.0), with Response to Opposition Division's Preliminary Opinion, filed Aug. 30, 2018, 17 pages.

Bok, et al., "Evolutionary Dynamics of GII.4 Noroviruses over a 34-Year Period." Journal of Virology (2009); 83 (22): 11890-11901.

Cannon, et al., "Herd Immunity to GII.4 Noroviruses Is Supported by Outbreak Patient Sera." Journal of Virology (2009); 83 (11): 5363-5374.

Document 4 of the Handouts of the meeting on food poisoning held on Aug. 17, 2007, Food Sanitation Council, Pharmaceutical Affairs and Food Sanitation Council, Ministry of Health, Labour and Welfare, and English Summary, 21 pages.

Lindesmith, et al., "Mechanisms of GII.4 Norovirus Persistence in Human Populations." PLoS Medicine (2008); 5 (2): 269-290.

Motomura, et al., "Divergent Evolution of Norovirus GII/4 by Genome Recombination from May 2006 to Feb. 2009 in Japan." Journal of Virology (2010); 84 (16): 8085-8097.

Motomura, et al., "Identification of Monomorphic and Divergent Haplotypes in the 2006-2007 Norovirus GI1/4 Epidemic Population by Genomewide Tracing of Evolutionary History." Journal of Virology (2008); 82(22): 11247-11262.

Parra, et al., "Static and Evolving Norovirus Genotypes: Implications for Epidemiology and Immunity." PLoS Pathog. (2017); 13 (1): e1006136.

Sato, "Survival strategies of human norovirus." Virus, official journal of the Japanese Society for Virology (2010); 60 (1): 21-32 (and English Abstract).

Sato, et al., "Evolutionary Constraints on the Norovirus Pandemic Variant GII.4_2006b over the Five-Year Persistence in Japan." Frontiers in Microbiology (2017); 8 (410): 1-9.

Third Party Observation against EP Application No. 17199372.8, dated Mar. 8, 2019, 22 pages.

EPO Communication dated Mar. 14, 2019 regarding Third Party Observation against EP Application No. 17199372.8, dated Mar. 8, 2019, 1 page.

El-Kamary, S.S., et al., "Adjuvanted Intranasal Norwalk Virus-Like Particle Vaccine Elicits Antibodies and Antibody-Secreting Cells That Express Homing Receptors for Mucosal and Peripheral Lymphoid Tissues." J. Infect Dis. (Dec. 2010); 202(11): 1649-1658.

Liu, X.S., et al., "Mucosal Immunisation with Papillomavirus Virus-like Particles Elicits Systemic and Mucosal Immunity in Mice." Virology (Dec. 1998); 252(1): 39-45.

Gilbert, P.B., et al., "Fold Rise in Antibody Titers by Measured by Glycoprotein-Based Enzyme-Linked Immunosorbent Assay Is an Excellent Correlate of Protection for a Herpes Zoster Vaccine, Demonstrated via the Vaccine Efficacy Curve". J Infect Dis. (Nov. 15, 2014); 210(10): 1573-1581. Epub May 13, 2014.

Office Action in European Patent Application No. EP 17199372.8 dated Dec. 13, 2019, 5 pages.

Office Action (and English translation) in Vietnamese Patent Application No. 1-2014-00378 dated Oct. 28, 2019, 3 pages.

Canadian Application No. 2,841,356, Office Action dated Sep. 6, 2019, 3 pages.

Indonesian Application No. P00201400785, Office Action dated Sep. 19, 2019 (and English translation), 6 pages.

Ozan S. Kumru, et al., Biologicals, vol. 42, Issue 5, Sep. 2014, pp. 237-259.†

† cited by third party

PARENTERAL NOROVIRUS VACCINE FORMULATIONS

CROSS REFERENCE TO RELATED APPLICATIONS

This application is the Divisional of application Ser. No. 14/796,614, filed Jul. 10, 2015, which is a Continuation of application Ser. No. 13/840,403, filed Mar. 15, 2013, now U.S. Pat. No. 9,801,934, which is a Continuation of PCT/US2012/046222, filed Jul. 11, 2012, which claims the benefit of Provisional Application 61/506,447, filed on Jul. 11, 2011, the contents of each are herein incorporated by reference in their entireties.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: LIGO_024_03US_SeqList_ST25, date recorded on Jan. 30, 2018, file size 5 kilobytes).

FIELD OF THE INVENTION

The invention is in the field of vaccines, particularly vaccines for Noroviruses. In addition, the invention relates to methods of preparing vaccine compositions and methods of inducing and evaluating protective immune responses against Norovirus in humans.

BACKGROUND OF THE INVENTION

Noroviruses are non-cultivatable human Caliciviruses that have emerged as the single most important cause of epidemic outbreaks of nonbacterial gastroenteritis (Glass et al., 2000; Hardy et al., 1999). The clinical significance of Noroviruses was under-appreciated prior to the development of sensitive molecular diagnostic assays. The cloning of the prototype genogroup I Norwalk virus (NV) genome and the production of virus-like particles (VLPs) from a recombinant Baculovirus expression system led to the development of assays that revealed widespread Norovirus infections (Jiang et al. 1990; 1992).

Noroviruses are single-stranded, positive sense RNA viruses that contain a non-segmented RNA genome. The viral genome encodes three open reading frames, of which the latter two specify the production of the major capsid protein and a minor structural protein, respectively (Glass et al. 2000). When expressed at high levels in eukaryotic expression systems, the capsid protein of NV, and certain other Noroviruses, self-assembles into VLPs that structurally mimic native Norovirus virions. When viewed by transmission electron microscopy, the VLPs are morphologically indistinguishable from infectious virions isolated from human stool samples.

Immune responses to Noroviruses are complex, and the correlates of protection are just now being elucidated. Human volunteer studies performed with native virus demonstrated that mucosally-derived memory immune responses provided short-term protection from infection and suggested that vaccine-mediated protection is feasible (Lindesmith et al. 2003; Parrino et al. 1977; Wyatt et al., 1974).

Although Norovirus cannot be cultivated in vitro, due to the availability of VLPs and their ability to be produced in large quantities, considerable progress has been made in defining the antigenic and structural topography of the Norovirus capsid. VLPs preserve the authentic confirmation of the viral capsid protein while lacking the infectious genetic material. Consequently, VLPs mimic the functional interactions of the virus with cellular receptors, thereby eliciting an appropriate host immune response while lacking the ability to reproduce or cause infection. In conjunction with the NIH, Baylor College of Medicine studied the humoral, mucosal and cellular immune responses to NV VLPs in human volunteers in an academic, investigator-sponsored Phase I clinical trial. Orally administered VLPs were safe and immunogenic in healthy adults (Ball et al. 1999; Tacket et al. 2003). But, multiple doses of a relatively high amount of VLPs were required to observe an immune response. At other academic centers, preclinical experiments in animal models have demonstrated enhancement of immune responses to VLPs when administered intranasally with bacterial exotoxin adjuvants (Guerrero et al. 2001; Nicollier-Jamot et al. 2004; Periwal et al. 2003; Souza et al. (2007) Vaccine, Vol. 25(50):8448-59). However, protective immunity against Norovirus in humans remains elusive because the indicators of a protective immune response in humans have still not been clearly identified (Herbst-Kralovetz et al. (2010) Expert Rev. Vaccines 9(3), 299-307).

SUMMARY OF THE INVENTION

The present invention is based, in part, on the discovery that a single dose of a Norovirus vaccine elicits a rapid, robust protective immune response against Norovirus in humans when administered parenterally. Accordingly, the present invention provides a method of eliciting protective immunity against Norovirus in a human comprising administering parenterally to the human no more than a single dose of a vaccine composition, said composition comprising genogroup I and/or genogroup II Norovirus VLPs, wherein said composition induces at least a three-fold increase in Norovirus-specific serum antibody titer as compared to the titer in the human prior to administration of the composition. In certain embodiments, the increase in Norovirus-specific antibody titer is induced within seven days of administration of the single dose of the composition. In some embodiments, the vaccine composition is administered to the human via an intravenous, subcutaenous, intradermal, or intramuscular route of administration. In one embodiment, the vaccine composition is administered to the human by an intramuscular route of administration.

The single dose vaccine compositions can comprise doses of about 5 µg to about 150 of genogroup I Norovirus VLPs, genogroup II Norovirus VLPs, or both. In embodiments in which the single dose vaccine compositions comprise both genogroup I and genogroup II Norovirus VLPs, the dose of each VLP can be the same or different. In one embodiment, the composition comprises no more than 50 µg of genogroup I Norovirus VLPs. In another embodiment, the composition comprises no more than 25 µg of genogroup I Norovirus VLPs. In yet another embodiment, the composition comprises no more than 150 µg of genogroup II Norovirus VLPs. In still another embodiment, the composition comprises no more than 50 µg of genogroup II Norovirus VLPs. The Norovirus VLPs can be monovalent VLPs or multivalent VLPs.

In some aspects of the invention, genogroup I Norovirus VLPs in the vaccine compositions comprise a capsid protein derived from a genogroup I viral strain. In one embodiment, the genogroup I Norovirus VLPs comprise a capsid protein from a genogroup I, genotype 1 Norovirus. In another embodiment, the genogroup I Norovirus VLPs comprise a capsid protein from Norwalk virus. In other aspects of the invention, genogroup II Norovirus VLPs in the vaccine compositions comprise a capsid protein derived from a genogroup II viral strain. In some embodiments, the genogroup II Norovirus VLPs comprise a capsid protein from a genogroup II, genotype 4 Norovirus. In certain embodiments, the genogroup II Norovirus VLPs are VLPs generated from expression of a consensus sequence of genogroup II Norovirus. In one particular embodiment, the genogroup II Norovirus VLPs comprise a capsid protein having a sequence of SEQ ID NO: 1.

In certain embodiments, the vaccine composition further comprises at least one adjuvant. The adjuvant is preferably not a bacterial exotoxin adjuvant. In one embodiment, the adjuvant is a toll-like receptor agonist, such as monophosphoryl lipid A (MPL), flagellin, or CpG. In another embodiment, the adjuvant is aluminum hydroxide (e.g. alum). In certain embodiments, the vaccine composition comprises two adjuvants, such as MPL and aluminum hydroxide. In some embodiments, the vaccine composition may further comprise a buffer, such as L-histidine, imidazole, succinic acid, tris, and citric acid. The vaccine composition can be formulated as a dry powder or a liquid. In one embodiment, the vaccine composition is formulated as a liquid (e.g. aqueous formulation).

The intramuscular, bivalent Norovirus vaccine contained 5 µg each of a genogroup I.1 Norovirus VLP and a genogroup II.4 Norovirus VLP. The intranasal, monovalent vaccine contained 100 µg of a genogroup I.1 Norovirus. Volunteers receiving the intranasal vaccine or placebo were challenged with live Norovirus following the second immunization.

Figure 11A:
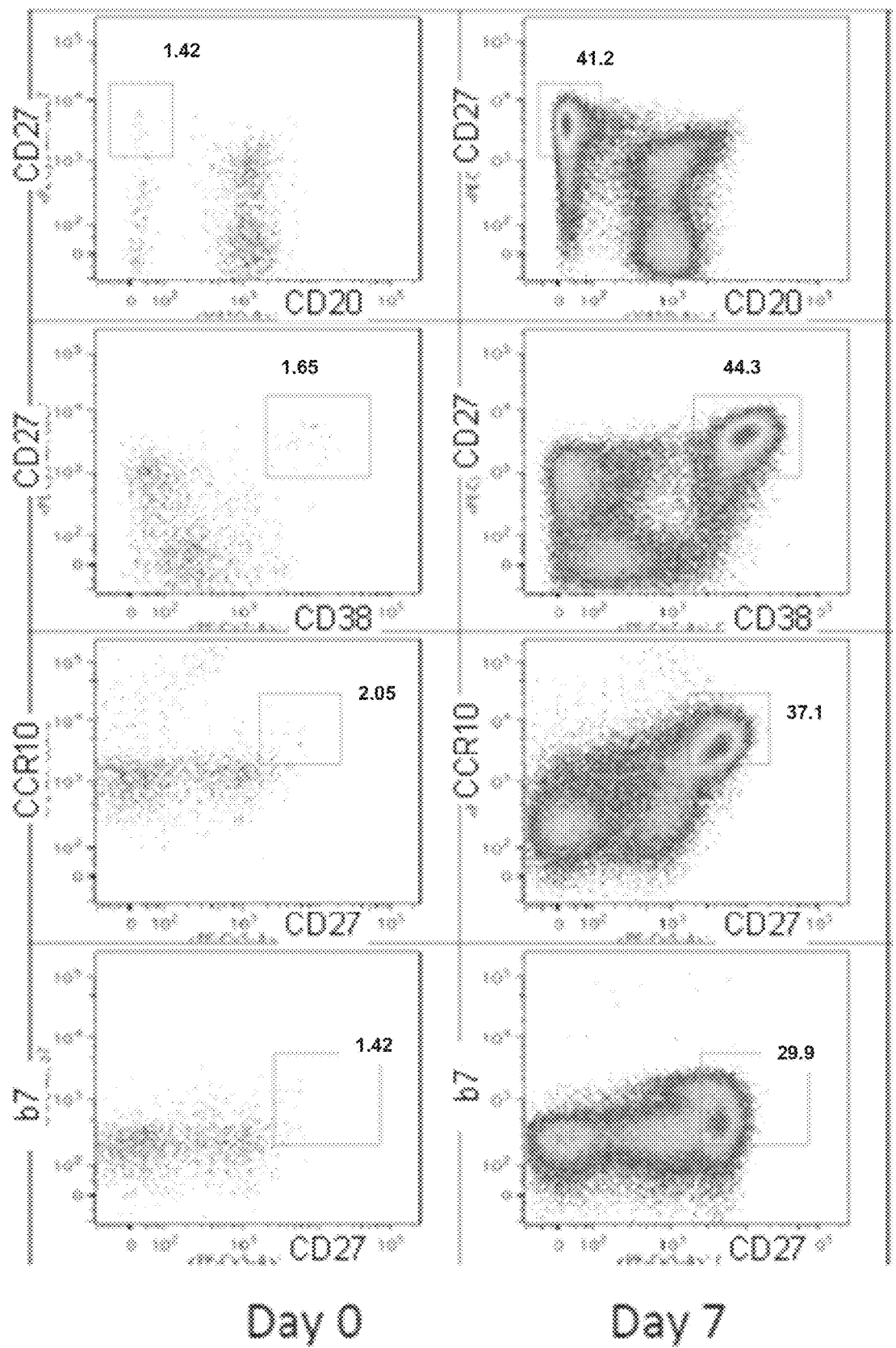
Figure 11B:
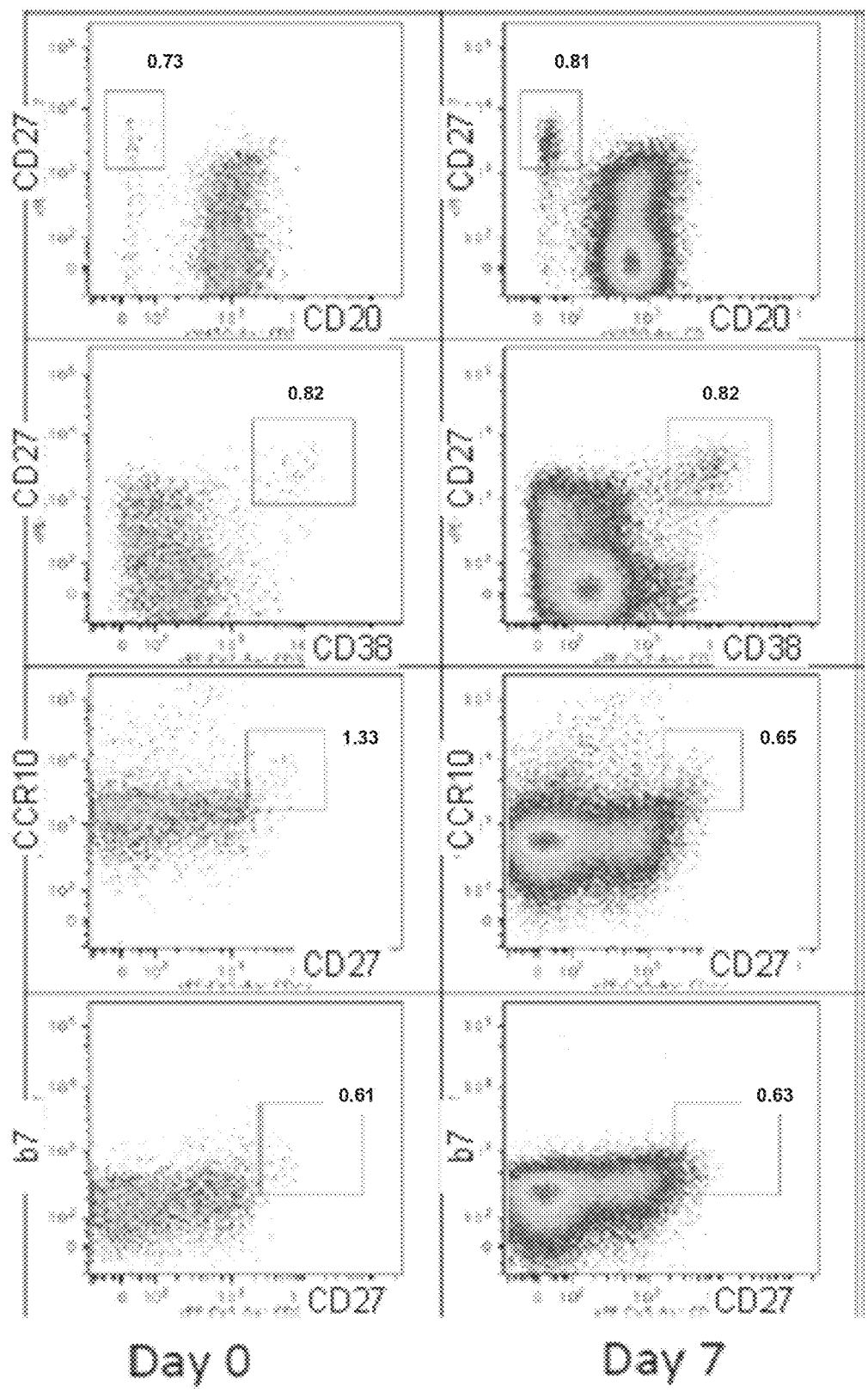

FIG. 11A-FIG. 11B. FACS analysis of peripheral blood mononuclear cells obtained from human volunteers on Day 0 prior to immunization with either a 5 µg dose of Norovirus intramuscular, bivalent vaccine (FIG. 11A) or placebo (FIG. 11B) and Day 7 post-immunization. CD19+ PBMC are mucosally targeted as evidenced of expression of alpha 4/beta7 homing receptor and chemokine CCR10 receptor.

DETAILED DESCRIPTION OF THE INVENTION

The present invention relates to methods of eliciting a protective immunity to Norovirus infections in a subject. In particular, the present invention provides methods of eliciting a protective immunity against Norovirus in a human by parenterally administering to the human no more than a single dose of a vaccine comprising Norovirus VLPs and optionally at least one adjuvant, wherein the vaccine confers protection from or amelioration of at least one symptom of Norovirus infection. The inventors have surprisingly discovered that intramuscular administration of no more than a single dose of a vaccine composition comprising Norovirus VLPs to humans induces a rapid (i.e. within 7 days of immunization) serum seroconversion (i.e. at least a three-fold increase in antigen-specific serum antibody titers above pre-vaccination levels) that is indicative of a protective immune response against Norovirus infection and illness. The immune responses induced by this single dose vaccine composition plateau at high antibody titers similar to that observed with natural infection by administration of live virus in human challenge studies. Interestingly, a boost dose of the vaccine is not required as the immune response is not increased upon further administration of an additional vaccine dose.

The invention provides a vaccine composition comprising one or more Norovirus antigens. By "Norovirus," "Norovirus (NOR)," "norovirus," and grammatical equivalents herein, are meant members of the genus Norovirus of the family Caliciviridae. In some embodiments, a Norovirus can include a group of related, positive-sense single-stranded RNA, nonenveloped viruses that can be infectious to human or non-human mammalian species. In some embodiments, a Norovirus can cause acute gastroenteritis in humans. Noroviruses also can be referred to as small round structured viruses (SRSVs) having a defined surface structure or ragged edge when viewed by electron microscopy.

Included within the Noroviruses are at least five genogroups (GI, GII, GIII, GIV, and GV). GI, GII, and GIV Noroviruses are infectious in humans, while GIII Noroviruses primarily infect bovine species. GV has recently been isolated from mice (Zheng et al. (2006) Virology, Vol 346: 312-323). Representative of GIII are the Jena and Newbury strains, while the Alphatron, Fort Lauderdale, and Saint Cloud strains are representative of GIV. The GI and GII groups may be further segregated into genetic clusters or genotypes based on genetic classification (Ando et al. (2000) J. Infectious Diseases, Vol. 181(Supp2):5336-5348; Lindell et al. (2005) J. Clin. Microbiol., Vol. 43(3): 1086-1092). As used herein, the term genetic clusters is used interchangeably with the term genotypes. Within genogroup I, there are 8 GI clusters known to date (with prototype virus strain name): GI.1 (Norwalk (NV-USA93)); GI.2 (Southhampton (SOV-GBR93)); GI.3 (Desert Shield (DSV-USA93)); GI.4 (Cruise Ship virus/Chiba (Chiba-JPN00)); GI.5 (318/Musgrove (Musgrov-GBR00)); GI.6 (Hesse (Hesse-DEU98)); GI.7 (Wnchest-GBR00); and GI.8 (Boxer-USA02). Within genogroup II, there are 19 GII clusters known to date (with prototype virus strain name): GII.1 (Hawaii (Hawaii-USA94)); GII.2 (Snow Mountain/Melksham (Msham-GBR95)); GII.3 (Toronto (Toronto-CAN93)); GII.4 (Bristol/Lordsdale (Bristol-GBR93)); GII.5 (290/Hillingdon (Hilingd-GBR00)); GII.6 (269/Seacroft (Seacrof-GBR00)); GII.7 (273/Leeds (Leeds-GBR00)); GII.8 (539/Amsterdam (Amstdam-NLD99)); GII.9 (378 (VABeach-USA01)), GII.10 (Erfurt-DEU01); GII.11 (SW9180JPN01); GII.12 (Wortley-GBR00); GII.13 (Faytvil-USA02); GII.14 (M7-USA03); GII.15 (J23-USA02); GII.16 (Tiffin-USA03); GII.17 (CSE1-USA03); GII.18 (QW101/2003/US) and GII.19 (QW170/2003/US).

By "Norovirus" also herein is meant recombinant Norovirus virus-like particles (rNOR VLPs). In some embodiments, recombinant expression of at least the Norovirus capsid protein encoded by ORF2 in cells, e.g., from a baculovirus vector in Sf9 cells, can result in spontaneous self-assembly of the capsid protein into VLPs. In some embodiments, recombinant expression of at least the Norovirus proteins encoded by ORF1 and ORF2 in cells, e.g., from a baculovirus vector in 519 cells, can result in spontaneous self-assembly of the capsid protein into VLPs. VLPs are structurally similar to Noroviruses but lack the viral RNA genome and therefore are not infectious. Accordingly, "Norovirus" includes virions that can be infectious or non-infectious particles, which include defective particles.

Non-limiting examples of Noroviruses include Norovirus genogroup 1 strain Hu/NoV/West Chester/2001/USA, GenBank Accession No. AY502016; Chiba virus (CHV, GenBank AB042808); Norovirus genogroup 2 strain Hu/NoV/Braddock Heights/1999/USA, GenBank Accession No. AY502015; Norovirus genogroup 2 strain Hu/NoV/Fayette/1999/USA, GenBank Accession No. AY502014; Norovirus genogroup 2 strain Hu/NoV/Fairfield/1999/USA, GenBank Accession No. AY502013; Norovirus genogroup 2 strain Hu/NoV/Sandusky/1999/USA, GenBank Accession No. AY502012; Norovirus genogroup 2 strain Hu/NoV/Canton/1999/USA, GenBank Accession No. AY502011; Norovirus genogroup 2 strain Hu/NoV/Tiffin/1999/USA, GenBank Accession No. AY502010; Norovirus genogroup 2 strain Hu/NoV/CS-E1/2002/USA, GenBank Accession No. AY50200; Norovirus genogroup 1 strain Hu/NoV/Wisconsin/2001/USA, GenBank Accession No. AY502008; Norovirus genogroup 1 strain Hu/NoV/CS-841/2001/USA, GenBank Accession No. AY502007; Norovirus genogroup 2 strain Hu/NoV/Hiram/2000/USA, GenBank Accession No. AY502006; Norovirus genogroup 2 strain Hu/NoV/Tontogany/1999/USA, GenBank Accession No. AY502005; Norwalk virus, complete genome, GenBank Accession No. NC.sub.-001959; Norovirus Hu/GI/Otofuke/1979/JP genomic RNA, complete genome, GenBank Accession No. AB187514; Norovirus Hu/Hokkaido/133/2003/JP, GenBank Accession No. AB212306; Norovirus Sydney 2212, GenBank Accession No. AY588132; Norwalk virus strain SN2000JA, GenBank Accession No. AB190457; Lordsdale virus complete genome, GenBank Accession No. X86557; Norwalk-like virus genomic RNA, Gifu'96, GenBank Accession No. AB045603; Norwalk virus strain Vietnam 026, complete genome, GenBank Accession No. AF504671; Norovirus Hu/GII.4/2004/NL, GenBank Accession No. AY883096; Norovirus Hu/GII/Hokushin/03/JP, GenBank Accession No. AB195227; Norovirus Hu/GII/Kamo/03/JP, GenBank Accession No. AB195228; Norovirus Hu/GII/Sinsiro/97/JP, GenBank Accession No. AB195226; Norovirus Hu/GII/Ina/02/JP, GenBank Accession No. AB 195225; Norovirus Hu/NLV/GII/Neustrelitz260/2000/DE, GenBank Accession No. AY772730; Norovirus Hu/NLV/Dresden174/pUS-NorII/1997/GE, GenBank Accession No. AY741811; Norovirus Hu/NLV/Oxford/B2S16/2002/UK, GenBank Accession No. AY587989; Norovirus Hu/NLV/Oxford/B4S7/2002/UK, GenBank Accession No. AY587987; Norovirus Hu/NLV/Witney/B7S2/2003/UK, GenBank Accession No. AY588030; Norovirus Hu/NLV/Banbury/B9S23/2003/UK, GenBank Accession No. AY588029; Norovirus Hu/NLV/ChippingNorton/2003/UK, GenBank Accession No. AY588028; Norovirus Hu/NLV/Didcot/B9S2/2003/UK, GenBank Accession No. AY588027; Norovirus Hu/NLV/Oxford/B8S5/2002/UK, GenBank Accession No. AY588026; Norovirus Hu/NLV/Oxford/B6S4/2003/UK, GenBank Accession No. AY588025; Norovirus Hu/NLV/Oxford/B6S5/2003/UK, GenBank Accession No. AY588024; Norovirus Hu/NLV/Oxford/B5S23/2003/UK, GenBank Accession No. AY588023; Norovirus Hu/NLV/Oxford/B6S2/2003/UK, GenBank Accession No. AY588022; Norovirus Hu/NLV/Oxford/B6S6/2003/UK, GenBank Accession No. AY588021; Norwalk-like virus isolate Bo/Thirsk10/00/UK, GenBank Accession No. AY126468; Norwalk-like virus isolate Bo/Penrith55/00/UK, GenBank Accession No. AY126476; Norwalk-like virus isolate Bo/Aberystwyth24/00/UK, GenBank Accession No. AY126475; Norwalk-like virus isolate Bo/Dumfries/94/UK, GenBank Accession No. AY126474; Norovirus NLV/IF2036/2003/Iraq, GenBank Accession No. AY675555; Norovirus NLV/IF1998/2003/Iraq, GenBank Accession No. AY675554; Norovirus NLV/BUDS/2002/USA, GenBank Accession No. AY660568; Norovirus NLV/Paris Island/2003/USA, GenBank Accession No. AY652979; Snow Mountain virus, complete genome, GenBank Accession No. AY134748; Norwalk-like virus NLV/Fort Lauderdale/560/1998/US, GenBank Accession No. AF414426; Hu/Norovirus/hiroshima/1999/JP(9912-02F), GenBank Accession No. AB044366; Norwalk-like virus strain 11MSU-MW, GenBank Accession No. AY274820; Norwalk-like virus strain B-1SVD, GenBank Accession No. AY274819; Norovirus genogroup 2 strain Hu/NoV/Farmington Hills/2002/USA, GenBank Accession No. AY502023; Norovirus genogroup 2 strain Hu/NoV/CS-G4/2002/USA, GenBank Accession No. AY502022; Norovirus genogroup 2 strain Hu/NoV/CS-G2/2002/USA, GenBank Accession No. AY502021; Norovirus genogroup 2 strain Hu/NoV/CS-G12002/USA, GenBank Accession No. AY502020; Norovirus genogroup 2 strain Hu/NoV/Anchorage/2002/USA, GenBank Accession No. AY502019; Norovirus genogroup 2 strain Hu/NoV/CS-D1/2002/CAN, GenBank Accession No. AY502018; Norovirus genogroup 2 strain Hu/NoV/Germanton/2002/USA, GenBank Accession No. AY502017; Human calicivirus NLV/GII/Langen1061/2002/DE, complete genome, GenBank Accession No. AY485642; Murine norovirus 1 polyprotein, GenBank Accession No. AY228235; Norwalk virus, GenBank Accession No. AB067536; Human calicivirus NLV/Mex7076/1999, GenBank Accession No. AF542090; Human calicivirus NLV/Oberhausen 455/01/DE, GenBank Accession No. AF539440; Human calicivirus NLV/Herzberg 385/01/DE, GenBank Accession No. AF539439; Human calicivirus NLV/Boxer/2001/US, GenBank Accession No. AF538679; Norwalk-like virus genomic RNA, complete genome, GenBank Accession No. AB081723; Norwalk-like virus genomic RNA, complete genome, isolate:Saitama U201, GenBank Accession No. AB039782; Norwalk-like virus genomic RNA, complete genome, isolate:Saitama U18, GenBank Accession No. AB039781; Norwalk-like virus genomic RNA, complete genome, isolate: Saitama U25, GenBank Accession No. AB039780; Norwalk virus strain:U25G11, GenBank Accession No. AB067543; Norwalk virus strain:U201 GII, GenBank Accession No. AB067542; Norwalk-like viruses strain 416/97003156/1996/LA, GenBank Accession No. AF080559; Norwalk-like viruses strain 408/97003012/1996/FL, GenBank Accession No. AF080558; Norwalk-like virus NLV/Burwash Landing/331/1995/US, GenBank Accession No. AF414425; Norwalk-like virus NLV/Miami Beach/326/1995/US, GenBank Accession No. AF414424; Norwalk-like virus NLV/White River/290/1994/US, GenBank Accession No. AF414423; Norwalk-like virus NLV/New Orleans/306/1994/US, GenBank Accession No. AF414422; Norwalk-like virus NLV/Port Canaveral/301/1994/US, GenBank Accession No. AF414421; Norwalk-like virus NLV/Honolulu/314/1994/US, GenBank Accession No. AF414420; Norwalk-like virus NLV/Richmond/283/1994/US, GenBank Accession No. AF414419; Norwalk-like virus NLV/Westover/302/1994/US, GenBank Accession No. AF414418; Norwalk-like virus NLV/UK3-17/12700/1992/GB, GenBank Accession No. AF414417; Norwalk-like virus NLV/Miami/81/1986/US, GenBank Accession No. AF414416; Snow Mountain strain, GenBank Accession No. U70059; Desert Shield virus DSV395, GenBank Accession No. U04469; Norwalk virus, complete genome, GenBank Accession No. AF093797; Hawaii calicivirus, GenBank Accession No. U07611; Southampton virus, GenBank Accession No. L07418; Norwalk virus (SRSV-KY-89/89/J), GenBank Accession No. L23828; Norwalk virus (SRSV-SMA/76/US), GenBank Accession No. L23831; Camberwell virus, GenBank Accession No. U46500; Human calicivirus strain Melksham, GenBank Accession No. X81879; Human calicivirus strain MX, GenBank Accession No. U22498; Minireovirus TV24, GenBank Accession No. U02030; and Norwalk-like virus NLV/Gnedd/273/1994/US, GenBank Accession No. AF414409; sequences of all of which (as entered by the date of filing of this application) are herein incorporated by reference. Additional Norovirus sequences are disclosed in the following patent publications: WO 2005/030806, WO 2000/79280, JP2002020399, US2003129588, U.S. Pat. No. 6,572,862, WO 1994/05700, and WO 05/032457, all of which are herein incorporated by reference in their entireties. See also Green et al. (2000) J. Infect. Dis., Vol. 181(Suppl. 2):S322-330; Wang et al. (1994) J. Virol., Vol. 68:5982-5990; Chen et al. (2004) J. Virol., Vol. 78: 6469-6479; Chakravarty et al. (2005) J. Virol., Vol. 79: 554-568; Hansman et al. (2006) J. Gen. Virol., Vol. 87:909-919; Bull et al. (2006) J. Clin. Micro., Vol. 44(2):327-333; Siebenga, et al. (2007) J. Virol., Vol. 81(18):9932-9941, and Fankhauser et al. (1998) J. Infect. Dis., Vol. 178:1571-1578; for sequence comparisons and a discussion of genetic diversity and phylogenetic analysis of Noroviruses. The nucleic acid and corresponding amino acid sequences of each are all incorporated by reference in their entirety. In some embodiments, a cryptogram can be used for identification purposes and is organized: host species from which the virus was isolated/genus abbreviation/species abbreviation/strain name/year of occurrence/country of origin. (Green et al., Human Caliciviruses, in Fields Virology Vol. 1 841-874 (Knipe and Howley, editors-in-chief, 4th ed., Lippincott Williams & Wilkins 2001)). Genogroup II, genotype 4 (GII.4) viral strains (e.g., Houston, Minerva (also known as Den Haag), and Laurens (also known as Yerseke) strains) are preferred in some embodiments. As new strains are identified and their genetic sequences are made available, one skilled in the art would be able to employ VLPs using these contemporary strains in the compositions and methods of the present invention using ordinary skill. Thus, the present invention contemplates VLPs made from such strains as suitable antigens for use in the compositions and methods described herein.

The Norovirus antigen may be in the form of peptides, proteins, or virus-like particles (VLPs). In a preferred embodiment, the Norovirus antigen comprises VLPs. As used herein, "virus-like particle(s) or VLPs" refer to a virus-like particle(s), fragment(s), aggregates, or portion(s) thereof produced from the capsid protein coding sequence of Norovirus and comprising antigenic characteristic(s) similar to those of infectious Norovirus particles. Norovirus antigens may also be in the form of capsid monomers, capsid multimers, protein or peptide fragments of VLPs, or aggregates or mixtures thereof. The Norovirus antigenic proteins or peptides may also be in a denatured form, produced using methods known in the art.

The VLPs of the present invention can be formed from either the full length Norovirus capsid protein such as VP1 and/or VP2 proteins or certain VP1 or VP2 derivatives using standard methods in the art. Alternatively, the capsid protein used to form the VLP is a truncated capsid protein. In some embodiments, for example, at least one of the VLPs comprises a truncated VP1 protein. In other embodiments, all the VLPs comprise truncated VP1 proteins. The truncation may be an N- or C-terminal truncation. Truncated capsid proteins are suitably functional capsid protein derivatives. Functional capsid protein derivatives are capable of raising an immune response (if necessary, when suitably adjuvanted) in the same way as the immune response is raised by a VLP consisting of the full length capsid protein.

VLPs may contain major VP1 proteins and/or minor VP2 proteins. In some embodiments, each VLP contains VP1 and/or VP2 protein from only one Norovirus genogroup giving rise to a monovalent VLP. As used herein, the term "monovalent" means the antigenic proteins are derived from a single Norovirus genogroup. For example, the VLPs contain VP1 and/or VP2 from a virus strain of genogroup I (e.g., VP1 and VP2 from Norwalk virus). Preferably the VLP is comprised of predominantly VP1 proteins. In one embodiment of the invention, the antigen is a mixture of monovalent VLPs wherein the composition includes VLPs comprised of VP1 and VP2 from a single Norovirus genogroup mixed with VLPs comprised of VP1 and VP2 from a different Norovirus genogroup (e.g. Norwalk virus and Houston virus) taken from multiple viral strains. Purely by way of example the composition can contain monovalent VLPs from one or more strains of Norovirus genogroup I together with monovalent VLPs from one or more strains of Norovirus genogroup II. Strains may be selected based on their predominance of circulation at a given time. In certain embodiments, the Norovirus VLP mixture is composed of GI.1 and GII.4 viral strains. More preferably, the Norovirus VLP mixture is composed of the strains of Norwalk and a consensus capsid sequence derived from genogroup II Noroviruses. Consensus capsid sequences derived from circulating Norovirus sequences and VLPs made with such sequences are described in WO 2010/017542, which is herein incorporated by reference in its entirety. For instance, in one embodiment, a consensus capsid sequence derived from genogroup II, genotype 4 (GII.4) viral strains comprises a sequence of SEQ ID NO: 1. Thus, in some embodiments, the vaccine composition comprises a mixture of monovalent VLPs, wherein one monovalent VLP comprises a capsid protein from a genogroup I Norovirus (e.g. Norwalk) and the other monovalent VLP comprises a consensus capsid protein comprising a sequence of SEQ ID NO: 1.

```
                                                                  (SEQ ID NO: 1)
M K M A S S D A N P S D G S T A N L V P E V N N E V M A L E P V

V G A A I A A P V A G Q Q N V I D P W I R N N F V Q A P G G E F

T V S P R N A P G E I L W S A P L G P D L N P Y L S H L A R M Y

N G Y A G G F E V Q V I L A G N A F T A G K I I F A A V P P N F

P T E G L S P S Q V T M F P H I I V D V R Q L E P V L I P L P D

V R N N F Y H Y N Q S N D P T I K L I A M L Y T P L R A N N A G

D D V F T V S C R V L T R P S P D F D F I F L V P P T V E S R T

K P F T V P I L T V E E M T N S R F P I P L E K L F T G P S G A

F V V Q P Q N G R C T T D G V L L G T T Q L S P V N I C T F R G

D V T H I A G T Q E Y T M N L A S Q N W N N Y D P T E E I P A P

L G T P D F V G K I Q G V L T Q T T R G D G S T R G H K A T V S

T G S V H F T P K L G S V Q F S T D T S N D F E T G Q N T K F T

P V G V V Q D G S T T H Q N E P Q Q W V L P D Y S G R D S H N V

H L A P A V A P T F P G E Q L L F F R S T M P G C S G Y P N M N

L D C L L P Q E W V Q H F Y Q E A A P A Q S D V A L L R F V N P

D T G R V L F E C K L H K S G Y V T V A H T G Q H D L V I P P N

G Y F R F D S W V N Q F Y T L A P M G N G T G R R R A L
```

However, in an alternative embodiment of the invention, the VLPs may be multivalent VLPs that comprise, for example, VP1 and/or VP2 proteins from one Norovirus genogroup intermixed with VP1 and/or VP2 proteins from a second Norovirus genogroup, wherein the different VP1 and VP2 proteins are not chimeric VP1 and VP2 proteins, but associate together within the same capsid structure to form immunogenic VLPs. As used herein, the term "multivalent" means that the antigenic proteins are derived from two or more Norovirus genogroups or strains. Multivalent VLPs may contain VLP antigens taken from two or more viral strains. Purely by way of example the composition can contain multivalent VLPs comprised of capsid monomers or multimers from one or more strains of Norovirus genogroup I (e.g. Norwalk virus) together with capsid monomers or multimers from one or more strains of Norovirus genogroup II (e.g. Houston virus). Preferably, the multivalent VLPs contain capsid proteins from the strains of Norwalk and Houston Noroviruses, or other predominantly circulating strains at a given time.

The combination of monovalent or multivalent VLPs within the composition preferably would not reduce the immunogenicity of each VLP type. In particular it is preferred that there is no interference between Norovirus VLPs in the combination of the invention, such that the combined VLP composition of the invention is able to elicit immunity against infection by each Norovirus genotype represented in the vaccine. Suitably the immune response against a given VLP type in the combination is at least 50% of the immune response of that same VLP type when measured individually, preferably 100% or substantially 100%. The immune response may suitably be measured, for example, by antibody responses, as illustrated in the examples herein.

As used herein, "genogroup I Norovirus VLPs" refer to either monovalent or multivalent VLPs that comprise a capsid protein derived from one or more genogroup I Norovirus strains. In some embodiments, genogroup I Norovirus VLPs comprise a full length capsid protein from a genogroup I Norovirus (e.g. Norwalk virus). In other embodiments, genogroup I Norovirus VLPs comprise a consensus capsid protein derived from various genogroup I strains. The genogroup I strains from which the consensus capsid sequence is derived can be within the same genotype or genetic cluster or from different genotypes or genetic clusters. Similarly, as used herein, "genogroup II Norovirus VLPs" refer to either monovalent or multivalent VLPs that comprise a capsid protein derived from one or more genogroup II Norovirus strains. In some embodiments, genogroup II Norovirus VLPs comprise a full length capsid protein from a genogroup II Norovirus (e.g. Laurens or Minerva virus). In other embodiments, genogroup II Norovirus VLPs comprise a consensus capsid protein derived from various genogroup II strains. The genogroup II strains from which the consensus capsid sequence is derived can be within the same genotype or genetic cluster or from different genotypes or genetic clusters. In one embodiment, the genogroup II Norovirus VLPs comprise a capsid consensus sequence of genogroup II, genotype 4 (GII.4) Norovirus. Thus, in some embodiments, the genogroup II Norovirus VLPs comprise a capsid sequence of SEQ ID NO: 1.

Multivalent VLPs may be produced by separate expression of the individual capsid proteins followed by combination to form VLPs. Alternatively multiple capsid proteins may be expressed within the same cell, from one or more DNA constructs. For example, multiple DNA constructs may be transformed or transfected into host cells, each vector encoding a different capsid protein. Alternatively a single vector having multiple capsid genes, controlled by a shared promoter or multiple individual promoters, may be used. IRES elements may also be incorporated into the vector, where appropriate. Using such expression strategies, the co-expressed capsid proteins may be co-purified for subsequent VLP formation, or may spontaneously form multivalent VLPs which can then be purified.

A preferred process for multivalent VLP production comprises preparation of VLP capsid proteins or derivatives, such as VP1 proteins, from different Norovirus genotypes, mixing the proteins, and assembly of the proteins to produce multivalent VLPs. The VP1 proteins may be in the form of a crude extract, be partially purified or purified prior to mixing. Assembled monovalent VLPs of different genogroups may be disassembled, mixed together and reassembled into multivalent VLPs. Preferably the proteins or VLPs are at least partially purified before being combined. Optionally, further purification of the multivalent VLPs may be carried out after assembly.

Suitably the VLPs of the invention are made by disassembly and reassembly of VLPs, to provide homogenous and pure VLPs. In one embodiment multivalent VLPs may be made by disassembly of two or more VLPs, followed by combination of the disassembled VLP components at any suitable point prior to reassembly. This approach is suitable when VLPs spontaneously form from expressed VP1 protein, as occurs for example, in some yeast strains. Where the expression of the VP1 protein does not lead to spontaneous VLP formation, preparations of VP1 proteins or capsomers may be combined before assembly into VLPs.

Where multivalent VLPs are used, preferably the components of the VLPs are mixed in the proportions in which they are desired in the final mixed VLP. For example, a mixture of the same amount of a partially purified VP1 protein from Norwalk and Houston viruses (or other Norovirus strains) provides a multivalent VLP with approximately equal amounts of each protein.

Compositions comprising multivalent VLPs may be stabilized by solutions known in the art, such as those of WO 98/44944, WO 00/45841, incorporated herein by reference.

Compositions of the invention may comprise other proteins or protein fragments in addition to Norovirus VP1 and VP2 proteins or derivatives. Other proteins or peptides may also be co-administered with the composition of the invention. Optionally the composition may also be formulated or co-administered with non-Norovirus antigens. Suitably these antigens can provide protection against other diseases.

The VP1 protein or functional protein derivative is suitably able to form a VLP, and VLP formation can be assessed by standard techniques such as, for example, size exclusion chromatography, electron microscopy and dynamic laser light scattering.

The antigenic molecules of the present invention can be prepared by isolation and purification from the organisms in which they occur naturally, or they may be prepared by recombinant techniques. Preferably the Norovirus VLP antigens are prepared from insect cells such as S19 or H5 cells, although any suitable cells such as E. coli or yeast cells, for example, S. cerevisiae, S. pombe, Pichia pastori or other Pichia expression systems, mammalian cell expression such as CHO or HEK systems may also be used. When prepared by a recombinant method or by synthesis, one or more insertions, deletions, inversions or substitutions of the amino acids constituting the peptide may be made. Each of the aforementioned antigens is preferably used in the substantially pure state.

The procedures of production of norovirus VLPs in insect cell culture have been previously disclosed in U.S. Pat. No. 6,942,865, which is incorporated herein by reference in its entirety. Briefly, a cDNA from the 3' end of the genome containing the viral capsid gene (ORF2) and a minor structural gene (ORF3) is cloned. The recombinant baculoviruses carrying the viral capsid genes is constructed from the cloned cDNAs. Norovirus VLPs are produced in S19 or H5 insect cell cultures.

In some embodiments, the vaccine composition comprises one or more adjuvants in combination with the Norovirus antigen. Most adjuvants contain a substance designed to protect the antigen from rapid catabolism, such as aluminum hydroxide or mineral oil, and a stimulator of immune responses, such as *Bordatella pertussis* or *Mycobacterium tuberculosis* derived proteins. Suitable adjuvants are commercially available as, for example, Freund's Incomplete Adjuvant and Complete Adjuvant (Pifco Laboratories, Detroit, Mich.); Merck Adjuvant 65 (Merck and Company, Inc., Rahway, N.J.); aluminum salts such as aluminum hydroxide gel (alum) or aluminum phosphate; salts of calcium, iron or zinc; an insoluble suspension of acylated tyrosine acylated sugars; cationically or anionically derivatized polysaccharides; polyphosphazenes; biodegradable microspheres; and Quil A.

Suitable adjuvants also include, but are not limited to, toll-like receptor (TLR) agonists, particularly toll-like receptor type 4 (TLR-4) agonists (e.g., monophosphoryl lipid A (MPL), synthetic lipid A, lipid A mimetics or analogs), aluminum salts, cytokines, saponins, muramyl dipeptide (MDP) derivatives, CpG oligos, lipopolysaccharide (LPS) of gram-negative bacteria, polyphosphazenes, emulsions, virosomes, cochleates, poly(lactide-co-glycolides) (PLG) microparticles, poloxamer particles, microparticles, liposomes, oil-in-water emulsions, MF59, and squalene. In some embodiments, the adjuvants are not bacterially-derived exotoxins. Preferred adjuvants include adjuvants which stimulate a Th1 type response such as 3DMPL or QS21.

Monophosphoryl Lipid A (MPL), a non-toxic derivative of lipid A from *Salmonella*, is a potent TLR-4 agonist that has been developed as a vaccine adjuvant (Evans et al. 2003). In pre-clinical murine studies intranasal MPL has been shown to enhance secretory, as well as systemic, humoral responses (Baldridge et al. 2000; Yang et al. 2002). It has also been proven to be safe and effective as a vaccine adjuvant in clinical studies of greater than 120,000 patients (Baldrick et al., 2002; Baldridge et al. 2004). MPL stimulates the induction of innate immunity through the TLR-4 receptor and is thus capable of eliciting nonspecific immune responses against a wide range of infectious pathogens, including both gram negative and gram positive bacteria, viruses, and parasites (Baldridge et al. 2004; Persing et al. 2002). Inclusion of MPL in vaccine formulations should provide rapid induction of innate responses, eliciting non-specific immune responses from viral challenge while enhancing the specific responses generated by the antigenic components of the vaccine.

In one embodiment, the present invention provides a composition comprising monophosphoryl lipid A (MPL) or 3 De-O-acylated monophosphoryl lipid A (3D-MPL) as an enhancer of adaptive and innate immunity. Chemically 3D-MPL is a mixture of 3 De-O-acylated monophosphoryl lipid A with 4, 5 or 6 acylated chains. A preferred form of 3 De-O-acylated monophosphoryl lipid A is disclosed in European Patent 0 689 454 B1 (SmithKline Beecham Biologicals SA), which is incorporated herein by reference. In another embodiment, the present invention provides a composition comprising synthetic lipid A, lipid A mimetics or analogs, such as BioMira's PET Lipid A, or synthetic derivatives designed to function like TLR-4 agonists.

In certain embodiments, the vaccine composition comprises two adjuvants. A combination of adjuvants may be selected from those described above. In one particular embodiment, the two adjuvants are MPL and aluminum hydroxide (e.g., alum). In another particular embodiment, the two adjuvants are MPL and oil.

The term "effective adjuvant amount" or "effective amount of adjuvant" will be well understood by those skilled in the art, and includes an amount of one or more adjuvants which is capable of stimulating the immune response to an administered antigen, i.e., an amount that increases the immune response of an administered antigen composition, as measured in terms of the IgA levels in the nasal washings, serum IgG or IgM levels, or B and T-Cell proliferation. Suitably effective increases in immunoglobulin levels include by more than 5%, preferably by more than 25%, and in particular by more than 50%, as compared to the same antigen composition without any adjuvant.

In one embodiment, the present invention provides a vaccine composition formulated for parenteral administration, wherein the composition includes at least two types of Norovirus VLPs in combination with aluminum hydroxide and a buffer. The buffer can be selected from the group consisting of L-histidine, imidazole, succinic acid, tris, citric acid, bis-tris, pipes, mes, hepes, glycine amide, and tricine. In one embodiment, the buffer is L-histidine or imidazole. Preferably, the buffer is present in a concentration from about 15 mM to about 50 mM, more preferably from about 18 mM to about 40 mM, or most preferably about 20 mM to about 25 mM. In some embodiments, the pH of the antigenic or vaccine composition is from about 6.0 to about 7.0, or from about 6.2 to about 6.8, or about 6.5. The vaccine composition can be an aqueous formulation. In some embodiments, the vaccine composition is a lyophilized powder and reconstituted to an aqueous formulation.

In certain embodiments, the vaccine composition further comprises at least one adjuvant in addition to the two or more types of Norovirus VLPs, aluminum hydroxide, and a buffer. For instance, the adjuvant can be a toll-like receptor agonist, such as MPL, flagellin, CpG oligos, synthetic lipid A or lipid A mimetics or analogs. In one particular embodiment, the adjuvant is MPL.

The Norovirus VLPs included in the vaccine compositions of the invention can be any of the VLPs described herein. In one embodiment, the two types of Norovirus VLPs each comprise a capsid protein from different genogroups (e.g., genogroup I and genogroup II). For instance, one type of Norovirus VLP comprises a capsid protein derived from a genogroup I Norovirus and the other type of Norovirus VLP comprises a capsid protein derived from a genogroup II Norovirus. In one embodiment, one type of Norovirus VLP comprises a capsid protein from Norwalk virus and the other type of Norovirus VLP comprises a consensus capsid protein derived from genogroup II, genotype 4 Noroviruses (e.g., a capsid protein comprising a sequence of SEQ ID NO: 1). The vaccine composition can comprise about 5 µg to about 200 µg of each Norovirus VLP, more preferably about 15 µg to about 50 µg of each Norovirus VLP. In some embodiments, the dose of one type of Norovirus VLP is different than the dose of the other type of Norovirus VLP. For instance, in certain embodiments, the vaccine composition comprises about 5 µg to about 15 µg of a genogroup I VLP and about 15 µg to about 50 µg of a genogroup II VLP. In other embodiments, the vaccine composition comprises about 15 µg to about 50 µg of a genogroup I VLP and about 50 µg to about 150 µg of a genogroup II VLP.

In some embodiments, the vaccine compositions further comprise a pharmaceutically acceptable salt, including, but not limited to, sodium chloride, potassium chloride, sodium sulfate, ammonium sulfate, and sodium citrate. In one embodiment, the pharmaceutically acceptable salt is sodium chloride. The concentration of the pharmaceutically acceptable salt can be from about 10 mM to about 200 mM, with preferred concentrations in the range of from about 100 mM to about 150 mM. Preferably, the vaccine compositions of the invention contain less than 2 mM of free phosphate. In some embodiments, the vaccine compositions comprise less than 1 mM of free phosphate. The vaccine compositions may also further comprise other pharmaceutically acceptable excipients, such as sugars (e.g., sucrose, trehalose, mannitol) and surfactants.

As discussed herein, the compositions of the invention can be formulated for administration as vaccines formulations. As used herein, the term "vaccine" refers to a formulation which contains Norovirus VLPs or other Norovirus antigens of the present invention as described above, which is in a form that is capable of being administered to a vertebrate, particularly a human, and which induces a protective immune response sufficient to induce immunity to prevent and/or ameliorate a Norovirus infection or Norovirus-induced illness and/or to reduce at least one symptom of a Norovirus infection or illness.

As used herein, the term "immune response" refers to both the humoral immune response and the cell-mediated immune response. The humoral immune response involves the stimulation of the production of antibodies by B lymphocytes that, for example, neutralize infectious agents, block infectious agents from entering cells, block replication of said infectious agents, and/or protect host cells from infection and destruction. The cell-mediated immune response refers to an immune response that is mediated by T-lymphocytes and/or other cells, such as macrophages, against an infectious agent, exhibited by a vertebrate (e.g., a human), that prevents or ameliorates infection or reduces at least one symptom thereof. In particular, "protective immunity" or "protective immune response" refers to immunity or eliciting an immune response against an infectious agent, which is exhibited by a vertebrate (e.g., a human), that prevents or ameliorates an infection or reduces at least one symptom thereof. Specifically, induction of a protective immune response from administration of the vaccine is evident by elimination or reduction of the presence of one or more symptoms of acute gastroenteritis or a reduction in the duration or severity of such symptoms. Clinical symptoms of gastroenteritis from Norovirus include nausea, diarrhea, loose stool, vomiting, fever, and general malaise. A protective immune response that reduces or eliminates disease symptoms will reduce or stop the spread of a Norovirus outbreak in a population. Vaccine preparation is generally described in Vaccine Design ("The subunit and adjuvant approach" (eds Powell M. F. & Newman M. J.) (1995) Plenum Press New York). The compositions of the present invention can be formulated, for example, for delivery to one or more of the oral, gastro-intestinal, and respiratory (e.g. nasal) mucosa. The compositions of the present invention can be formulated, for example, for delivery by injection, such as parenteral injection (e.g., intravenous, subcutaneous, intradermal, or intramuscular injection).

Where the composition is intended for delivery to the respiratory (e.g. nasal) mucosa, typically it is formulated as an aqueous solution for administration as an aerosol or nasal drops, or alternatively, as a dry powder, e.g. for rapid deposition within the nasal passage. Compositions for administration as nasal drops may contain one or more excipients of the type usually included in such compositions, for example preservatives, viscosity adjusting agents, tonicity adjusting agents, buffering agents, and the like. Viscosity agents can be microcrystalline cellulose, chitosan, starches, polysaccharides, and the like. Compositions for administration as dry powder may also contain one or more excipients usually included in such compositions, for example, mucoadhesive agents, bulking agents, and agents to deliver appropriate powder flow and size characteristics. Bulking and powder flow and size agents may include mannitol, sucrose, trehalose, and xylitol.

Where the composition is intended for parenteral injection, such as intravenous (i.v.), subcutaneous (s.c.), intradermal, or intramuscular (i.m.) injection, it is typically formulated as a liquid suspension (i.e. aqueous formulation) comprised of at least one type of Norovirus VLP and optionally at least one adjuvant. In one embodiment, the adjuvant may be MPL. In another embodiment, liquid vaccine formulated for parenteral administration may have more than one adjuvant. In a preferred embodiment, a parenterally-formulated (e.g., i.m., i.v., or s.c.-formulated) liquid vaccine comprises Norovirus genogroup I and/or genogroup II VLPs with aluminum hydroxide (e.g. alum) and monophosphoryl lipid A (MPL) as adjuvants. In one embodiment, a liquid formulation for parenteral administration comprises Norovirus genogroup antigen(s), such as one or more types of Norovirus VLPs as described herein, MPL, aluminum hydroxide, and a buffer. In another embodiment, a liquid formulation for parenteral administration comprises Norovirus genogroup antigen(s), MPL, oil, and a buffer. In certain embodiments, the buffer in the parenteral vaccine formulations is L-histidine or imidazole. Parenteral administration of liquid vaccines can be by needle and syringe, as is well known in the art.

In certain embodiments, a vaccine composition of the invention for eliciting a protective immune response against Norovirus in humans comprises genogroup I and/or genogroup II Norovirus VLPs at a dose of no more than 150 µg. For instance, in some embodiments, the vaccine composition comprises no more than 150 µg, no more than 100 µg, no more than 50 µg, no more than 25 µg, no more than 15 µg, or no more than 10 µg of genogroup I Norovirus VLPs. In other embodiments, the vaccine composition comprises no more than 150 µg, no more than 100 µg, no more than 50 µg, no more than 25 µg, no more than 15 µg, or no more than 10 µg of genogroup II Norovirus VLPs. In certain embodiments, the vaccine composition comprises no more than 150 µg of each genogroup I and genogroup II Norovirus VLPs. In such embodiments, the dose of genogroup I Norovirus VLPs and genogroup II VLPs can be the same or different. For instance, in one embodiment, the vaccine composition may comprise no more than 50 µg of genogroup I Norovirus VLPs and no more than 150 µg of genogroup II Norovirus VLPs. In another embodiment, the vaccine composition may comprise no more than 25 µg of genogroup I Norovirus VLPs and no more than 50 µg of genogroup II Norovirus VLPs. In other embodiments, the vaccine composition may comprise no more than 15 µg of genogroup I Norovirus VLPs and no more than 50 µg of genogroup II Norovirus VLPs. In still other embodiments, the vaccine composition may comprise no more than 25 µg of genogroup I Norovirus VLPs and no more than 150 µg of genogroup II Norovirus VLPs.

The genogroup I and genogroup II Norovirus VLPs can be derived from any of the Norovirus strains described herein. In one embodiment, the genogroup I Norovirus VLPs are genogroup I, genotype 1 (GI.1) VLPs (i.e. comprise a capsid protein from a GI.1 Norovirus). In another embodiment, the genogroup I Norovirus VLPs are Norwalk VLPs. In another embodiment, the genogroup II Norovirus VLPs are genogroup II, genotype 4 (GII.4) VLPs. In still another embodiment, the genogroup II Norovirus VLPs are VLPs generated from expression of a consensus sequence of genogroup II Norovirus. In a particular embodiment, the genogroup II Norovirus VLPs comprise a capsid protein having a sequence of SEQ ID NO: 1.

The vaccine compositions hereinbefore described may be lyophilized and stored anhydrous until they are ready to be used, at which point they are reconstituted with diluent. Alternatively, different components of the composition may be stored separately in a kit (any or all components being lyophilized). The components may remain in lyophilized form for dry formulation or be reconstituted for liquid formulations, and either mixed prior to use or administered separately to the patient. In some embodiments, the vaccine compositions are stored in kits in liquid formulations and may be accompanied by delivery devices, such as syringes equipped with needles. In other embodiments, the liquid vaccine compositions may be stored within the delivery devices in a kit. For example, a kit may comprise pre-filled syringes, autoinjectors, or injection pen devices containing a liquid formulation of a vaccine composition described herein.

The lyophilization of vaccines is well known in the art. Typically the liquid antigen is freeze dried in the presence of agents to protect the antigen during the lyophilization process and to yield a cake with desirable powder characteristics. Sugars such as sucrose, mannitol, trehalose, or lactose (present at an initial concentration of 10-200 mg/mL) are commonly used for cryoprotection of protein antigens and to yield lyophilized cake with desirable powder characteristics. Lyophilizing the compositions theoretically results in a more stable composition.

The amount of antigen in each vaccine composition is selected as an amount which induces a robust immune response without significant, adverse side effects. Such amount will vary depending upon which specific antigen(s) is employed, route of administration, and adjuvants used. In general, the dose administered to a patient, in the context of the present invention should be sufficient to effect a protective immune response in the patient over time, or to induce the production of antigen-specific antibodies. Thus, the composition is administered to a patient in an amount sufficient to elicit an immune response to the specific antigens and/or to prevent, alleviate, reduce, or cure symptoms and/or complications from the disease or infection, and thus reduce or stop the spread of a Norovirus outbreak in a population. An amount adequate to accomplish this is defined as a "therapeutically effective dose."

The vaccine compositions of the present invention may be administered via a non-mucosal or mucosal route. These administrations may include in vivo administration via parenteral injection (e.g. intravenous, subcutaneous, intradermal, and intramuscular) or other traditional direct routes, such as buccal/sublingual, rectal, oral, nasal, topical (such as transdermal and ophthalmic), vaginal, pulmonary, intraarterial, intraperitoneal, intraocular, or intranasal routes or directly into a specific tissue. Other suitable routes of administration include transcutaneous, subdermal, and via suppository. In one embodiment, the vaccine is administered by a parenteral route of administration, such as intravenous, subcutaneous, intradermal, or intramuscular. In certain embodiments, the vaccine is administered by an intramuscular route of administration. Administration may be accomplished simply by direct administration using a needle, catheter or related device (e.g. pre-filled syringes or autoinjectors), at a single time point or at multiple time points. Other parenteral formulations may be delivered subcutaneously or intradermally by microinjection or skin patch delivery methods.

The present invention provides methods for eliciting protective immunity against Norovirus in a subject comprising parenterally administering to the subject no more than a single dose of a vaccine composition of the invention, wherein said vaccine comprises genogroup I and/or genogroup II Norovirus VLPs as described herein and optionally at least one adjuvant. In such embodiments, the single dose vaccine composition induces at least a three-fold increase in Norovirus-specific serum antibody titer as compared to the titer in the human prior to administration of the composition. In some embodiments, the single dose vaccine composition induces at least a six-fold increase in Norovirus-specific serum antibody titer as compared to the titer in the human prior to administration of the composition. In other embodiments, the single dose vaccine composition induces a Norovirus-specific serum antibody titer comparable to the antibody titer induced by exposure to live Norovirus in a natural infection—i.e., a greater than ten-fold increase in Norovirus-specific serum antibody as compared to the titer in the human prior to administration of the composition. In certain embodiments, the single dose vaccine composition induces the increase in Norovirus-specific serum antibody titer within seven days of administration of the composition. Preferably, the single dose vaccine composition is administered by an intravenous, subcutaneous, or intramuscular route of administration. In a certain embodiment, the single dose vaccine composition is administered intramuscularly to the human.

As described herein, in some embodiments, the single dose vaccine compositions suitable for use in the method comprise no more than 150 µg each of genogroup I and/or genogroup II Noroviruses. For instance, in some embodiments, the vaccine composition comprises no more than 150 µs, no more than 100 µs, no more than 50 µs, no more than 25 µs, no more than 15 µs, or no more than 10 µg of genogroup I Norovirus VLPs. In other embodiments, the vaccine composition comprises no more than 150 µs, no more than 100 µs, no more than 50 µs, no more than 25 µs, no more than 15 µg, or no more than 10 µg of genogroup II Norovirus VLPs. In certain embodiments, the vaccine composition comprises no more than 50 µg of each genogroup I and genogroup II Norovirus VLPs. In embodiments in which the single dose vaccine composition comprises both genogroup I and genogroup II Norovirus VLPs, the dose of genogroup I Norovirus VLPs and genogroup II VLPs can be the same or different. For instance, in one embodiment, the vaccine composition may comprise no more than 50 µg of genogroup I Norovirus VLPs and no more than 150 µg of genogroup II Norovirus VLPs. In another embodiment, the vaccine composition may comprise no more than 25 µg of genogroup I Norovirus VLPs and no more than 50 µg of genogroup II Norovirus VLPs. In other embodiments, the vaccine composition may comprise no more than 15 µg of genogroup I Norovirus VLPs and no more than 50 µg of genogroup II Norovirus VLPs. In still other embodiments, the vaccine composition may comprise no more than 25 µg of genogroup I Norovirus VLPs and no more than 150 µg of genogroup II Norovirus VLPs.

In one embodiment of the method, the subject is a human and the vaccine confers protection from one or more symptoms of Norovirus infection. Although others have reported methods of inducing an immune response with Norovirus antigens (see U.S. Patent Application Publication No. US 2007/0207526), the indicators of a protective immune response against Norovirus in humans have still not been clearly identified (Herbst-Kralovetz et al. (2010) Expert Rev. Vaccines 9(3), 299-307). Unlike several vaccines currently licensed in the U.S. where effectiveness of the vaccine correlates with serum antibodies, studies have shown that markers of an immune response, such as increased titers of serum IgG antibodies against Norwalk virus, are not associated with protective immunity in humans (Johnson et al. (1990) J. Infectious Diseases 161: 18-21). Moreover, another study examining Norwalk viral challenge in humans indicated that susceptibility to Norwalk infection was multifactorial and included factors such as secretor status and memory mucosal immune response (Lindesmith et al. (2003) Nature Medicine 9: 548-553).

Because Norovirus is not able to be cultured in vitro, no viral neutralization assays are currently available. A functional assay which serves as a substitute for the neutralization assay is the hemagglutination inhibition (HAI) assay (see Example 1). HAI measures the ability of Norovirus vaccine-induced antibodies to inhibit the agglutination of antigen-coated red blood cells by Norovirus VLPs because Norovirus VLPs bind to red blood cell antigens (e.g. histo-blood group antigens). This assay is also known as a carbohydrate blocking assay, as it is indicative of the functional ability of antibodies to block binding of the virus or VLPs to blood group antigen carbohydrates on a red blood cell. In this assay, a fixed amount of Norovirus VLPs is mixed with a fixed amount of red blood cells and serum from immunized subjects. If the serum sample contains functional antibodies, the antibodies will bind to the VLPs, thereby inhibiting the agglutination of the red blood cells. As used herein, "functional antibodies" refer to antibodies that are capable of inhibiting the interaction between Norovirus particles and red blood cell antigens. In other words, functional antibody titer is equivalent to histo-blood group antigen (HBGA) or carbohydrate blocking antibody titer. The serum titer of Norovirus-specific functional antibodies can be measured by the HAI assay described above. The serum titer of Norovirus-specific functional antibodies can also be measured using an ELISA-based assay in which a carbohydrate H antigen is bound to microtiter wells and Norovirus VLP binding to H antigen is detected in the presence of serum (see Example 1 and Reeck et al. (2010) J Infect Dis, Vol. 202(8):1212-1218). An increase in the level of Norovirus-specific functional antibodies can be an indicator of a protective immune response. Thus, in one embodiment, the administration of the vaccine elicits a protective immunity comprising an increase in the serum titer of Norovirus-specific functional antibodies as compared to the serum titer in a human not receiving the vaccine. The serum titer of Norovirus-specific functional antibodies indicative of a protective immune response is preferably a geometric mean titer greater than 40, 50, 75, 100, 125, 150, 175, 200 as measured by the HAI assay or blocking titer (BT)$_{50}$ (50% inhibition of H antigen binding by Norovirus VLPs) geometric mean titer of greater than 100, 150, 200, 250, 300, 350, 400, 450, or 500 as measured by the H antigen binding assay. In one embodiment, the serum titer of Norovirus-specific functional antibodies is a geometric mean titer greater than 40 as measured by the HAI assay. In another embodiment, the serum titer of Norovirus-specific functional antibodies is a geometric mean titer greater than 100 as measured by the HAI assay. In another embodiment, the serum titer of Norovirus-specific functional antibodies is a $BT_{50}$ geometric mean titer greater than 100 as measured by the H antigen binding assay. In still another embodiment, the serum titer of Norovirus-specific functional antibodies is a $BT_{50}$ geometric mean titer greater than 200 as measured by the H antigen binding assay.

In a further aspect, the administration of the vaccine elicits a protective immunity comprising an IgA mucosal immune response and an IgG systemic immune response by administering parenterally (preferably intramuscularly) to the subject no more than a single dose of an antigenic or vaccine composition comprising one or more types of Norovirus antigens and optionally at least one effective adjuvant. The inventors have surprisingly found that parenteral administration of the Norovirus vaccine compositions described herein induces a robust IgA response in addition to a strong IgG response. Typically, strong IgA responses are only observed when vaccines are administered through a mucosal route of administration.

In certain embodiments, the administration of the vaccine elicits a protective immunity comprising an increase in the level of IgA Norovirus-specific antibody secreting cells in the blood as compared to the level in a human not receiving the vaccine. In some embodiments, the administration of the vaccine elicits a protective immunity comprising an increase in the level of IgA Norovirus-specific antibody secreting cells in the blood as compared to the level in the human before receiving the vaccine. In one embodiment, the IgA Norovirus-specific antibody secreting cells are CCR10+, CD19+, CD27+, CD62L+, and α4β7+. Antibody secreting cells with this marker profile are capable of homing to both peripheral lymphoid tissue, such as Peyer's patch in the gut, and mucosal lymphoid tissue, such as the gut mucosa. In one embodiment, the number of CCR10+, CD19+, CD27+, CD62L+, and α4β7+ IgA antibody secreting cells is greater than about 500, about 700, about 1,000, about 1,500, or greater than about 2,000 cells per $1\times10^6$ peripheral blood monocytes. In another embodiment, the IgA Norovirus-specific antibody secreting cells are CCR10+, CD19+, CD27+, CD62L-, and α4β7+. Antibody secreting cells with this marker profile generally exhibit homing only to mucosal sites and can be indicative of a memory B-cell response. In some embodiments in which the vaccine is administered intramuscularly, the number of CCR10+, CD19+, CD27+, CD62L-, and α4β7+ IgA antibody secreting cells is greater than about 5,000, about 6,500, about 7,000, about 10,000, about 13,000, about 15,000, or greater than about 20,000 cells per $1\times10^6$ peripheral blood monocytes.

Similar findings have been observed with vaccines for other viruses, such as rotavirus. For rotavirus vaccines, there is controversy over whether serum antibodies are directly involved in protection or merely reflect recent infection (Jiang, 2002; Franco, 2006). Defining such correlates of protection is particularly difficult in the context of diarrheal diseases such as rotavirus or norovirus, where preclinical studies inferring protection may be multifaceted with contributions from mucosal immunity (such as intestinal IgA), cytokine elaboration, and cell mediated immunity. The difficulty in measuring such immune responses during clinical development, and the lack of correlation to serum antibody measurements, requires that the effectiveness of a vaccine for these types of viruses can only be demonstrated through human clinical challenge experiments.

As mentioned above, administration of a vaccine composition of the present invention prevents and/or reduces at least one symptom of Norovirus infection. Symptoms of Norovirus infection are well known in the art and include nausea, vomiting, diarrhea, and stomach cramping. Additionally, a patient with a Norovirus infection may have a low-grade fever, headache, chills, muscle aches, and fatigue. The invention also encompasses a method of inducing a protective immune response in a subject experiencing a Norovirus infection by administering to the subject a vaccine formulation of the invention such that at least one symptom associated with the Norovirus infection is alleviated and/or reduced. A reduction in a symptom may be determined subjectively or objectively, e.g., self assessment by a subject, by a clinician's assessment or by conducting an appropriate assay or measurement (e.g. body temperature), including, e.g., a quality of life assessment, a slowed progression of a Norovirus infection or additional symptoms, a reduced severity of Norovirus symptoms or suitable assays (e.g. antibody titer, RT-PCR antigen detection, and/or B-cell or T-cell activation assay). An effective response may also be determined by directly measuring (e.g., RT-PCR) virus load in stool samples, which reflects the amount of virus shed from the intestines). The objective assessment comprises both animal and human assessments.

The invention also provides a method of generating antibodies to one or more Norovirus antigens, said method comprising administration of a vaccine composition of the invention as described above to a subject. These antibodies can be isolated and purified by routine methods in the art. The isolated antibodies specific for Norovirus antigens can be used in the development of diagnostic immunological assays. These assays could be employed to detect a Norovirus in clinical samples and identify the particular virus causing the infection (e.g. Norwalk, Houston, Snow Mountain, etc.). Alternatively, the isolated antibodies can be administered to subjects susceptible to Norovirus infection to confer passive or short-term immunity.

The invention will now be illustrated in greater detail by reference to the specific embodiments described in the following examples. The examples are intended to be purely illustrative of the invention and are not intended to limit its scope in any way.

EXAMPLES

Example 1. Dose Escalation, Safety and Immunogenicity Study of Intramuscular Norovirus Bivalent Virus-Like-Particle (VLP) Vaccine in Humans (LV03-104 Study), Cohort A This example describes Cohort A of a randomized, multi-site, dose-escalation study of the safety and immunogenicity of four dosage levels of an intramuscular (IM) Norovirus Bivalent VLP Vaccine adjuvanted with monophosphoryl lipid A (MPL) and aluminum hydroxide (AlOH) compared to placebo in adult subjects. Approximately 48 subjects 18 to 49 years of age were enrolled in the cohort. Subjects received two doses of the vaccine or placebo, by intramuscular (IM) injection, 28 days apart using a 1.5 inch (38 mm) needle.

The Norovirus Bivalent VLP Vaccine contained genogroup I, genotype 1 (GI.1) and genogroup II, genotype IV (GII.4) VLPs as the antigens, and Monophosphoryl Lipid A (MPL) and aluminum hydroxide (AlOH) as adjuvants, sodium chloride (NaCl) and L-histidine (L-His) as buffer (pH 6.3-6.7), ethanol and water for injection. The composition of the intramuscular Norovirus Bivalent VLP Vaccine is summarized in Table 1. The GII.4 VLPs comprised a capsid sequence of SEQ ID NO: 1, which was derived from three GII.4 strains.

TABLE 1

Final Drug Product Composition for Four IM Norovirus Bivalent VLP Vaccine Formulations per 0.5 mL

| | Formulation | | | | | | |
|---|---|---|---|---|---|---|---|
| | GI.1-VLP (μg) | GII.4 VLP (μg) | MPL (μg) | Al* (mg) | NaCl (mg) | L-His (mg) | Ethanol (mg) |
| 10 μg Dosage | 5 | 5 | 50 | 0.5 | 4.38 | 1.55 | 19.7 |
| 30 μg Dosage | 15 | 15 | 50 | 0.5 | 4.38 | 1.55 | 19.7 |
| 100 μg Dosage | 50 | 50 | 50 | 0.5 | 4.38 | 1.55 | 19.7 |
| 300 μg Dosage | 150 | 150 | 50 | 0.5 | 4.38 | 1.55 | 19.7 |

*as Aluminum Hydroxide

Placebo was sterile normal saline for injection (0.9% NaCl and preservative-free). The dose escalation of the vaccine was conducted as follows: after appropriate screening for good health, subjects in Cohort A were enrolled sequentially into each of four dosage groups of ~12 subjects each (Dosage Groups A1, A2, A3, and A4). Dosage Groups A1, A2, A3, and A4 represent bivalent antigenic dosages of 5/5 μg, 15/15 μg, 50/50 μg, and 150/150 μg, respectively, of the G I.1 and GII.4 norovirus. Subjects in each dosage group were randomized 5:1 to receive vaccine or placebo. Subjects in Dosage Group A1 received their respective randomized treatment (10 subjects received 5/5 μg vaccine and 2 subjects received placebo). Subjects were followed for safety assessment by review of the symptoms recorded on the memory aid (Days 0-7) and interim medical histories from the Day 7, 21, 28, 35, and 56 visits. Safety data was reviewed by the Central Safety Monitor (CSM). After the 7-day post Dose 2 safety data (Study Day 35) were available for review from subjects in Dosage Group A1 and considered acceptable, subjects in Dosage Group A2 were eligible to receive their initial dose. The same rule applied for dosing in the subsequent dosage groups; that is, after the 7-day post Dose 2 safety data (Study Day 35) were available for review from a dosage group, the next dosage group was eligible to receive their initial dose.

At the end of enrollment in Cohort A, approximately 10 subjects in each Dosage Group received vaccine (total of 40 vaccinees) and 2 subjects in each group received saline (total of approximately 8 saline control recipients).

The subjects kept a daily memory aid of solicited symptoms including four local injection site reactions, such as pain, tenderness, redness, and swelling, and 10 systemic signs or symptoms including daily oral temperature, headache, fatigue, muscle aches, chills, joint aches and gastrointestinal symptoms of nausea, vomiting, diarrhea, abdominal cramps/pain for Days 0 through 7 after each dose of IM Norovirus Bivalent VLP Vaccine or control. The redness and swelling at the injection site was measured and recorded daily for 7 days after each injection.

Interim medical histories were obtained at each follow-up visit on Days 7+3, 21+3, 28+3, 35+3, 56+7, 180+14, and 393+14 and at the follow-up telephone call on Day 265+14; subjects were queried about interim illness, doctor's visits, any serious adverse events (SAEs), and onset of any significant new medical conditions. Subjects had a CBC with WBC differential and platelet count, and serum BUN, creatinine, glucose, AST, and ALT assessed at screening and on Days 21 and 35 (~7 days after each dose) to assess continuing eligibility and safety, respectively.

Blood from subjects was collected before vaccination on Day 0 and on Days 7+3, 21+3, 28+3, 35+3, 56+7, 180+14, and 393+14 to measure serum antibodies (IgG, IgA, and IgM separately and combined) to IM Norovirus Bivalent VLP Vaccine by enzyme-linked immunosorbent assays (ELISA). Serum carbohydrate blocking activity and serum HAI antibodies were also measured. For subjects in Cohort A, antibody secreting cells (ASCs), homing markers, memory B cells and cellular immune responses were assayed.

The following methods were used to analyze the blood samples collected from immunized individuals or individuals receiving the placebo.

Serum Antibody Measurements by ELISA

Measurement of antibodies to norovirus by ELISA was performed for all subjects, using purified recombinant Norovirus VLPs (GI.1 and GII.4 separately) as target antigens to screen the coded specimens. Briefly, norovirus VLPs in carbonate coating buffer pH 9.6 were used to coat microtiter plates. Coated plates were washed, blocked, and incubated with serial two-fold dilutions of test serum followed by washing and incubation with enzyme-conjugated secondary antibody reagents specific for human total IgG, IgG1, IgG2, IgG3, IgG4, IgA and IgM. Appropriate substrate solutions were added, color developed, plates read and the IgG, IgA and IgM endpoint titers determined in comparison to a reference standard curve for each antibody class. Geometric mean titers (GMTs), geometric mean fold rises (GMFRs) and seroresponse rates for each group was determined. Seroresponse was defined as a 4-fold increase in antibody titer compared to pre-immunization titers.

Norovirus Carbohydrate Histo-Blood-Group Antigens (HBGA) Blocking Activity

Blocking assays to measure the ability of serum antibodies to inhibit NV VLP binding to H type 1 or H type 3 synthetic carbohydrates were performed as previously described (Reeck et al. (2010) J Infect Dis, Vol. 202(8): 1212-1218). Briefly, NV VLPs for the blocking assays were incubated with an equal volume of serum, and serially two-fold diluted from a starting dilution of 1:25. Neutravidin-coated, 96-well microtiter plates were washed and coated with 2.5 μg/mL of either synthetic polyvalent H type 1-PAA-biotin or polyvalent H type 3-PAA-biotin. The sera-VLP solutions were added. Plates were washed and rabbit polyclonal sera specific to NV VLPs was added, washed, and followed by incubation with horseradish peroxidase conjugated goat anti-rabbit IgG. The color was developed with tetramethylbenzidine peroxidase liquid substrate and stopped with 1M phosphoric acid. Optical density was measured at 450. Positive and negative controls were performed. Fifty-percent blocking titers (BT50) were determined, defined as the titer at which OD readings (after subtraction of the blank) are 50% of the positive control. A value of 12.5 was assigned to samples with a BT50 less than 25. Geometric mean titers (GMTs), geometric mean fold rises (GMFRs) and seroresponse rates for each group were determined. Seroresponse was defined as a 4-fold increase in antibody titer compared to pre-immunization titers. A blocking control serum sample was used as an internal control. An assay to confirm the specificity of the blocking was performed using the same protocol for the blocking assay with the following exceptions: after coating with carbohydrate, sera was incubated directly on the plate without first pre-incubating with VLP. After washing, VLPs were incubated on the plate and detected as for the blocking assay.

Norovirus Hemagglutination Antibody Inhibition (HAI) Assay

Vaccine-induced antibodies were examined for the capacity to inhibit hemagglutination of 0-type human RBCs by the norovirus VLPs as previously described (El Kamary et al. (2010) J Infect Dis, Vol. 202(11): 1649-58). HAI titers were calculated as the inverse of the highest dilution that inhibited hemagglutination with a compact negative RBC pattern and are presented as GMTs, GMFRs and ≥4-fold rises.

Norovirus GI.1 and GII.4 VLPs were separately serially diluted and incubated with an equal volume of a 0.5% human RBC suspension in a 96-well V bottom plate. The amount of norovirus VLP antigens corresponding to 4 HA units were determined and confirmed by back titration. Test sera were heat inactivated at 56 C for 30 minutes and treated with freshly prepared 25% Kaolin suspension. To eliminate serum inhibitors, test samples were pre-adsorbed with RBCs. The HAI assay were performed as follows: pretreated sera (diluted 2-fold in PBS pH 5.5) were added to 96 well V-plates and incubated with an equal volume of Norovirus GI.1 and GII.4 VLP antigen, respectively, containing 4 HA units. A suspension of 0.5% RBCs was added to each well and plates incubated for an additional 90 minutes at 4 C. Wells containing only PBS or antigen without serum served as negative and positive controls, respectively. Geometric mean titers (GMTs), geometric mean fold rises (GMFRs) and seroresponse rates for each group were determined. Seroresponse was defined as a 4-fold increase in antibody titer compared to pre-immunization titers.

Antibody Secreting Cell Assays

PBMCs were isolated from approximately 60 mL of anti-coagulated blood on Days 0, 7+3, 28+3, and 35+3 after administration of IM Norovirus Bivalent VLP Vaccine or placebo. Approximately 25 mL of blood for fresh PBMC assays and 35 mL of blood for cryopreservation of PBMCs was obtained. ASC assays detect cells secreting antibodies to norovirus VLPs (Tacket et al. (2000) J. Infect. Dis., Vol. 182:302-305; Tacket et al. (2003) Clin. Immunol., Vol. 108:241-247; El Kamary et al. (2010) J Infect Dis, Vol. 202(11): 1649-58). Fresh PBMCs were evaluated for ASC frequency and determination of homing markers from a subset of subjects. Cryopreserved PBMCs from subjects participating in Cohort A were evaluated for ASC frequency. The response rate and mean number of ASC per $10^6$ PBMCs at each time point for each group are described. A positive response is defined as a post-vaccination ASC count per $10^6$ PBMCs that is at least 3 standard deviations (SD) above the mean pre-vaccination count for all subjects (in the log metric) and at least 8 ASC spots, which corresponds to the mean of medium-stimulated negative control wells (2 spots) plus 3 SD as determined in similar assays.

Measurement of Norovirus Virus-Specific Memory B-Cells

Anti-coagulated blood was collected only in Cohort A subjects (approximately 25 mL on Days 0, 28, 56 and 180) to measure memory B cells on days 0, 28, 56 and 180 after vaccination using an ELISpot assay preceded by in vitro antigen stimulation (Crotty et al. (2004) J. Immunol. Methods, Vol. 286:111-122.; Li et al. (2006) J. Immunol. Methods, Vol. 313:110-118). Peripheral blood mononuclear cells ($5 \times 10^6$ cells/mL, 1 mL/well in 24-well plates) were incubated for 4 days with norovirus GI.1 and GII.4 VLP antigens separately to allow for clonal expansion of antigen-specific memory B cells and differentiation into antibody secreting cells. Controls included cells incubated in the same conditions in the absence of antigen and/or cells incubated with an unrelated antigen. Following stimulation, cells were washed, counted, and transferred to ELISpot plates coated with Norwalk VLP. To determine frequency of virus-specific memory B cells per total Ig-secreting B lymphocytes, expanded B cells were also added to wells coated with anti-human IgG and anti-human IgA antibodies. Bound antibodies were revealed with HRP-labeled anti-human IgG or anti-human IgA followed by appropriate substrate. Conjugates to IgA and IgG subclasses (IgA1, IgA2 and IgG1-4) are also used to determine antigen-specific subclass responses that may be related with distinct effector mechanisms and locations of immune priming. Spots were counted with an ELISpot reader. The expanded cell populations for each subject were examined by flow cytometry to confirm their memory B cell phenotype, i.e. CD19+, CD27+, IgG+, IgM+, CD38+, IgD, among others (Crotty et al. (2004) J. Immunol. Methods, Vol. 286:111-122.; Li et al. (2006) J. Immunol. Methods, Vol. 313:110-118).

Cellular Immune Responses

Anti-coagulated blood (approximately 25 mL on Days 0, 28, 56, and 180) from subjects in Cohort A were collected as coded specimens and the PBMCs isolated and cryopreserved in liquid nitrogen for possible future evaluation of CMI responses to norovirus GI.1 and GII.4 VLP antigens. Assays that are performed include PBMC proliferative and cytokine responses to norovirus GI.1 and GII.4 VLP antigens by measuring interferon (IFN)-γ and interleukin (IL)-4 levels among others according to established techniques (Samandari et al. (2000) J. Immunol., Vol. 164:2221-2232; Tacket et al. (2003) Clin. Immunol., Vol. 108:241-247). T cell responses are also evaluated.

Results

Safety assessment included local and systemic solicited symptoms for 7 days and unsolicited symptoms for 28 days after each dose. Serious Adverse Events are monitored for 12 months. Immunogenicity was assessed with serum obtained prior to and after each vaccination for Pan-ELISA antibodies (IgG, IgA and IgM combined) and peripheral blood mononuclear cells (PBMCs) for IgG and IgA antibody secreting cells (ASC) via Elispot.

All four dosage groups have been enrolled for Cohort A with post dose two safety data available from all four dosage groups (40 vaccinees total). Among the 40 vaccinees, pain or tenderness were the most common local symptoms reported after either dose, whereas swelling or redness was infrequent. No severe local symptoms were reported. Systemic symptoms of headache, myalgia, or malaise after either dose were reported by less than half of the vaccinees. No vaccinees reported fever. No related SAEs were reported.

Figure 1A:
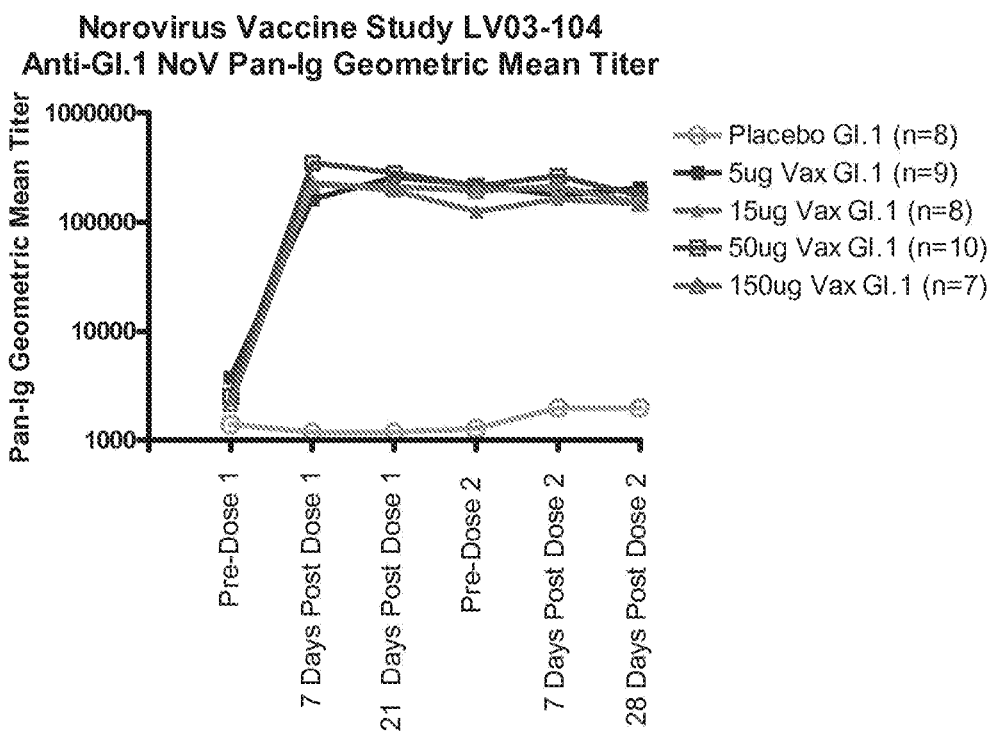
FIG. 1A-FIG. 1B. Results of pan-ELISA assays measuring combined serum IgG, IgA, and IgM levels from human volunteers immunized intramuscularly with placebo (saline) or a vaccine formulation containing 5, 15, 50, or 150 µg each of a genogroup I.1 Norovirus VLP and a genogroup II.4 Norovirus VLP. The geometric mean titer for anti-GI.1 (FIG. 1A) and anti-GII.4 (FIG. 1B) antibodies is shown for each of the dosage levels at 7 and 21 days after the first immunization and 7 and 28 days after the second immunization. Volunteers received immunizations on study days 0 and 28.
Figure 1B:
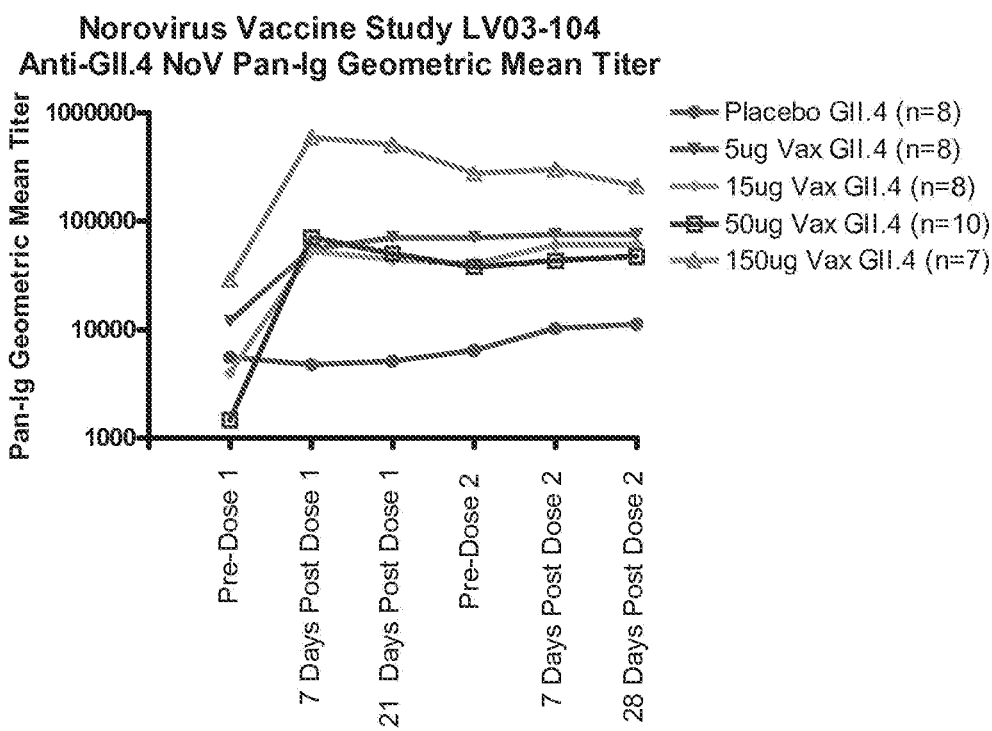
Figure 2A:
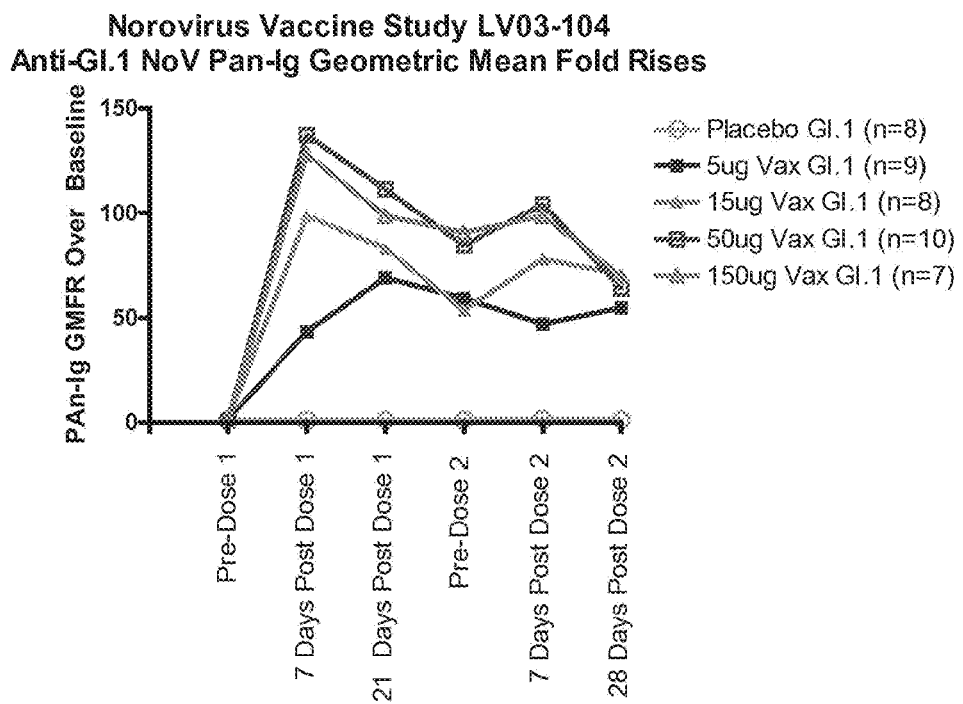
FIG. 2A-FIG. 2B. Results of pan-ELISA assays measuring combined serum IgG, IgA, and IgM levels from human volunteers immunized intramuscularly with placebo (saline) or a vaccine formulation containing 5, 15, 50, or 150 µg each of a genogroup I.1 Norovirus VLP and a genogroup II.4 Norovirus VLP. The geometric mean fold rise for anti-GI.1 (FIG. 2A) and anti-GII.4 (FIG. 2B) antibodies is shown for each of the dosage levels at 7 and 21 days after the first immunization and 7 and 28 days after the second immunization. Volunteers received immunizations on study days 0 and 28.
Figure 2B:
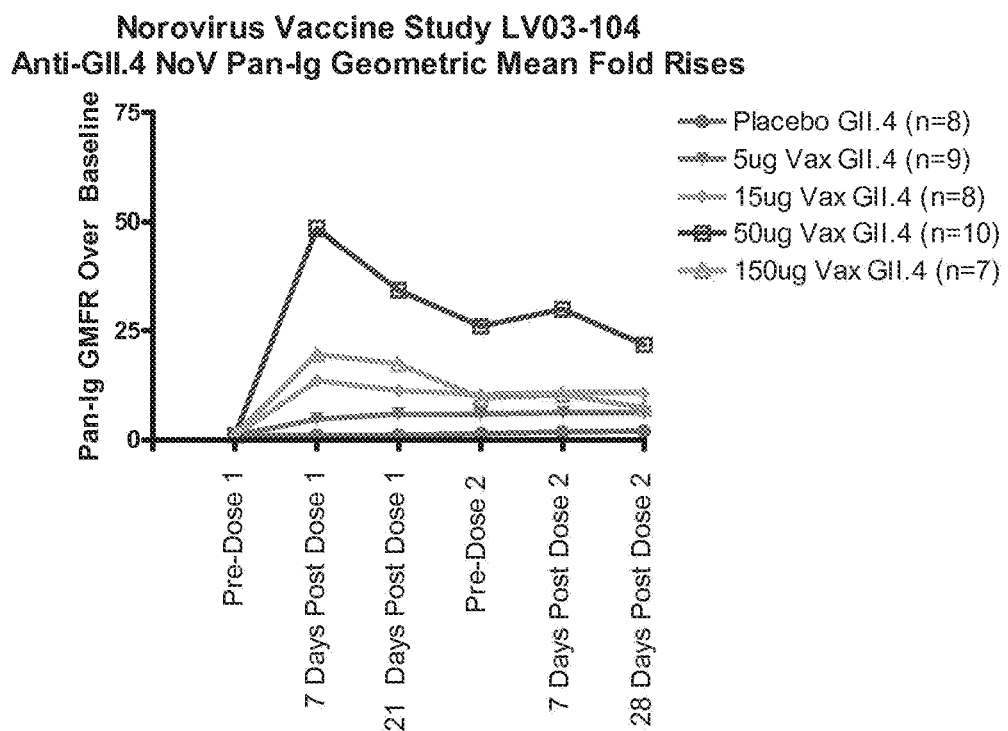
Figure 3A:
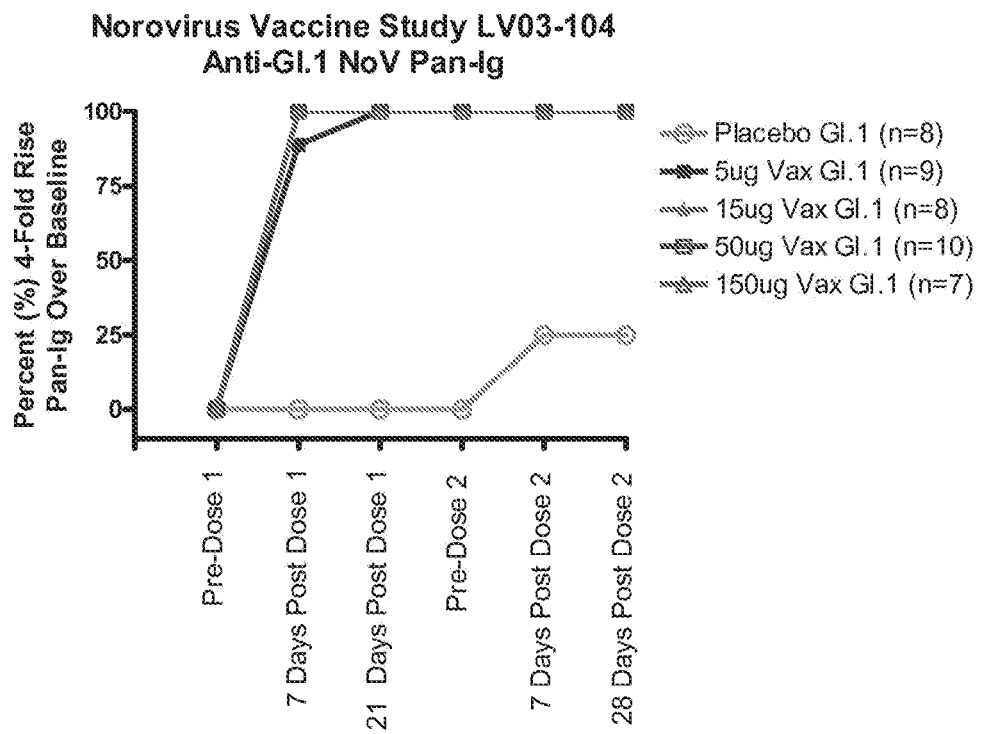
FIG. 3A-FIG. 3B. Results of pan-ELISA assays measuring combined serum IgG, IgA, and IgM levels from human volunteers immunized intramuscularly with placebo (saline) or a vaccine formulation containing 5, 15, 50, or 150 µg each of a genogroup I.1 Norovirus VLP and a genogroup II.4 Norovirus VLP. The percent seroresponse rates (i.e. four-fold increase in antibody titer compared to pre-immunization titers) for anti-GI.1 (FIG. 3A) and anti-GII.4 (FIG. 3B) antibodies are shown for each of the dosage levels at 7 and 21 days after the first immunization and 7 and 28 days after the second immunization. Volunteers received immunizations on study days 0 and 28.
Figure 3B:
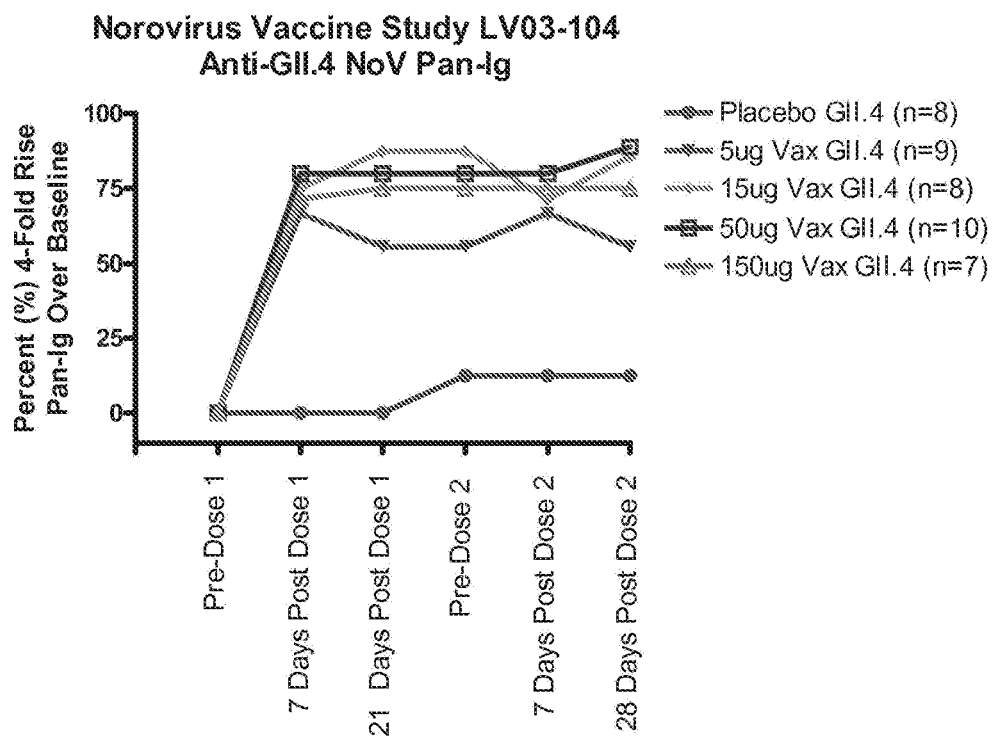
Figure 4A:
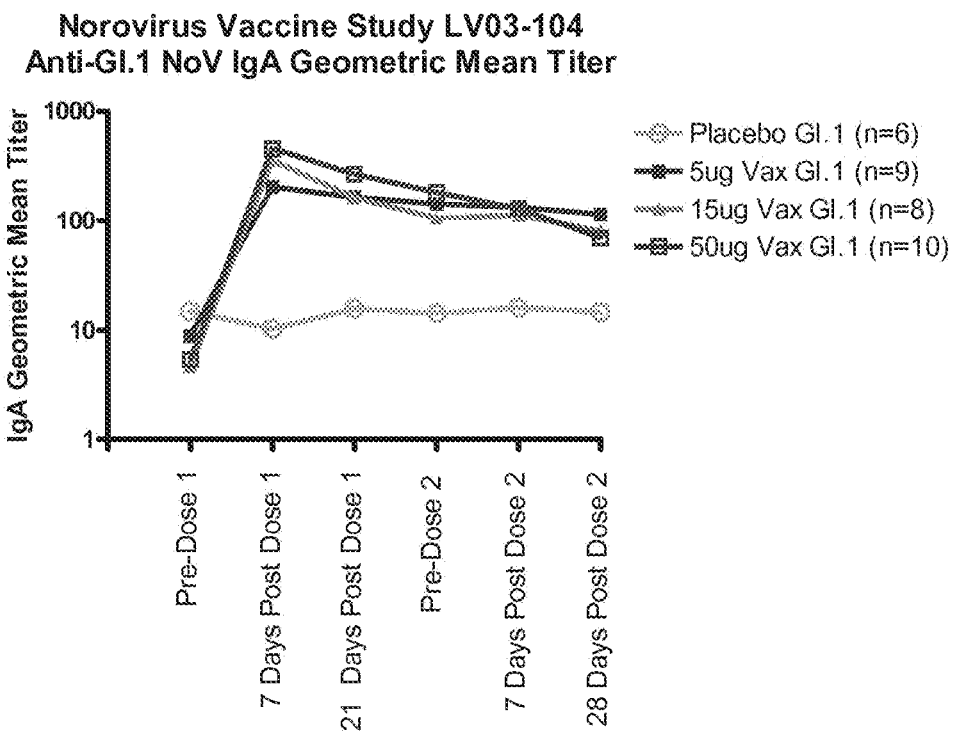
FIG. 4A-FIG. 4B. Results of ELISA assays measuring serum IgA from human volunteers immunized intramuscularly with placebo (saline) or a vaccine formulation containing 5, 15, or 50 µg each of a genogroup I.1 Norovirus VLP and a genogroup II.4 Norovirus VLP. The geometric mean titer for anti-GI.1 (FIG. 4A) and anti-GII.4 (FIG. 4B) antibodies is shown for each of the dosage levels at 7 and 21 days after the first immunization and 7 and 28 days after the second immunization. Volunteers received immunizations on study days 0 and 28.
Figure 4B:
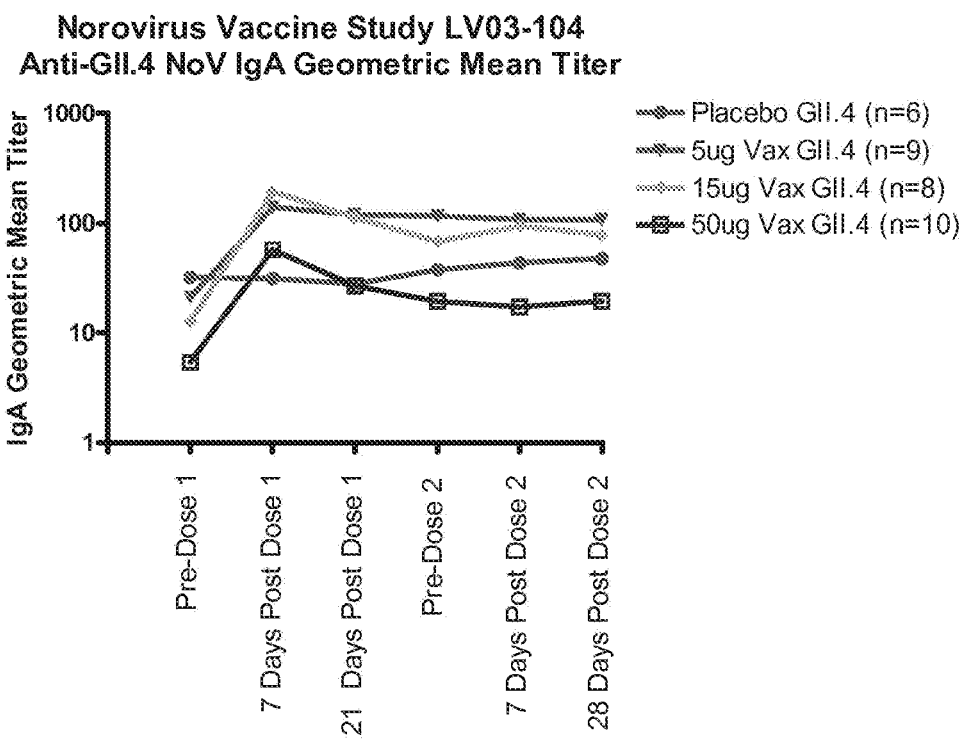
Figure 5A:
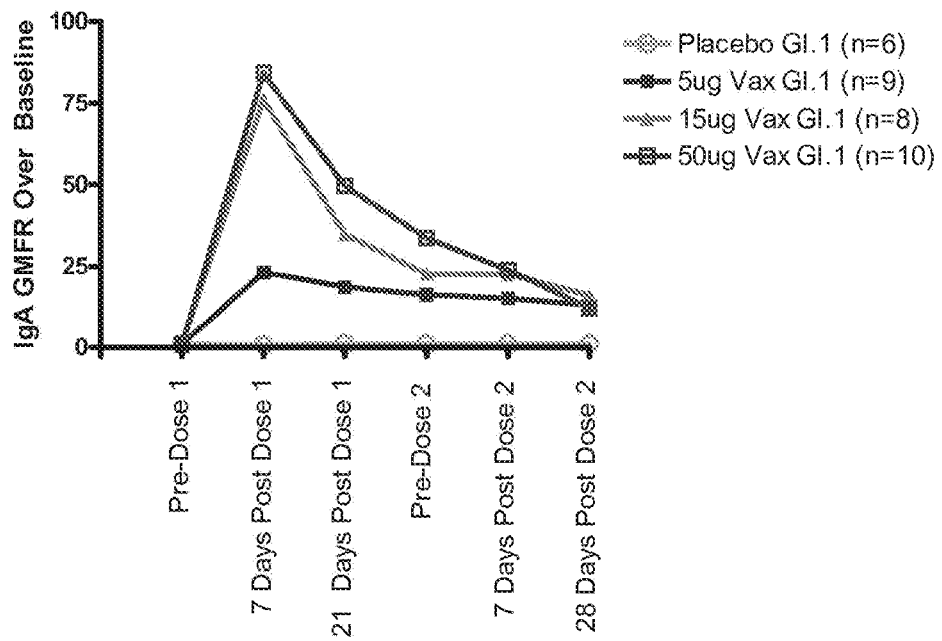
FIG. 5A-FIG. 5B. Results of ELISA assays measuring serum IgA from human volunteers immunized intramuscularly with placebo (saline) or a vaccine formulation containing 5, 15, or 50 µg each of a genogroup I.1 Norovirus VLP and a genogroup II.4 Norovirus VLP. The geometric mean fold rise for anti-GI.1 (FIG. 5A) and anti-GII.4 (FIG. 5B) antibodies is shown for each of the dosage levels at 7 and 21 days after the first immunization and 7 and 28 days after the second immunization. Volunteers received immunizations on study days 0 and 28.
Figure 5B:
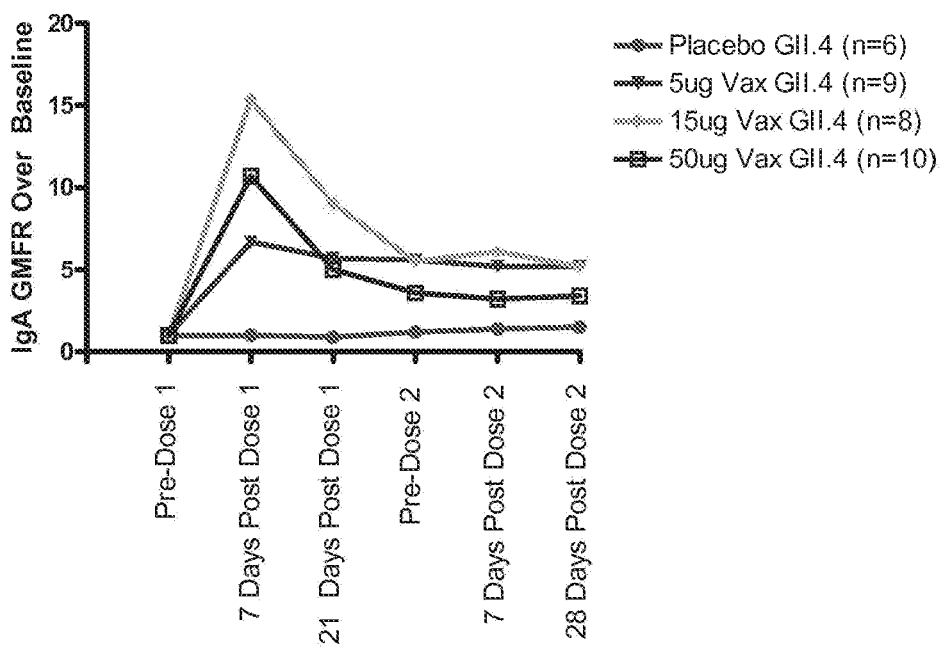
Figure 6A:
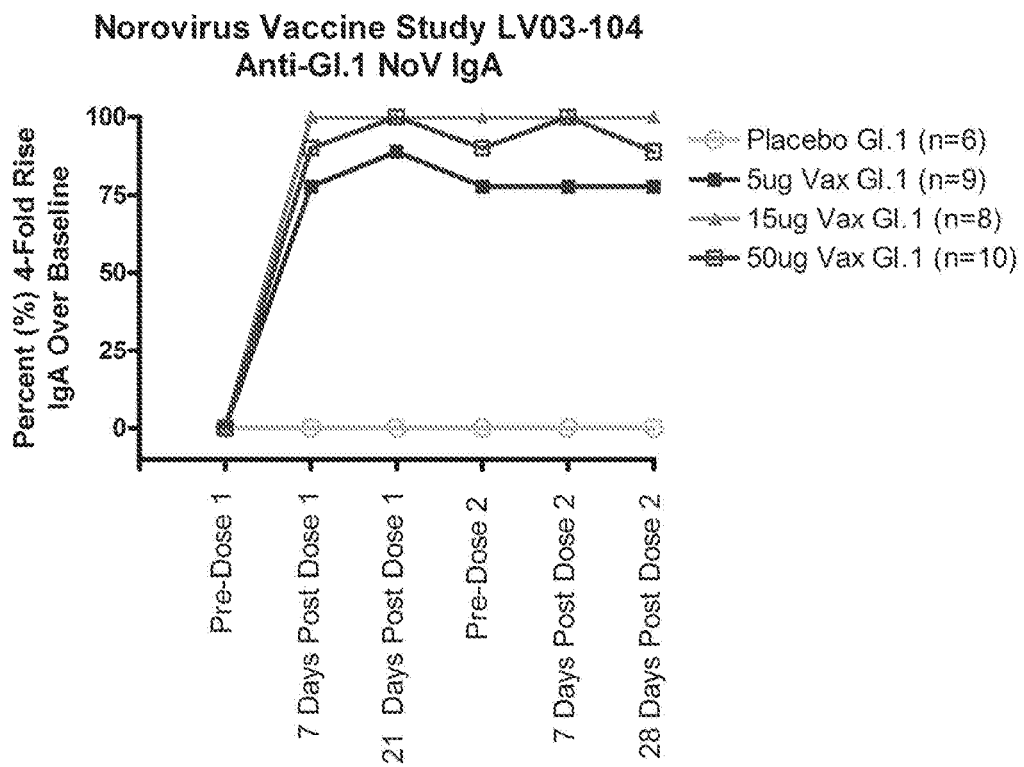
FIG. 6A-FIG. 6B. Results of ELISA assays measuring serum IgA from human volunteers immunized intramuscularly with placebo (saline) or a vaccine formulation containing 5, 15, or 50 µg each of a genogroup I.1 Norovirus VLP and a genogroup II.4 Norovirus VLP. The percent seroresponse rates (i.e. four-fold increase in antibody titer compared to pre-immunization titers) for anti-GI.1 (FIG. 6A) and anti-GII.4 (FIG. 6B) antibodies are shown for each of the dosage levels at 7 and 21 days after the first immunization and 7 and 28 days after the second immunization. Volunteers received immunizations on study days 0 and 28.
Figure 6B:
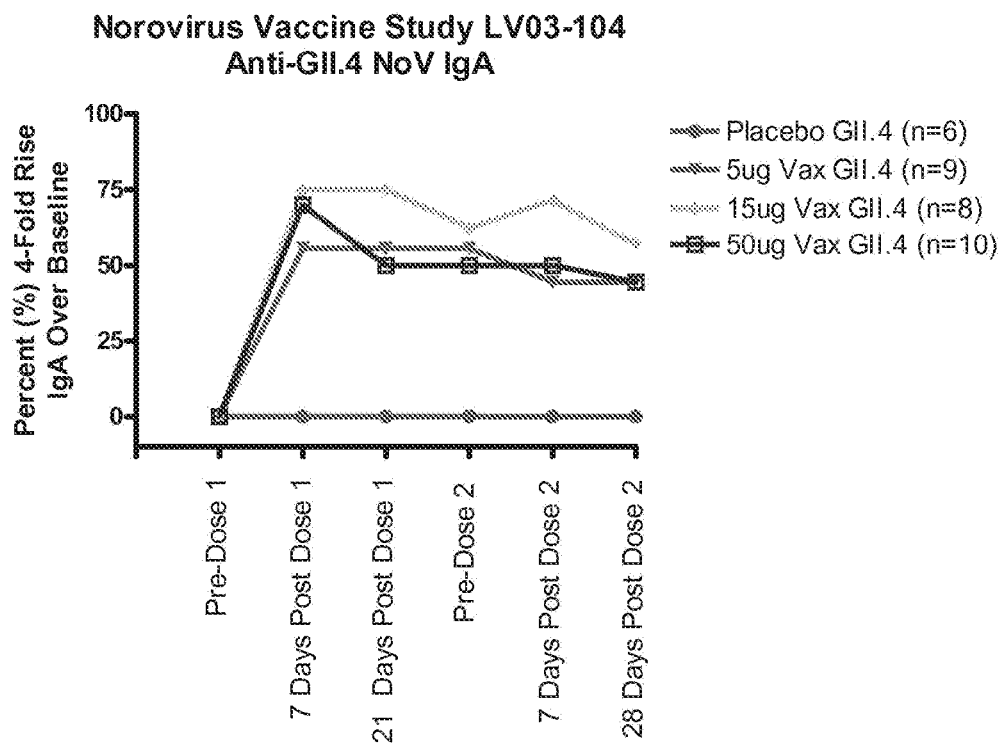
Figure 7A:
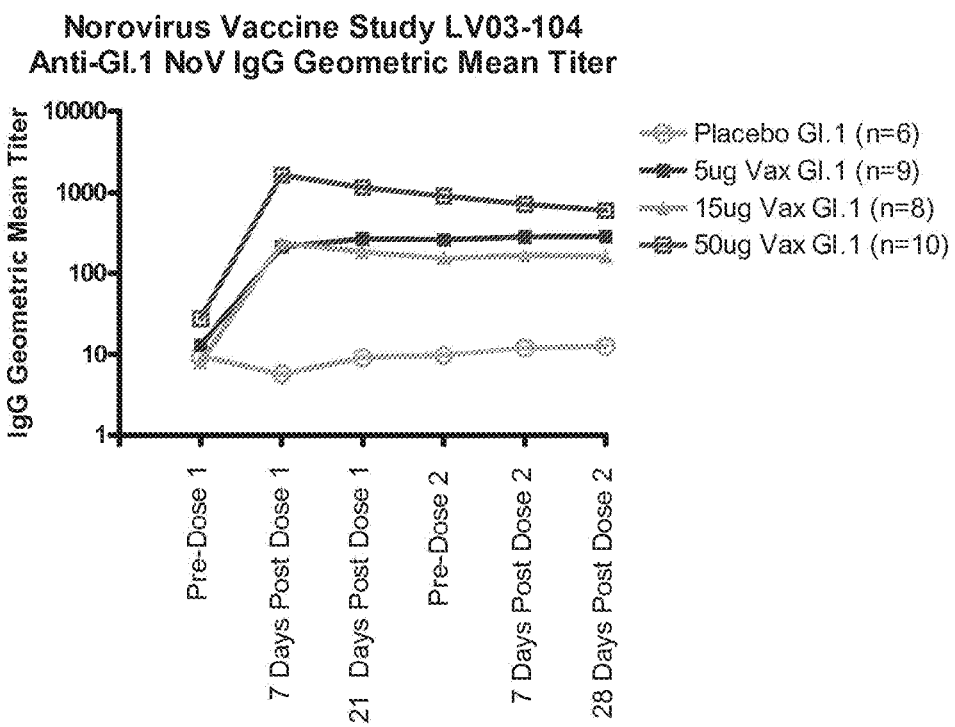
FIG. 7A-FIG. 7B. Results of ELISA assays measuring serum IgG from human volunteers immunized intramuscularly with placebo (saline) or a vaccine formulation containing 5, 15, or 50 µg each of a genogroup I.1 Norovirus VLP and a genogroup II.4 Norovirus VLP. The geometric mean titer for anti-GI.1 (FIG. 7A) and anti-GII.4 (FIG. 7B) antibodies is shown for each of the dosage levels at 7 and 21 days after the first immunization and 7 and 28 days after the second immunization. Volunteers received immunizations on study days 0 and 28.
Figure 7B:
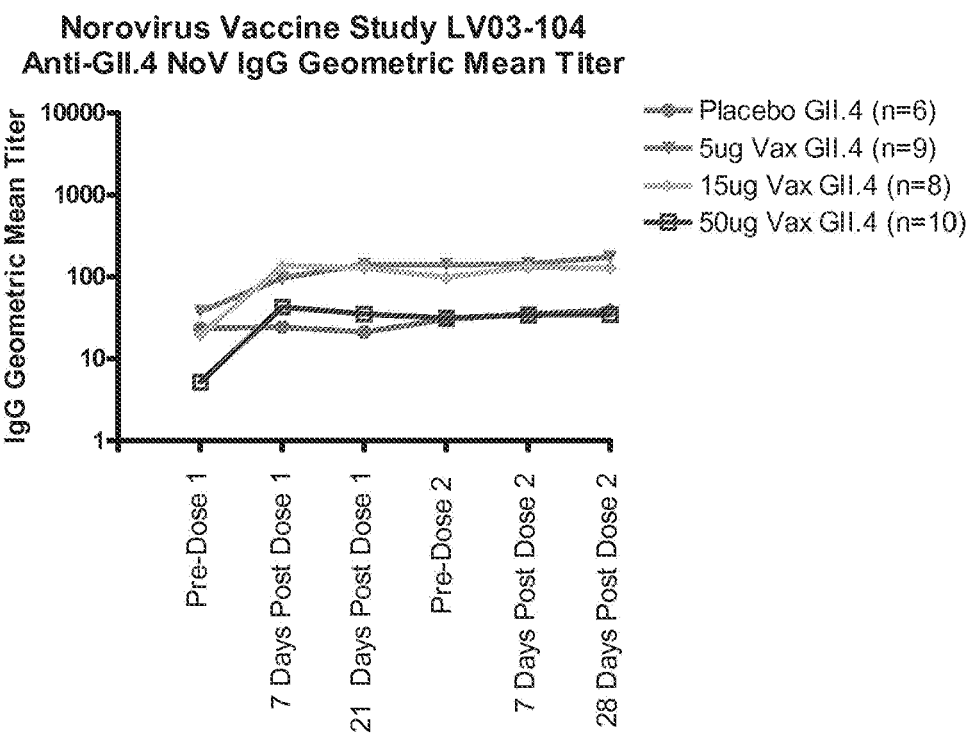
Figure 8A:
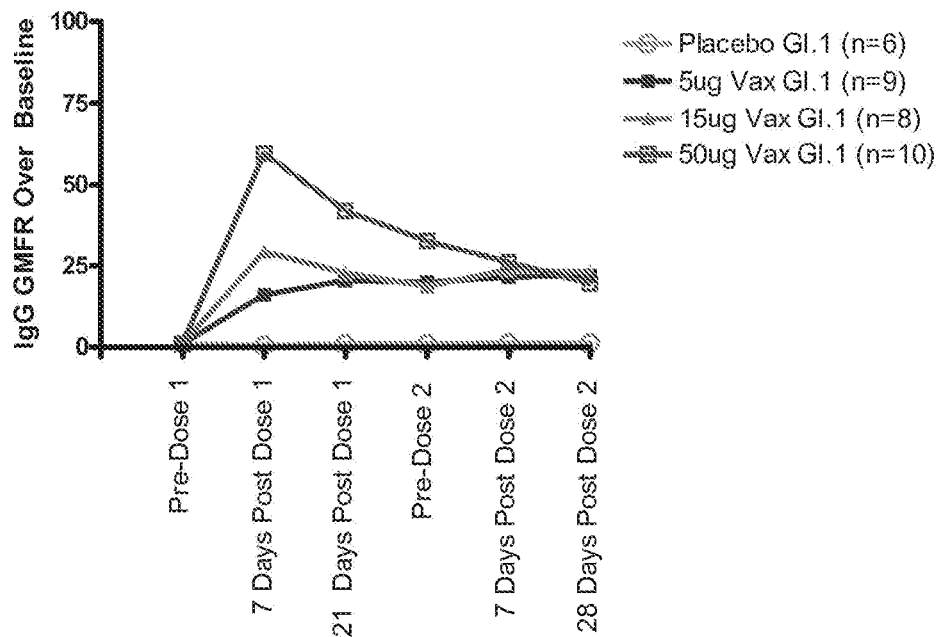
FIG. 8A-FIG. 8B. Results of ELISA assays measuring serum IgG from human volunteers immunized intramuscularly with placebo (saline) or a vaccine formulation containing 5, 15, or 50 µg each of a genogroup I.1 Norovirus VLP and a genogroup II.4 Norovirus VLP. The geometric mean fold rise for anti-GI.1 (FIG. 8A) and anti-GII.4 (FIG. 8B) antibodies is shown for each of the dosage levels at 7 and 21 days after the first immunization and 7 and 28 days after the second immunization. Volunteers received immunizations on study days 0 and 28.
Figure 8B:
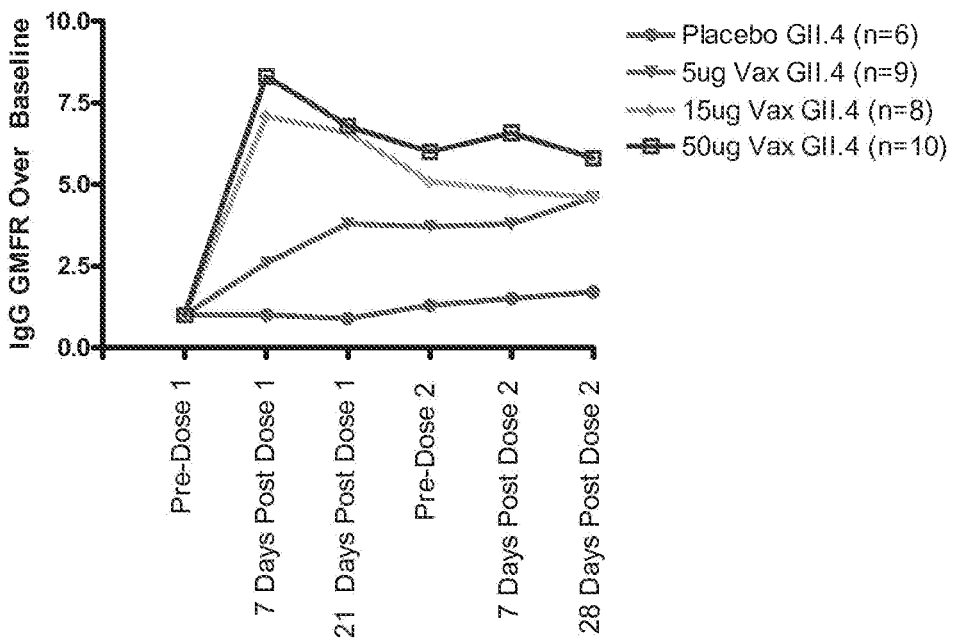
Figure 9A:
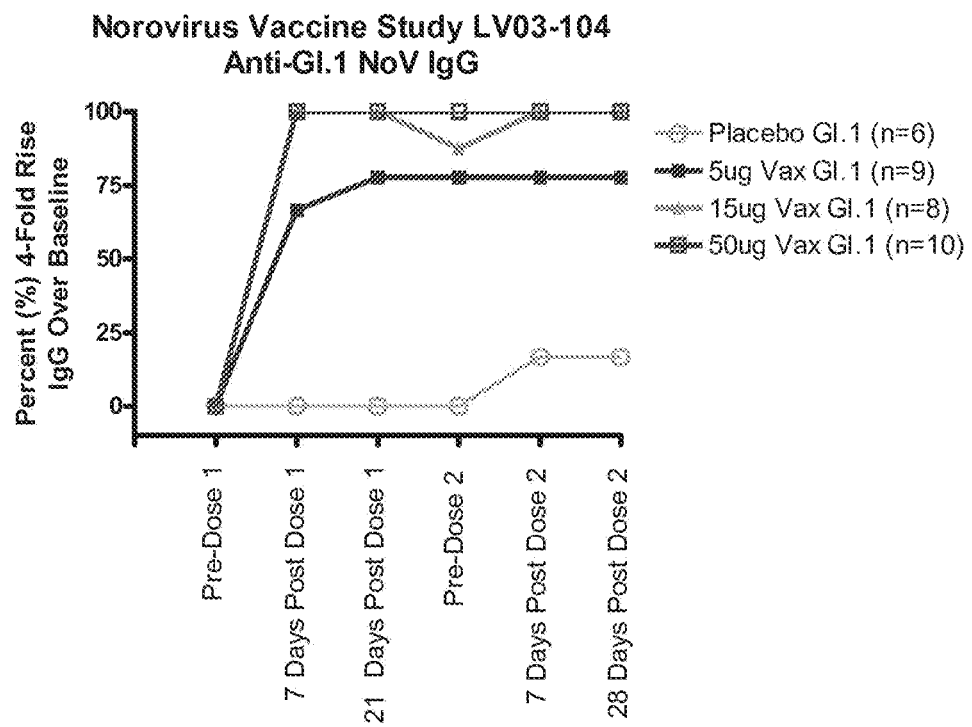
FIG. 9A-FIG. 9B. Results of ELISA assays measuring serum IgG from human volunteers immunized intramuscularly with placebo (saline) or a vaccine formulation containing 5, 15, or 50 µg each of a genogroup I.1 Norovirus VLP and a genogroup II.4 Norovirus VLP. The percent seroresponse rates (i.e. four-fold increase in antibody titer compared to pre-immunization titers) for anti-GI.1 (FIG. 9A) and anti-GII.4 (FIG. 9B) antibodies are shown for each of the dosage levels at 7 and 21 days after the first immunization and 7 and 28 days after the second immunization. Volunteers received immunizations on study days 0 and 28.
Figure 9B:
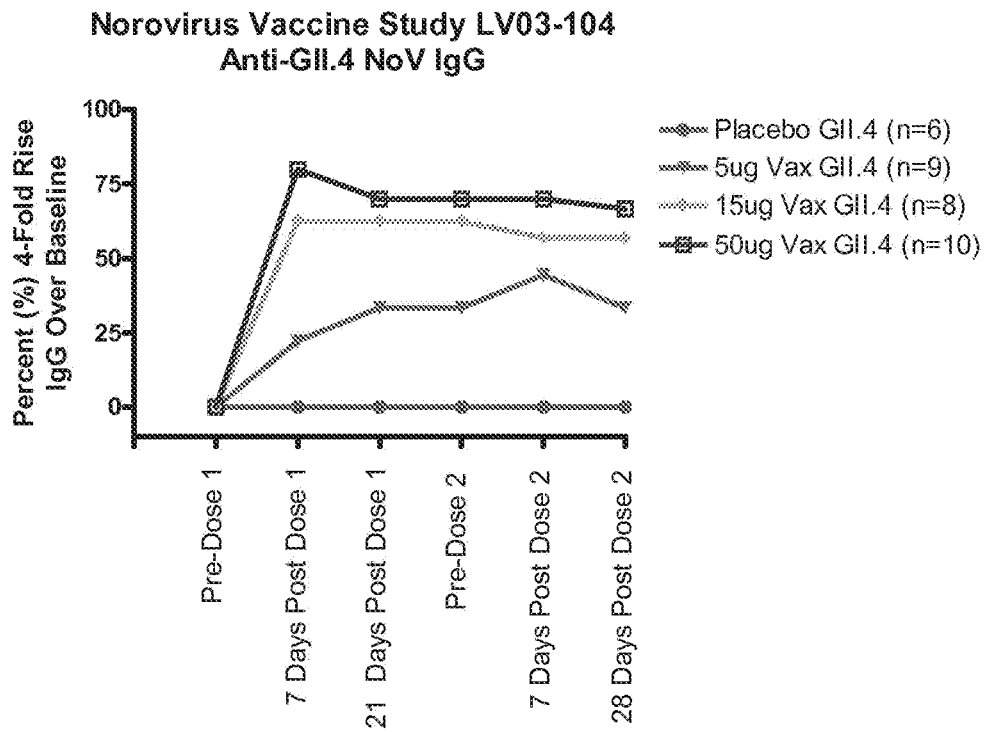
Figure 10:
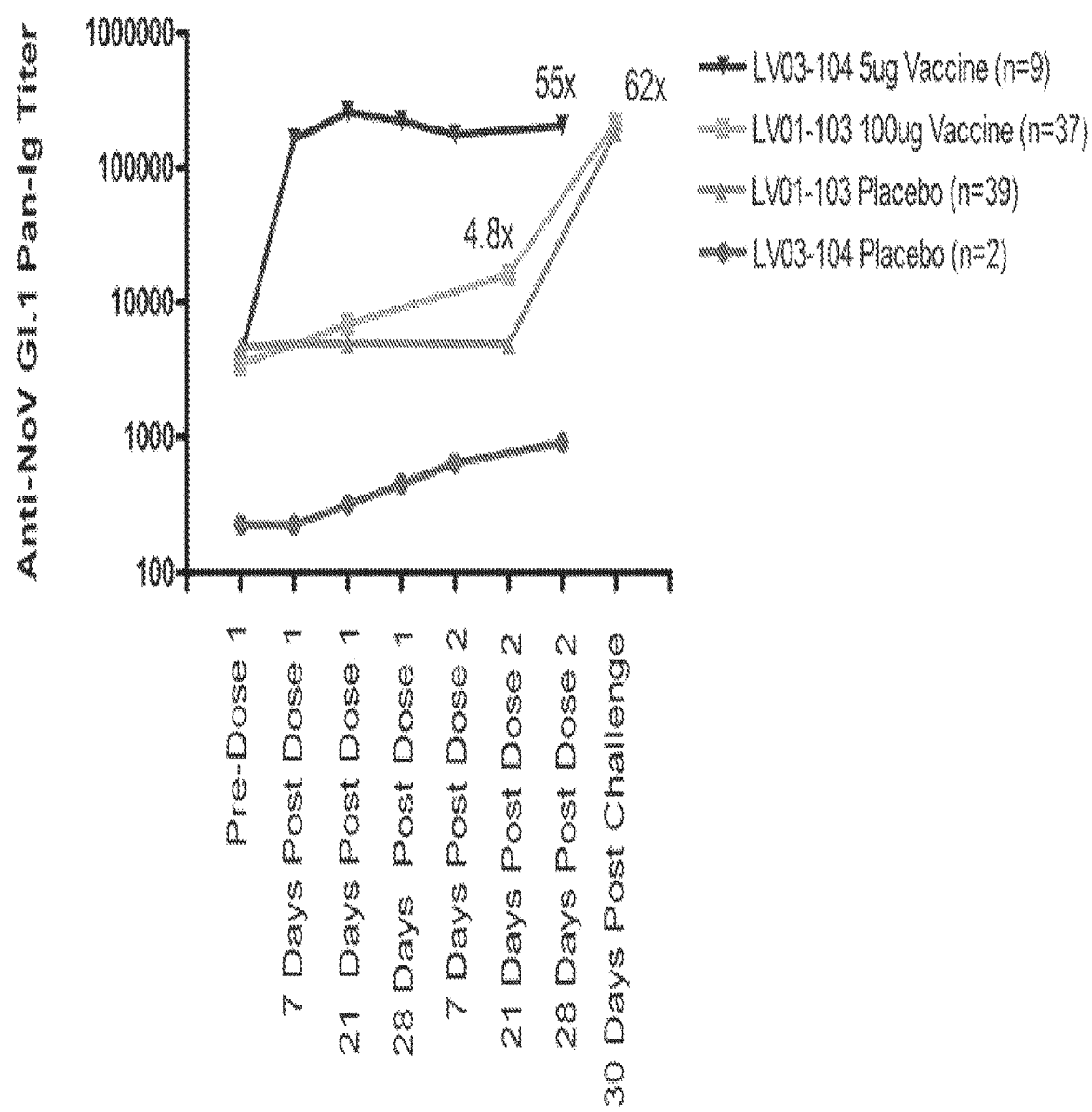
FIG. 10. Results of pan-ELISA assays measuring combined serum IgG, IgA, and IgM levels from human volunteers immunized with either a Norovirus intranasal, monovalent vaccine as described in El Kamary et al. (2010) J Infect Dis, Vol. 202(11): 1649-1658 (LV01-103 groups) or a Norovirus intramuscular, bivalent vaccine as described in Example 1 (LV03-104 groups) at the indicated time points. Human volunteers received either placebo or two doses of either the intramuscular or intranasal vaccine formulation.

As shown in FIGS. 1A-3B, robust anamnestic Pan-ELISA antibody responses (combined IgG, IgA, and IgM) were observed to both VLP antigens 7 days after the first dose of the lowest dosage (5 μg GI.1+5 μg of GII.4 VLPs). The second dose did not boost the post dose one responses. Similar results were observed for antigen-specific serum IgG and serum IgA responses measured separately (FIGS. 4A-9B). Dose-dependent responses were observed for the antibody responses to both antigens (FIGS. 1A-9B). However, the maximal response to the GI.1 VLP appeared to be achieved with a lower dose than the maximal response to the GII.4 VLP (15 μg vs. 50 μg). Interestingly, the single dose of the intramuscularly administered Norovirus bivalent vaccine induced a surprisingly, significantly greater antigen-specific antibody titer than the titer induced by two doses of an intranasally administered monovalent VLP vaccine comprising a 20 fold higher VLP dose (FIG. 10; compare LV03-104 5 μg group to LV01-103 100 μg group). Moreover, the low dose (5 μg), IM bivalent Norovirus vaccine produced a Norovirus-specific antibody titer similar to that induced in humans exposed to the native Norovirus (FIG. 10).

Robust IgG and IgA Elispot responses were also observed at 7 days after the first dose of the lowest dosage (5 μg) for both VLP antigens (Table 2). Notably, the antibody secreting cell (ASC) responses were biased to IgA vs. IgG and ASCs exhibited a mucosal homing (alpha 4/beta7) and chemokine (CCR10) receptor phenotype as assessed by flow cytometry (FIGS. 11A-11B; Table 3). As shown in Table 3, a greater number of ASCs exhibit mucosal homing markers (beta 7+, CD62L−) as compared to dual mucosal/peripheral homing markers (beta 7+, CD62L+). Table 4 shows the percentage of memory B cells per $10^6$ peripheral blood monocytes that respond to the VLP antigens. A larger percentage of antigen-specific memory B cells also express mucosal homing markers as compared to the dual mucosal/peripheral or peripheral homing markers. Similar responses were also observed in recipients who received the 15 μg and 50 μg doses (Tables 2-4).

TABLE 2

Day 7, Characterization of PBMC response. Approximation of Antibody Secreting Cells (ASCs)/million CD19+ cells.

| Norovirus-specific B cells | ASC/million CD19+ cells - Day 7 | | | | Vaccine Response Percent | | Vaccine Specific |
|---|---|---|---|---|---|---|---|
| | IgA GI.1 | IgG GI.1 | IgA GII.4 | IgG GII.4 | Specific to GI.1 | Specific to GII.4 | Percent of Total Circulating PBMC |
| Geometric mean A1 5 μg dose (n = 5) | 30947 | 13807 | 10947 | 3945 | 4.48% | 1.49% | 5.96% |
| Standard Deviation A1 5 μg dose | 6674 | 9780 | 3651 | 2261 | | | |
| Geometric mean A2 15 μg dose (n = 4) | 25296 | 17004 | 7108 | 4336 | 4.23% | 1.14% | 5.37% |
| Standard Deviation A2 15 μg dose | 10846 | 18770 | 6055 | 5697 | | | |
| Geometric mean A3 50 μg dose (n = 4) | 36158 | 20572 | 14103 | 2549 | 5.67% | 1.67% | 7.34% |
| Standard Deviation A3 50 μg dose | 11470 | 418 | 7627 | 2230 | | | |

TABLE 2-continued

Day 7, Characterization of PBMC response. Approximation of Antibody Secreting Cells (ASCs)/million CD19+ cells.

| Norovirus-specific B cells | ASC/million CD19+ cells - Day 7 | | | | Vaccine Response Percent | | Vaccine Specific |
|---|---|---|---|---|---|---|---|
| | IgA GI.1 | IgG GI.1 | IgA GII.4 | IgG GII.4 | Specific to GI.1 | Specific to GII.4 | Percent of Total Circulating PBMC |
| Geometric mean A4 150 μg dose (n = 4) | 34183 | 9566 | 26213 | 11310 | 4.37% | 3.75% | 8.13% |
| Standard Deviation A4 150 μg dose | 32938 | 4466 | 89769 | 15226 | | | |
| Placebo (n = 2) | 0 | 152 | 0 | 108 | 0.02% | 0.01% | 0.03% |

TABLE 3

ASC markers in vaccine and placebo recipients by flow cytometry-Day 7

| | % of Total CD19+ B cells that are CD27+ & CD38+ | % of % Total CD27+, CD38+, CCR10+_Beta 7+, CD62L− | % of % Total CD27+, CD38+, CCR10+ Beta 7+, CD62L+ | Percent Total ASC CD27+, CD38+, CCR10+, Beta 7+ CD62L(+)&(−) | Vaccine Specific Total per million cells* CD27+, CD38+, CCR10+, Beta 7+ CD62L(+)&(−) | Vaccine Specific Percent of Total* Circulating PBMC Mucosal Homing |
|---|---|---|---|---|---|---|
| Geometric mean A1 5 μg dose (n = 5) | 25.10% | 6.86% | 1.06% | 2.78% | 1656 | 0.17% |
| Standard Deviation A1 5 μg dose | 10.45 | 3.13 | 1.01 | | | |
| Geometric mean A2 15 μg dose (n = 4) | 12.99% | 16.98% | 2.43% | 4.63% | 1355 | 0.14% |
| Standard Deviation A2 15 μg dose | 9.13 | 1.56 | 0.23 | | | |
| Geometric mean A3 50 μg dose (n = 4) | 31.71% | 26.43% | 3.63% | 12.01% | 23915 | 2.39% |
| Standard Deviation A3 50 μg dose | 6.32 | 1.82 | 1.38 | | | |
| Geometric mean A4 150 μg dose (n = 4) | 33.46% | 30.06% | 5.68% | 15.74% | 31350 | 3.14% |
| Standard Deviation A4 150 μg dose | 9.86 | 2.97 | 1.70 | | | |
| Placebo (n = 2) | 1.26% | 22.00% | 0.87% | 1.20% | 5 | 0.001% |

*Assumes the majority of ASCs are norovirus-specific.

TABLE 4

Memory B cell responses in vaccine and placebo recipients-Day 7

| | % of Total CD19+ B cells that are CD27+, CD38+, CD138+ | % of % Total CD27+, CD38+, CD138+, CCR10+ Beta 7+, CD62L− | % of % Total CD27+, CD38+, CD138+, CCR10+_Beta 7+, CD62L+ | Percent Total Memory CD27+, CD38+, CD138+, CCR10+, Beta 7+ CD62L(+)&(−) | Vaccine Specific Total per million cells* CD27+, CD38+, CD138+, CCR10+, Beta 7+ CD62L(+)&(−) | Vaccine Specific Percent of Total* Circulating PBMC Mucosal Homing |
|---|---|---|---|---|---|---|
| Geometric mean A1 5 μg dose | N/D | N/D | N/D | N/D | N/D | N/D |
| Geometric mean A2 15 μg dose (n = 4) | 1.54% | 11.58% | 1.92% | 0.21% | 61 | 0.01% |
| Standard Deviation A2 15 μg dose | 1.54 | 3.94 | 0.94 | | | |
| Geometric mean A3 50 μg dose (n = 4) | 3.31% | 16.10% | 4.60% | 0.68% | 1364 | 0.14% |
| Standard Deviation A3 50 μg dose | 1.11 | 2.16 | 0.97 | | | |
| Geometric mean A4 150 μg dose (n = 4) | 1.56% | 16.90% | 8.10% | 0.39% | 778 | 0.08% |

TABLE 4-continued

Memory B cell responses in vaccine and placebo recipients-Day 7

| | % of Total CD19+ B cells that are CD27+, CD38+, CD138+ | % of % Total CD27+, CD38+, CD138+, CCR10+ Beta 7+, CD62L− | % of % Total CD27+, CD38+, CD138+, CCR10+_Beta 7+, CD62L+ | Percent Total Memory CD27+, CD38+, CD138+, CCR10+, Beta 7+ CD62L(+)&(−) | Vaccine Specific Total per million cells* CD27+, CD38+, CD138+, CCR10+, Beta 7+ CD62L(+)&(−) | Vaccine Specific Percent of Total* Circulating PBMC Mucosal Homing |
|---|---|---|---|---|---|---|
| Standard Deviation A4 | 0.22 | 3.26 | 4.57 | | | |
| 150 µg dose Placebo (n = 1) | 0.10% | 12.50% | 0.00% | 0.01% | 0 | 0% |

*Assumes the majority of ASCs are norovirus-specific.

In the absence of an available direct viral neutralization assay due to the inability to culture Norovirus in vitro, functional assays which serve as substitutes for viral neutralization assays were conducted to measure functional antibodies in vaccinees.

Using the carbohydrate H antigen blocking activity assay described above, the inhibition of GI.1 VLP binding to H antigen mediated by vaccine-induced serum antibodies was measured. Data are presented as geometric mean fold rise (GMFR) and seroresponse (4-fold rise) in Table 5, and as geometric mean titer (GMT) in Table 6. Surprisingly, after just one intramuscular injection of the vaccine formulation, significant carbohydrate blocking activity was observed in all dose groups; in fact, the administration of a second dose of vaccine did not significantly increase blocking activity compared to post-dose 1 levels. The inhibition of binding activity was maintained throughout the testing period, up to 56 days post dose 1.

TABLE 5

Carbohydrate Blocking Activity (HBGA BT50), Anti-Norovirus GI.1 Geometric Mean Fold Rise (GMFR) and Seroresponse (4-Fold Rise)

| | Study Day | | | | | | | | | | | |
|---|---|---|---|---|---|---|---|---|---|---|---|---|
| | 7 Days Post Dose 1 | | | 21 Days Post Dose 1 | | | 28 Days Post Dose 1 (Pre-Dose 2) | | | 7 Days Post Dose 2 (35 Days Post Dose 1) | | | 28 Days Post Dose 2 (56 Days Post Dose 1) | |
| Treatment Group | N | GMFR (95% CI) | 4-Fold Rise (95% CI) | N | GMFR (95% CI) | 4-Fold Rise (95% CI) | N | GMFR (95% CI) | 4-Fold Rise (95% CI) | N | GMFR (95% CI) | 4-Fold Rise (95% CI) | N | GMFR (95% CI) | 4-Fold Rise (95% CI) |
| 5/5 mcg VLP Vaccine | 9 | 26.6 (8.3, 85.1) | 88.9 (51.8, 99.7) | 9 | 25.1 (8.9, 70.3) | 88.9 (51.8, 99.7) | 9 | 19.7 (8.2, 47.1) | 100.0 (66.4, 100.0) | 9 | 20 (7.7, 51.7) | 88.9 (51.8, 99.7) | 9 | 16.6 (5.7, 48.1) | 77.8 (40.0, 97.2) |
| 15/15 mcg VLP Vaccine | 8 | 33.2 (13.6, 80.8) | 100.0 (63.1, 100.0) | 8 | 25.5 (10.5, 61.8) | 100.0 (63.1, 100.0) | 8 | 18.5 (8.4, 40.6) | 100.0 (63.1, 100.0) | 7 | 22.2 (8.8, 56) | 100.0 (59.0, 100.0) | 7 | 8.4 (2.4, 29.6) | 57.1 (18.4, 90.1) |
| 50/50 mcg VLP Vaccine | 10 | 38.6 (18.3, 81.6) | 100.0 (69.2, 100.0) | 10 | 27.9 (13.4, 58) | 100.0 (69.2, 100.0) | 10 | 20.9 (10, 43.5) | 100.0 (69.2, 100.0) | 10 | 19 (9.9, 36.4) | 100.0 (69.2, 100.0) | 9 | 10.2 (4.6, 22.8) | 77.8 (40.0, 97.2) |
| 150/150 mcg VLP Vaccine | 7 | 30.6 (16.3, 57.6) | 100.0 (59.0, 100.0) | 8 | 19.4 (13.1, 28.5) | 100.0 (63.1, 100.0) | 8 | 16.3 (11.7, 22.6) | 100.0 (63.1, 100.0) | 8 | 18.8 (12.8, 27.5) | 100.0 (63.1, 100.0) | 8 | 23.8 (17, 33.3) | 100.0 (63.1, 100.0) |
| Placebo | 8 | 0.9 (0.8, 1) | 0.0 (0.0, 36.9) | 8 | 0.8 (0.7, 1.1) | 0.0 (0.0, 36.9) | 8 | 0.8 (0.6, 1.1) | 0.0 (0.0, 36.9) | 8 | 0.8 (0.7, 1.1) | 0.0 (0.0, 36.9) | 8 | 0.6 (0.3, 1.2) | 0.0 (0.0, 36.9) |

Results based on all subjects receiving both doses of study product.
Two subjects' data points are excluded due to a possible mix-up of specimens; one of these data points is a baseline specimen resulting in the subject not having fold rise data available for any time point.

TABLE 6

Carbohydrate Blocking Activity (HBGA BT50), Anti-Norovirus GI.1 Geometric Mean Titer (GMT)

| | Study Day | | | | | | | | | | | |
|---|---|---|---|---|---|---|---|---|---|---|---|---|
| | Pre-Dose 1 | | 7 Days Post Dose 1 | | 21 Days Post Dose 1 | | 28 Days Post Dose 1 (Pre-Dose 2) | | 7 Days Post Dose 2 (35 Days Post Dose 1) | | 28 Days Post Dose 2 (56 Days Post Dose 1) | |
| Treatment Group | N | GMT (95% CI) | N | GMT (95% CI) | N | GMT (95% CI) | N | GMT (95% CI) | N | GMT (95% CI) | N | GMT (95% CI) |
| 5/5 mcg VLP Vaccine | 9 | 28.9 (12.7, 65.9) | 9 | 768.5 (344.1, 1716) | 9 | 723.7 (398.1, 1316) | 9 | 568 (321.8, 1003) | 9 | 577.1 (351.2, 948.3) | 9 | 478.3 (293.3, 780.1) |
| 15/15 mcg VLP Vaccine | 8 | 24.9 (12.7, 48.7) | 8 | 826.1 (524.9, 1300) | 8 | 634.3 (285.9, 1407) | 8 | 459.8 (225.3, 938.6) | 7 | 610.3 (354.6, 1050) | 7 | 230.9 (105.2, 506.7) |

TABLE 6-continued

Carbohydrate Blocking Activity (HBGA BT50), Anti-Norovirus GI.1 Geometric Mean Titer (GMT)

| | Study Day | | | | | | | | | | | |
|---|---|---|---|---|---|---|---|---|---|---|---|---|
| | Pre-Dose 1 | | 7 Days Post Dose 1 | | 21 Days Post Dose 1 | | 28 Days Post Dose 1 (Pre-Dose 2) | | 7 Days Post Dose 2 (35 Days Post Dose 1) | | 28 Days Post Dose 2 (56 Days Post Dose 1) | |
| Treatment Group | N | GMT (95% CI) | N | GMT (95% CI) | N | GMT (95% CI) | N | GMT (95% CI) | N | GMT (95% CI) | N | GMT (95% CI) |
| 50/50 mcg VLP Vaccine | 10 | 17.3 (9.9, 30.3) | 10 | 669.2 (329.1, 1361) | 10 | 483.7 (258.7, 904.2) | 10 | 362.4 (192.9, 680.7) | 10 | 328.9 (191.9, 563.8) | 9 | 184 (97.2, 348.3) |
| 150/150 mcg VLP Vaccine | 8 | 15.5 (11.1, 21.8) | 7 | 435 (262.5, 720.8) | 8 | 300.7 (173.9, 520) | 8 | 252.7 (146.7, 435.2) | 8 | 291.5 (171.5, 495.4) | 8 | 369.7 (233.8, 584.6) |
| Placebo | 8 | 29 (9.1, 92.8) | 9 | 24.6 (9.8, 62.1) | 9 | 22.5 (8.8, 57.3) | 9 | 22.2 (8.9, 55.5) | 8 | 24.6 (8.4, 72.6) | 8 | 18.3 (10.1, 33.3) |

Results based on all subjects receiving both doses of study product.
Two subjects' data points are excluded due to a possible mix-up of specimens.

Similarly, carbohydrate blocking activity of serum antibodies against GII.4 VLPs was measured. A significant response was observed in all dosing groups as measured by GMFR and seroresponse (Table 7) as well as GMT (Table 8). Similar to the antibody-mediated blocking of GI.1 binding described above, robust blocking of GII.4 VLP carbohydrate binding activity was detected after just one dose, and a second dose did not appear to enhance the blocking activity.

TABLE 7

Carbohydrate Blocking Activity (HBGA BT50), Anti-Norovirus GII.4 Geometric Mean Fold Rise (GMFR) and Seroresponse (4-Fold Rise)

| | Study Day | | | | | | | | | | | | | | |
|---|---|---|---|---|---|---|---|---|---|---|---|---|---|---|---|
| | 7 Days Post Dose 1 | | | 21 Days Post Dose 1 | | | 28 Days Post Dose 1 (Pre-Dose 2) | | | 7 Days Post Dose 2 (35 Days Post Dose 1) | | | 28 Days Post Dose 2 (56 Days Post Dose 1) | | |
| Treatment Group | N | GMFR (95% CI) | 4-Fold Rise (95% CI) | N | GMFR (95% CI) | 4-Fold Rise (95% CI) | N | GMFR (95% CI) | 4-Fold Rise (95% CI) | N | GMFR (95% CI) | 4-Fold Rise (95% CI) | N | GMFR (95% CI) | 4-Fold Rise (95% CI) |
| 5/5 mcg VLP Vaccine | 9 | 5 (1.6, 16.1) | 33.3 (7.5, 70.1) | 9 | 5.9 (1.7, 20.3) | 55.6 (21.2, 86.3) | 9 | 4.7 (1.4, 15.7) | 44.4 (13.7, 78.8) | 9 | 4.7 (1.6, 13.8) | 44.4 (13.7, 78.8) | 9 | 5 (1.6, 15.9) | 55.6 (21.2, 86.3) |
| 15/15 mcg VLP Vaccine | 8 | 11 (2.7, 45.3) | 62.5 (24.5, 91.5) | 8 | 9.2 (3, 27.9) | 62.5 (24.5, 91.5) | 8 | 7.4 (2.5, 21.8) | 62.5 (24.5, 91.5) | 7 | 7 (2.1, 23) | 57.1 (18.4, 90.1) | 7 | 5.6 (2.3, 14) | 57.1 (18.4, 90.1) |
| 50/50 mcg VLP Vaccine | 10 | 18.6 (4.9, 70.8) | 70.0 (34.8, 93.3) | 10 | 12.2 (3.8, 39.4) | 70.0 (34.8, 93.3) | 10 | 8.4 (2.9, 24.1) | 70.0 (34.8, 93.3) | 10 | 8.7 (2.9, 26.1) | 70.0 (34.8, 93.3) | 9 | 5.2 (2.2, 12) | 66.7 (29.9, 92.5) |
| 150/150 mcg VLP Vaccine | 7 | 10.1 (2, 51.8) | 57.1 (18.4, 90.1) | 8 | 5.5 (1.9, 16.5) | 50.0 (15.7, 84.3) | 8 | 4.4 (1.6, 12.2) | 50.0 (15.7, 84.3) | 8 | 4.3 (1.7, 10.7) | 37.5 (8.5, 75.5) | 8 | 3.1 (1.3, 7.2) | 25.0 (3.2, 65.1) |
| Placebo | 8 | 1 (0.9, 1.1) | 0.0 (0.0, 36.9) | 8 | 1.1 (1, 1.3) | 0.0 (0.0, 36.9) | 8 | 1.3 (0.9, 2.1) | 12.5 (0.3, 52.7) | 8 | 1.8 (0.5, 6.7) | 12.5 (0.3, 52.7) | 8 | 2 (0.7, 6.1) | 12.5 (0.3, 52.7) |

Results based on all subjects receiving both doses of study product.
Two subjects' data points are excluded due to a possible mix-up of specimens; one of these data points is a baseline specimen resulting in the subject not having fold rise data available for any time point.

TABLE 8

Carbohydrate Blocking Activity (HBGA BT50), Anti-Norovirus GII.4 Geometric Mean Titer (GMT)

| | Study Day | | | | | | | | | | | |
|---|---|---|---|---|---|---|---|---|---|---|---|---|
| | Pre-Dose 1 | | 7 Days Post Dose 1 | | 21 Days Post Dose 1 | | 28 Days Post Dose 1 (Pre-Dose 2) | | 7 Days Post Dose 2 (35 Days Post Dose 1) | | 28 Days Post Dose 2 (56 Days Post Dose 1) | |
| Treatment Group | N | GMT (95% CI) | N | GMT (95% CI) | N | GMT (95% CI) | N | GMT (95% CI) | N | GMT (95% CI) | N | GMT (95% CI) |
| 5/5 mcg VLP Vaccine | 9 | 40.3 (18, 90) | 9 | 202.1 (106.3, 384.3) | 9 | 236.9 (133.4, 420.6) | 9 | 189.7 (108.6, 331.3) | 9 | 188.7 (118.7, 300.1) | 9 | 201.6 (116.4, 349.5) |

TABLE 8-continued

Carbohydrate Blocking Activity (HBGA BT50), Anti-Norovirus GII.4 Geometric Mean Titer (GMT)

| Treatment Group | Pre-Dose 1 | | 7 Days Post Dose 1 | | 21 Days Post Dose 1 | | 28 Days Post Dose 1 (Pre-Dose 2) | | 7 Days Post Dose 2 (35 Days Post Dose 1) | | 28 Days Post Dose 2 (56 Days Post Dose 1) | |
|---|---|---|---|---|---|---|---|---|---|---|---|---|
| | N | GMT (95% CI) | N | GMT (95% CI) | N | GMT (95% CI) | N | GMT (95% CI) | N | GMT (95% CI) | N | GMT (95% CI) |
| 15/15 mcg VLP Vaccine | 8 | 23.7 (12.8, 43.8) | 8 | 260.1 (95.1, 711.1) | 8 | 218.1 (104.2, 456.3) | 8 | 175.4 (82.7, 372) | 7 | 182.3 (89.1, 372.8) | 7 | 146.3 (92.4, 231.5) |
| 50/50 mcg VLP Vaccine | 10 | 28.4 (13.1, 61.5) | 10 | 527.2 (271.1, 1025) | 10 | 345.2 (195.5, 609.6) | 10 | 238.3 (139.4, 407.3) | 10 | 246.5 (138.7, 438.2) | 9 | 160.2 (107.4, 238.8) |
| 150/150 mcg VLP Vaccine | 8 | 63 (24.8, 160.4) | 7 | 721.8 (344.6, 1512) | 8 | 347.7 (186.1, 649.5) | 8 | 277 (145.6, 527) | 8 | 267.9 (158.7, 452.2) | 8 | 193.5 (121.6, 308.2) |
| Placebo | 8 | 24.1 (12.9, 45) | 9 | 22.8 (12.6, 41.6) | 9 | 24.9 (12.7, 48.7) | 9 | 29.1 (15.1, 56.1) | 8 | 44 (12.6, 154.2) | 8 | 48.2 (16.7, 139.5) |

Results based on all subjects receiving both doses of study product.
Two subjects' data points are excluded due to a possible mix-up of specimens.

Hemagglutination Inhibition assays (HAI) were also utilized to test the response of serum antibodies from vaccinated subjects against target Norovirus VLP antigens. Similar to carbohydrate H antigen binding studies, just one dose of VLP vaccine induced antibodies that inhibited hemagglutination in all dosing groups, as measured by GMFR (Table 9), 4-fold rise (Table 9), and GMT (Table 10). Though the level of inhibition of hemagglutination was maintained through the last day tested (28 days post dose 2, 56 days post dose 1), the second dose of VLP vaccine did not appear to enhance vaccine-induced antibody-mediated inhibition of hemagglutination.

TABLE 9

Hemagglutination Inhibition Assay Anti-Norovirus GI.1 Geometric Mean Fold Rise (GMFR) and Seroresponse (4-Fold Rise)

| Treatment Group | 7 Days Post Dose 1 | | | 21 Days Post Dose 1 | | | 28 Days Post Dose 1 (Pre-Dose 2) | | | 7 Days Post Dose 2 (35 Days Post Dose 1) | | | 28 Days Post Dose 2 (56 Days Post Dose 1) | | |
|---|---|---|---|---|---|---|---|---|---|---|---|---|---|---|---|
| | N | GMFR (95% CI) | 4-Fold Rise (95% CI) | N | GMFR (95% CI) | 4-Fold Rise (95% CI) | N | GMFR (95% CI) | 4-Fold Rise (95% CI) | N | GMFR (95% CI) | 4-Fold Rise (95% CI) | N | GMFR (95% CI) | 4-Fold Rise (95% CI) |
| 5/5 mcg VLP Vaccine | 9 | 5.4 (3, 9.8) | 77.8 (40.0, 97.2) | 9 | 7 (4.6, 10.7) | 88.9 (51.8, 99.7) | 9 | 6.1 (4.1, 9.3) | 88.9 (51.8, 99.7) | 9 | 6 (3.7, 9.5) | 77.8 (40.0, 97.2) | 9 | 6.3 (3.9, 10.3) | 88.9 (51.8, 99.7) |
| 15/15 mcg VLP Vaccine | 8 | 8.9 (4.4, 18) | 100.0 (63.1, 100.0) | 8 | 9.5 (4, 22.5) | 87.5 (47.3, 99.7) | 8 | 7.1 (3.1, 16.1) | 75.0 (34.9, 96.8) | 7 | 8.5 (4.1, 17.7) | 85.7 (42.1, 99.6) | 7 | 8.1 (4.4, 15.2) | 100.0 (59.0, 100.0) |
| 50/50 mcg VLP Vaccine | 10 | 22.4 (11.6, 43) | 100.0 (69.2, 100.0) | 10 | 16.7 (9.3, 29.8) | 100.0 (69.2, 100.0) | 10 | 13.9 (8.1, 24) | 100.0 (69.2, 100.0) | 10 | 14.5 (9.3, 22.7) | 100.0 (69.2, 100.0) | 9 | 11.8 (6.3, 21.9) | 100.0 (66.4, 100.0) |
| 150/150 mcg VLP Vaccine | 7 | 12.6 (5.7, 28) | 85.7 (42.1, 99.6) | 8 | 11.1 (6.4, 19.3) | 100.0 (63.1, 100.0) | 8 | 8.4 (5, 14) | 100.0 (63.1, 100.0) | 8 | 8.4 (5, 14) | 100.0 (63.1, 100.0) | 8 | 7.3 (4.5, 11.9) | 100.0 (63.1, 100.0) |
| Placebo | 8 | 1 (0.8, 1.2) | 0.0 (0.0, 36.9) | 8 | 1 (0.9, 1.2) | 0.0 (0.0, 36.9) | 8 | 1 (0.9, 1.1) | 0.0 (0.0, 36.9) | 8 | 0.9 (0.7, 1.1) | 0.0 (0.0, 36.9) | 8 | 1 (0.8, 1.2) | 0.0 (0.0, 36.9) |

Results based on all subjects receiving both doses of study product.

Two subjects' data points are excluded due to a possible mix-up of specimens; one of these data points is a baseline specimen resulting in the subject not having fold rise data available for any time point.

TABLE 10

Hemagglutination Inhibition Assay Anti-Norovirus GI.1 Geometric Mean Titer (GMT)

| | | Study Day | | | | | | | | | | |
|---|---|---|---|---|---|---|---|---|---|---|---|---|
| | | Pre-Dose 1 | | 7 Days Post Dose 1 | | 21 Days Post Dose 1 | | 28 Days Post Dose 1 (Pre-Dose 2) | | 7 Days Post Dose 2 (35 Days Post Dose 1) | | 28 Days Post Dose 2 (56 Days Post Dose 1) |
| Treatment Group | N | GMT (95% CI) | N | GMT (95% CI) | N | GMT (95% CI) | N | GMT (95% CI) | N | GMT (95% CI) | N | GMT (95% CI) |
| 5/5 mcg VLP Vaccine | 9 | 26.4 (14.1, 49.4) | 9 | 143.5 (53.6, 383.8) | 9 | 185.3 (88.6, 387.6) | 9 | 162.1 (83.3, 315.6) | 9 | 157 (80.3, 307.1) | 9 | 167.4 (88.4, 316.8) |
| 15/15 mcg VLP Vaccine | 8 | 11.9 (6.1, 23.4) | 8 | 105.3 (56.1, 197.6) | 8 | 113.1 (42.5, 301.3) | 8 | 84.2 (31.1, 227.6) | 7 | 103.3 (43.3, 246.6) | 7 | 99.2 (46.9, 209.7) |
| 50/50 mcg VLP Vaccine | 10 | 7.2 (5.3, 9.6) | 10 | 160 (79.4, 322.6) | 10 | 119.2 (60.4, 235.1) | 10 | 99.7 (51.8, 191.8) | 10 | 103.8 (58.4, 184.5) | 9 | 81.1 (38.8, 169.5) |
| 150/150 mcg VLP Vaccine | 8 | 9.2 (7.5, 11.3) | 7 | 114.1 (50.9, 255.7) | 8 | 101.6 (62, 166.4) | 8 | 77.2 (51.8, 115) | 8 | 77.2 (51.8, 115) | 8 | 67.3 (44.7, 101.3) |
| Placebo | 8 | 16.8 (10.1, 28.1) | 9 | 16.6 (11.7, 23.7) | 9 | 16.1 (10.7, 24.1) | 9 | 16.6 (11, 25) | 8 | 15.4 (10, 23.7) | 8 | 16.2 (10.8, 24.4) |

Results based on all subjects receiving both doses of study product.
Two subjects' data points are excluded due to a possible mix-up of specimens.

Inhibition of hemagglutination was also achieved when the target VLP was a mismatched virus. Vaccine-induced serum antibodies inhibited hemagglutination by a Houston virus strain VLP, as measured by GMFR and seroresponse (Table 11) as well as GMT (Table 12). In this case, the higher VLP vaccine doses afforded stronger responses, particularly as measured by 4-fold rise or GMT. GMFR and 4-fold rise were also significantly increased when the target VLP was the 2003 Cincinnati virus strain, as measured just 7 days post dose 1 (Table 13).

TABLE 11

Hemagglutination Inhibition Assay (Houston Virus Strain VLP), Anti-Norovirus GII.4 Geometric Mean Fold Rise (GMFR) and Seroresponse (4-Fold Rise)

| | | Study Day | | | | | | | | | | | | | |
|---|---|---|---|---|---|---|---|---|---|---|---|---|---|---|---|
| | | 7 Days Post Dose 1 | | | 21 Days Post Dose 1 | | | 28 Days Post Dose 1 (Pre-Dose 2) | | | 7 Days Post Dose 2 (35 Days Post Dose 1) | | | 28 Days Post Dose 2 (56 Days Post Dose1) | |
| Treatment Group | N | GMFR (95% CI) | 4-Fold Rise (95% CI) | N | GMFR (95% CI) | 4-Fold Rise (95% CI) | N | GMFR (95% CI) | 4-Fold Rise (95% CI) | N | GMFR (95% CI) | 4-Fold Rise (95% CI) | N | GMFR (95% CI) | 4-Fold Rise (95% CI) |
| 5/5 mcg VLP Vaccine | 9 | 1.2 (1, 1.5) | 0.0 (0.0, 33.6) | 9 | 1.3 (0.9, 1.7) | 0.0 (0.0, 33.6) | 9 | 1.3 (0.9, 1.7) | 0.0 (0.0, 33.6) | 9 | 1.3 (1, 1.7) | 0.0 (0.0, 33.6) | 9 | 1.3 (1, 1.6) | 0.0 (0.0, 33.6) |
| 15/15 mcg VLP Vaccine | 8 | 1.7 (0.9, 3) | 12.5 (0.3, 52.7) | 8 | 1.6 (1.1, 2.4) | 12.5 (0.3, 52.7) | 8 | 1.5 (1.1, 2.2) | 0.0 (0.0, 36.9) | 7 | 1.5 (1, 2.2) | 0.0 (0.0, 41.0) | 7 | 1.6 (1.1, 2.4) | 0.0 (0.0, 41.0) |
| 50/50 mcg VLP Vaccine | 10 | 2 (0.9, 4.3) | 10.0 (0.3, 44.5) | 10 | 1.6 (0.8, 3.1) | 10.0 (0.3, 44.5) | 10 | 1.7 (0.9, 3.1) | 10.0 (0.3, 44.5) | 10 | 1.5 (0.9, 2.4) | 10.0 (0.3, 44.5) | 9 | 1.3 (0.8, 2) | 11.1 (0.3, 48.2) |
| 150/150 mcg VLP Vaccine | 7 | 4.3 (1.5, 12.4) | 57.1 (18.4, 90.1) | 8 | 2.6 (1.2, 5.8) | 50.0 (15.7, 84.3) | 8 | 1.9 (1.1, 3.3) | 12.5 (0.3, 52.7) | 8 | 1.9 (1.1, 3.5) | 12.5 (0.3, 52.7) | 8 | 1.7 (1.1, 2.6) | 12.5 (0.3, 52.7) |
| Placebo | 8 | 1 (0.9, 1.1) | 0.0 (0.0, 36.9) | 8 | 1.1 (0.9, 1.3) | 0.0 (0.0, 36.9) | 8 | 1.1 (1, 1.2) | 0.0 (0.0, 36.9) | 8 | 1.2 (0.8, 1.9) | 12.5 (0.3, 52.7) | 8 | 1.1 (0.7, 1.8) | 12.5 (0.3, 52.7) |

Results based on all subjects receiving both doses of study product.

Two subjects' data points are excluded due to a possible mix-up of specimens; one of these data points is a baseline specimen resulting in the subject not having fold rise data available for any time point.

TABLE 12

Hemagglutination Inhibition Assay (Houston Virus Strain VLP), Anti-Norovirus GII.4 Geometric Mean Titer (GMT)

| | Study Day | | | | | | | | | | | |
|---|---|---|---|---|---|---|---|---|---|---|---|---|
| | Pre-Dose 1 | | 7 Days Post Dose 1 | | 21 Days Post Dose 1 | | 28 Days Post Dose 1 (Pre-Dose 2) | | 7 Days Post Dose 2 (35 Days Post Dose 1) | | 28 Days Post Dose 2 (56 Days Post Dose 1) | |
| Treatment Group | N | GMT (95% CI) | N | GMT (95% CI) | N | GMT (95% CI) | N | GMT (95% CI) | N | GMT (95% CI) | N | GMT (95% CI) |
| 5/5 mcg VLP Vaccine | 9 | 143.5 (97.9, 210.3) | 9 | 177.4 (122.7, 256.5) | 9 | 180.8 (114.4, 285.6) | 9 | 180.8 (114.4, 285.6) | 9 | 189.1 (119.2, 299.9) | 9 | 180.8 (122.7, 266.3) |
| 15/15 mcg VLP Vaccine | 8 | 129.8 (86.4, 194.9) | 8 | 218.3 (129.2, 368.8) | 8 | 207.5 (134.8, 319.3) | 8 | 200.2 (132.8, 301.7) | 7 | 169.5 (114.1, 252) | 7 | 187.2 (119.1, 294.2) |
| 50/50 mcg VLP Vaccine | 10 | 161.9 (119.7, 219) | 10 | 323.8 (156.5, 669.8) | 10 | 252.5 (130.4, 489.2) | 10 | 273.9 (150.9, 497.2) | 10 | 242.5 (150.2, 391.5) | 9 | 195.2 (125, 304.9) |
| 150/150 mcg VLP Vaccine | 8 | 210.6 (108.8, 407.5) | 7 | 853.5 (297.4, 2449) | 8 | 546.2 (237.6, 1255) | 8 | 406.3 (201.5, 819.1) | 8 | 406.3 (180.3, 915.4) | 8 | 354.1 (184.6, 679.5) |
| Placebo | 8 | 148.9 (73.8, 300.3) | 9 | 150.1 (80.1, 281.1) | 9 | 157 (77.9, 316.5) | 9 | 167.4 (91.4, 306.4) | 8 | 183.6 (95, 354.5) | 8 | 162.4 (88.5, 297.9) |

Results based on all subjects receiving both doses of study product.
Two subjects' data points are excluded due to a possible mix-up of specimens.

TABLE 13

Inhibition of Hemagglutination in placebo versus 50/50 µg VLP vaccine
Hemagglutination Inhibition Assay (2003 Cincinnati Virus Strain
VLP), Anti-Norovirus GII.4 Geometric Mean Fold Rise (GMFR)
and Geometric Seroresponse (4-Fold Rise)
Results by Treatment Group 7 Days Post Dose 1

| Treatment Group | N | GMFR (95% CI) | 4-Fold Rise (95% CI) |
|---|---|---|---|
| Placebo | 2 | 1.0 (0.6, 1.8) | 0.0 (0.0, 84.2) |
| 50/50 µg VLP Vaccine | 10 | 4.4 (1.6, 11.9) | 50.0 (18.7, 81.3) |

The results from this study demonstrated that the Bivalent IM Norovirus VLP vaccine was generally well tolerated. The immunogenicity data suggested that a single vaccine dose may be sufficient to protect seropositive human adults. The results from the carbohydrate blocking activity and hemagglutination inhibition assays provided further evidence that a single vaccine dose induced serum antibodies with potent anti-Norovirus activity. The magnitude and rapidity of the observed immune responses following a single parenteral dose in humans were dramatic when compared to earlier immune responses reported by multiple nasal VLP vaccine administrations at much higher VLP dosages (El Kamary et al. (2010) J Infect Dis, Vol. 202(11): 1649-1658). These responses were also superior to those induced by orally administered Norovirus VLPs (Tacket et al. (2003) Clin Immunol 108:241-247; Ball et al. (1999, Gastroenterology 117:40-48) as well as those induced by Norovirus VLPs produced by transgenic plants (Tacket et al. (2000) J Infect Dis 182:302-305). In particular, this intramuscular vaccine formulation produced anamnestic responses within seven days of immunization and maximal serum antibody responses were observed after a single dose, including a significant IgA response and functional carbohydrate blocking activity and hemagglutination inhibition activity. Thus, this Norovirus bivalent vaccine induced a strong, protective immune response in humans that was superior to immune responses induced by any currently available Norovirus vaccine.

Example 2. Dose Escalation, Safety and Immunogenicity Study of Intramuscular Norovirus Bivalent Virus-Like-Particle (VLP) Vaccine in Humans (LV03-104 Study)

The following example provides the remaining planned portion of the clinical study described in Example 1, wherein a randomized, multi-site, dose-escalation study is conducted in adults ≥18 years of age of the safety and immunogenicity of four dosage levels of an intramuscular (IM) Norovirus Bivalent VLP Vaccine adjuvanted with monophosphoryl lipid A (MPL) and aluminum hydroxide (AlOH), compared to placebo. Subjects will receive two doses of the vaccine or placebo, by intramuscular (IM) injection, 28 days apart using a 1.5 inch (38 mm) needle. This example is intended to further illustrate the principles of the present invention.

Cohort A has completed enrollment in the study and was described above in Example 1. Cohort B contains ~20 subjects 50-64 years of age. Cohort C contains ~30 subjects 65-85 years of age. Approximately 98 subjects are enrolled in the study as a whole.

In Cohort B, ~20 subjects 50-64 years of age are enrolled and randomized 1:1 to receive vaccine (N=10) or placebo (N=10). After the 7-day post Dose 2 safety data (Study Day 35) are available for review from subjects in Cohort B, subjects in Cohort C are eligible to receive their initial dose. In Cohort C, ~30 subjects 65 to 85 years of age are enrolled and randomized 1:1:1 to receive vaccine adjuvanted with MPL and AlOH (N=10), or vaccine adjuvanted with AlOH alone, i.e. no MPL (N=10), or placebo (N=10). The antigen concentrations of the norovirus VLPs and of the AlOH in the two vaccine formulations to be evaluated in Cohort C are identical; only the presence or absence of MPL is different.

The Norovirus Bivalent VLP Vaccine contains genogroup I, genotype 1 (GI.1) and genogroup II, genotype IV (GII.4) VLPs as the antigens, and Monophosphoryl Lipid A (MPL) and aluminum hydroxide (AlOH) as adjuvants, sodium chloride (NaCl) and L-histidine (L-His) as buffer (pH 6.3-6.7), ethanol and water for injection. The GII.4 VLPs comprised a capsid sequence of SEQ ID NO: 1, which was derived from three GII.4 strains.

The single dosage of vaccine selected for further evaluation in Cohorts B and C is the lowest dosage in Cohort A that results in the most robust and reproducible immune response that is also generally well tolerated. The Day 56 safety and immunogenicity data from subjects in Cohort A is reviewed by the CSM/SMC and the bivalent dosage is selected for evaluation in Cohorts B and C.

The subjects keep a daily memory aid of solicited symptoms including four local injection site reactions, such as pain, tenderness, redness, and swelling, and 10 systemic signs or symptoms including daily oral temperature, headache, fatigue, muscle aches, chills, joint aches and gastrointestinal symptoms of nausea, vomiting, diarrhea, abdominal cramps/pain for Days 0 through 7 after each dose of IM Norovirus Bivalent VLP Vaccine or control. The redness and swelling at the injection site are measured and recorded daily for 7 days after each injection.

Interim medical histories are obtained at each follow-up visit on Days 7+3, 21+3, 28+3, 35+3, 56+7, 180+14, and 393+14 and at the follow-up telephone call on Day 265+14; subjects are queried about interim illness, doctor's visits, any serious adverse events (SAEs), and onset of any significant new medical conditions. Subjects have a CBC with WBC differential and platelet count, and serum BUN, creatinine, glucose, AST, and ALT assessed at screening and on Days 21 and 35 (~7 days after each dose) to assess continuing eligibility and safety, respectively.

Blood from subjects is collected before vaccination on Day 0 and on Days 7+3, 21+3, 28+3, 35+3, 56+7, 180+14, and 393+14 to measure serum antibodies (IgG, IgA, and IgM separately and combined) to IM Norovirus Bivalent VLP Vaccine by enzyme-linked immunosorbent assays (ELISA). Serum carbohydrate blocking activity and serum HAI antibodies are also measured.

The methods described above for Cohort A are used to analyze the blood samples collected from immunized individuals or individuals receiving the placebo. The results of the study will be employed in the development of a clinical protocol for administration of the vaccine formulations of the invention.

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein, will become apparent to those skilled in the art from the foregoing description and accompanying drawings using no more than routine experimentation. Such modifications and equivalents are intended to fall within the scope of the appended claims.

All publications, patents and patent applications mentioned in this specification are herein incorporated by reference into the specification to the same extent as if each individual publication, patent or patent application was specifically and individually indicated to be incorporated herein by reference.

Citation or discussion of a reference herein shall not be construed as an admission that such is prior art to the present invention.

The invention claimed is:

1. A method of eliciting protective immunity against Norovirus in a human comprising administering parenterally to the human no more than a single dose of a vaccine composition, said composition comprising
   (i) genogroup I Norovirus virus-like particles (VLPs), wherein said genogroup I Norovirus VLPs comprise a capsid protein derived from a genogroup I viral strain, and
   (ii) genogroup II Norovirus VLPs, wherein said genogroup II Norovirus VLPs comprise a capsid protein derived from a genogroup II viral strain,
   wherein said genogroup I Norovirus VLPs and genogroup II Norovirus VLPs are present in the composition in different amounts, wherein said composition comprises about 15 µg to 50 µg of genogroup I Norovirus VLPs and about 50 µg to 150 µg of genogroup II Norovirus VLPs,
   wherein said composition induces at least a three-fold increase in Norovirus-specific serum antibody titer as compared to the titer in the human prior to administration of the composition.

2. The method of claim 1, wherein the composition comprises about 15 µg of said genogroup I Norovirus VLPs.

3. The method of claim 1, wherein the composition comprises about 50 µg of said genogroup II Norovirus VLPs.

4. The method of claim 1, wherein the composition comprises about 15 µg of said genogroup I Norovirus VLPs and about 50 µg of said genogroup II Norovirus VLPs.

5. The method of claim 1, wherein the composition induces at least a six-fold increase in Norovirus-specific serum antibody titer as compared to the titer in the human prior to administration of the composition.

6. The method of claim 1, wherein said Norovirus VLPs are monovalent VLPs or multivalent VLPs.

7. The method of claim 1, wherein said genogroup I Norovirus VLPs are Norwalk virus VLPs and said genogroup II Norovirus VLPs are VLPs generated from expression of a consensus sequence of genogroup II Norovirus.

8. The method of claim 1, wherein the composition further comprises at least one adjuvant.

9. The method of claim 8, wherein said at least one adjuvant is a toll-like receptor agonist.

10. The method of claim 8, wherein the adjuvant is selected from monophosphoryl lipid A and aluminum hydroxide.

11. The method of claim 1, wherein said composition further comprises a buffer.

12. The method of claim 11, wherein said buffer is selected from the group consisting of L-histidine, imidazole, succinic acid, tris, and citric acid.

13. The method of claim 1, wherein the vaccine composition is administered to the human by an intravenous, subcutaneous, intradermal, or intramuscular route of administration.

14. The method of claim 13, wherein the vaccine composition is administered to the human by an intramuscular route of administration.

15. The method of claim 1, wherein the vaccine composition is formulated as a liquid.

16. The method of claim 1, wherein the increase in Norovirus-specific antibody titer is induced within seven days of administration of the single dose of the composition.

17. The method of claim 1, wherein said vaccine composition confers protection from one or more symptoms of Norovirus infection.

18. The method of claim 8, wherein said at least one adjuvant is an aluminum hydroxide.

* * * * *

UNITED STATES PATENT AND TRADEMARK OFFICE
CERTIFICATE OF CORRECTION

| | |
|---|---|
| PATENT NO. | : 10,675,341 B2 |
| APPLICATION NO. | : 15/836030 |
| DATED | : June 9, 2020 |
| INVENTOR(S) | : Charles Richardson et al. |

It is certified that error appears in the above-identified patent and that said Letters Patent is hereby corrected as shown below:

On the Title Page

Item (72) Inventors:
Add --Robert F. Bargatze, Cambridge, MA (US)
Paul Mendelman, Cambridge, MA (US)--

Signed and Sealed this
Twenty-sixth Day of March, 2024

Katherine Kelly Vidal
*Director of the United States Patent and Trademark Office*

SEQUENCE LISTING

```
<160> NUMBER OF SEQ ID NOS: 1

<210> SEQ ID NO 1
<211> LENGTH: 540
<212> TYPE: PRT
<213> ORGANISM: Artificial Sequence
<220> FEATURE:
<223> OTHER INFORMATION: Composite GII.4 Norovirus VP1 amino acid
      sequence

<400> SEQUENCE: 1
```

Met Lys Met Ala Ser Ser Asp Ala Asn Pro Ser Asp Gly Ser Thr Ala
1               5                   10                  15

Asn Leu Val Pro Glu Val Asn Asn Glu Val Met Ala Leu Glu Pro Val
            20                  25                  30

Val Gly Ala Ala Ile Ala Ala Pro Val Ala Gly Gln Gln Asn Val Ile
        35                  40                  45

Asp Pro Trp Ile Arg Asn Asn Phe Val Gln Ala Pro Gly Gly Glu Phe
    50                  55                  60

Thr Val Ser Pro Arg Asn Ala Pro Gly Glu Ile Leu Trp Ser Ala Pro
65                  70                  75                  80

Leu Gly Pro Asp Leu Asn Pro Tyr Leu Ser His Leu Ala Arg Met Tyr
                85                  90                  95

Asn Gly Tyr Ala Gly Gly Phe Glu Val Gln Val Ile Leu Ala Gly Asn
            100                 105                 110

Ala Phe Thr Ala Gly Lys Ile Ile Phe Ala Ala Val Pro Pro Asn Phe
        115                 120                 125

Pro Thr Glu Gly Leu Ser Pro Ser Gln Val Thr Met Phe Pro His Ile
    130                 135                 140

Ile Val Asp Val Arg Gln Leu Glu Pro Val Leu Ile Pro Leu Pro Asp

```
            145                 150                 155                 160
Val Arg Asn Asn Phe Tyr His Tyr Asn Gln Ser Asn Asp Pro Thr Ile
                    165                 170                 175

Lys Leu Ile Ala Met Leu Tyr Thr Pro Leu Arg Ala Asn Asn Ala Gly
                180                 185                 190

Asp Asp Val Phe Thr Val Ser Cys Arg Val Leu Thr Arg Pro Ser Pro
                195                 200                 205

Asp Phe Asp Phe Ile Phe Leu Val Pro Pro Thr Val Glu Ser Arg Thr
            210                 215                 220

Lys Pro Phe Thr Val Pro Ile Leu Thr Val Glu Glu Met Thr Asn Ser
225                 230                 235                 240

Arg Phe Pro Ile Pro Leu Glu Lys Leu Phe Thr Gly Pro Ser Gly Ala
                245                 250                 255

Phe Val Val Gln Pro Gln Asn Gly Arg Cys Thr Thr Asp Gly Val Leu
                260                 265                 270

Leu Gly Thr Thr Gln Leu Ser Pro Val Asn Ile Cys Thr Phe Arg Gly
                275                 280                 285

Asp Val Thr His Ile Ala Gly Thr Gln Glu Tyr Thr Met Asn Leu Ala
                290                 295                 300

Ser Gln Asn Trp Asn Asn Tyr Asp Pro Thr Glu Glu Ile Pro Ala Pro
305                 310                 315                 320

Leu Gly Thr Pro Asp Phe Val Gly Lys Ile Gln Gly Val Leu Thr Gln
                325                 330                 335

Thr Thr Arg Gly Asp Gly Ser Thr Arg Gly His Lys Ala Thr Val Ser
                340                 345                 350

Thr Gly Ser Val His Phe Thr Pro Lys Leu Gly Ser Val Gln Phe Ser
                355                 360                 365

Thr Asp Thr Ser Asn Asp Phe Glu Thr Gly Gln Asn Thr Lys Phe Thr
                370                 375                 380

Pro Val Gly Val Val Gln Asp Gly Ser Thr Thr His Gln Asn Glu Pro
385                 390                 395                 400

Gln Gln Trp Val Leu Pro Asp Tyr Ser Gly Arg Asp Ser His Asn Val
                405                 410                 415

His Leu Ala Pro Ala Val Ala Pro Thr Phe Pro Gly Glu Gln Leu Leu
                420                 425                 430

Phe Phe Arg Ser Thr Met Pro Gly Cys Ser Gly Tyr Pro Asn Met Asn
                435                 440                 445

Leu Asp Cys Leu Leu Pro Gln Glu Trp Val Gln His Phe Tyr Gln Glu
                450                 455                 460

Ala Ala Pro Ala Gln Ser Asp Val Ala Leu Leu Arg Phe Val Asn Pro
465                 470                 475                 480

Asp Thr Gly Arg Val Leu Phe Glu Cys Lys Leu His Lys Ser Gly Tyr
                485                 490                 495

Val Thr Val Ala His Thr Gly Gln His Asp Leu Val Ile Pro Pro Asn
                500                 505                 510

Gly Tyr Phe Arg Phe Asp Ser Trp Val Asn Gln Phe Tyr Thr Leu Ala
                515                 520                 525

Pro Met Gly Asn Gly Thr Gly Arg Arg Arg Ala Leu
530                 535                 540
```